US009751071B2

(12) United States Patent
Kim et al.

(10) Patent No.: US 9,751,071 B2
(45) Date of Patent: Sep. 5, 2017

(54) CONTINUOUS MICROWAVE-ASSISTED SEGMENTED FLOW REACTOR FOR HIGH-QUALITY NANOCRYSTAL SYNTHESIS

(71) Applicant: State of Oregon acting by and through the State board of higher education on behalf of OSU, Corvallis, OR (US)

(72) Inventors: Ki-Joong Kim, Corvallis, OR (US); Eric Bradley Hostetler, Corvallis, OR (US); Gregory Scott Herman, Albany, OR (US); Daniel Alan Peterson, Corvallis, OR (US); Chih-hung Chang, Corvallis, OR (US); Brendan Thomas Flynn, Corvallis, OR (US); Brian Kevin Paul, Corvallis, OR (US); Richard Paul Oleksak, Corvallis, OR (US)

(73) Assignee: STATE OF OREGON ACTING BY AND THROUGH THE STATE BOARD OF HIGHER EDUCATION ON BEHALF OF OREGON STATE UNIVERSITY, Corvallis, OR (US)

(*) Notice: Subject to any disclaimer, the term of this patent is extended or adjusted under 35 U.S.C. 154(b) by 0 days.

(21) Appl. No.: 14/582,514

(22) Filed: Dec. 24, 2014

(65) Prior Publication Data
US 2015/0182936 A1   Jul. 2, 2015

Related U.S. Application Data

(60) Provisional application No. 61/921,229, filed on Dec. 27, 2013.

(51) Int. Cl.
*B01J 19/12* (2006.01)
*C07F 15/04* (2006.01)
(Continued)

(52) U.S. Cl.
CPC .......... *B01J 19/126* (2013.01); *C01B 19/002* (2013.01); *C01B 19/007* (2013.01); *C01G 9/08* (2013.01);
(Continued)

(58) Field of Classification Search
CPC .............. B01J 19/126; B01J 2219/0877; B01J 2219/0871; C01G 19/006; C01G 15/006;
(Continued)

(56) References Cited

U.S. PATENT DOCUMENTS

| 3,202,281 A | 8/1965 | Weston |
| 5,534,328 A | 7/1996 | Ashmead et al. |

(Continued)

FOREIGN PATENT DOCUMENTS

WO   2014153266   9/2014

OTHER PUBLICATIONS

Rossetti, R.; Nakahara, S.; Brus, L., Quantum size effects in the redox potentials, resonance Raman spectra, and electronic spectra of CdS crystallites in aqueous solution. The Journal of Chemical Physics 1983,79 (2), 1086-1088.
(Continued)

*Primary Examiner* — Timothy Vanoy
(74) *Attorney, Agent, or Firm* — Niels Haun; Dann, Dorfman, Herrell and Skillman, P.C.

(57) ABSTRACT

Systems and methods for synthesizing high-quality nanocrystals via segmented, continuous flow microwave-assisted reactor were developed.

36 Claims, 35 Drawing Sheets

(51) Int. Cl.
*C01G 19/00* (2006.01)
*C01G 15/00* (2006.01)
*C01B 19/00* (2006.01)
*C01B 19/04* (2006.01)
*C01G 9/08* (2006.01)

(52) U.S. Cl.
CPC ......... *C01G 15/006* (2013.01); *C01G 19/006* (2013.01); *C07F 15/045* (2013.01); *B01J 2219/0871* (2013.01); *B01J 2219/0877* (2013.01); *C01P 2002/01* (2013.01); *C01P 2002/72* (2013.01); *C01P 2002/78* (2013.01); *C01P 2002/80* (2013.01); *C01P 2002/82* (2013.01); *C01P 2002/84* (2013.01); *C01P 2004/04* (2013.01); *C01P 2004/51* (2013.01); *C01P 2004/64* (2013.01); *C01P 2004/80* (2013.01)

(58) Field of Classification Search
CPC ..... C01G 9/08; C01P 2004/64; C01B 19/002; C01B 17/20
See application file for complete search history.

(56) References Cited

U.S. PATENT DOCUMENTS

| | | | |
|---|---|---|---|
| 6,458,335 | B1 | 10/2002 | Lemaitre et al. |
| 6,676,835 | B2 | 1/2004 | O'Connor et al. |
| 7,252,814 | B2 | 8/2007 | De Mello et al. |
| 7,470,308 | B2 | 12/2008 | Shiraishi et al. |
| 7,507,380 | B2 | 3/2009 | Chang et al. |
| 7,615,169 | B2 | 11/2009 | Strouse et al. |
| 7,829,059 | B2 | 11/2010 | Guo et al. |
| 7,846,489 | B2 | 12/2010 | Chang |
| 8,236,599 | B2 | 8/2012 | Chang et al. |
| 8,414,182 | B2 | 4/2013 | Paul et al. |
| 8,553,333 | B2 | 10/2013 | Chang et al. |
| 8,622,606 | B2 | 1/2014 | Miller |
| 8,679,587 | B2 | 3/2014 | Chang et al. |
| 8,753,418 | B2 | 6/2014 | Epshteyn et al. |
| 8,801,979 | B2 | 8/2014 | Chang et al. |
| 9,073,761 | B2 | 7/2015 | Palanisamy et al. |
| 2004/0025634 | A1 | 2/2004 | Nakamura et al. |
| 2006/0061017 | A1* | 3/2006 | Strouse .................... B01J 13/00 264/489 |
| 2007/0227898 | A1 | 10/2007 | Mueller |
| 2007/0264834 | A1* | 11/2007 | Strouse .................... B01J 13/00 438/708 |
| 2008/0108122 | A1 | 5/2008 | Paul et al. |
| 2009/0295005 | A1 | 12/2009 | Rauscher et al. |
| 2011/0288060 | A1 | 11/2011 | Ruecroft et al. |
| 2012/0001356 | A1 | 1/2012 | Chang et al. |
| 2014/0264171 | A1 | 9/2014 | Schut |

OTHER PUBLICATIONS

Ekimov, A.; Onushchenko, A., Quantum size effect in three-dimensional microscopic semiconductor crystals. ZhETF Pisma Redaktsiiu 1981,34, 363.
Peng, Z. A.; Peng, X., Nearly monodisperse and shape-controlled CdSe nanocrystals via alternative routes: nucleation and growth. J. Am. Chem. Soc. 2002,124 (13), 3343-3353.
Yuan, Y.; Riehle, F.-S.; Gu, H.; Thomann, R.; Urban, G.; Krüger, M., Critical parameters for the scale-up synthesis of quantum dots. Journal of nanoscience and nanotechnology 2010,10 (9), 6041-6045.
Li, L.; Pandey, A.; Werder, D. J.; Khanal, B. P.; Pietryga, J. M.; Klimov, V. I., Efficient synthesis of highly luminescent copper indium sulfide-based core/shell nanocrystals with surprisingly long-lived emission. J. Am. Chem. Soc. 2011,133 (5), 1176-1179.
Joo, J.; Na, H. B.; Yu, T.; Yu, J. H.; Kim, Y. W.; Wu, F.; Zhang, J. Z.; Hyeon, T., Generalized and facile synthesis of semiconducting metal sulfide nanocrystals. J. Am. Chem. Soc. 2003,125 (36), 11100-11105.
Wiles, C.; Watts, P., Continuous flow reactors, a tool for the modern synthetic chemist. Eur. J. Org. Chem. 2008,2008 (10), 1655-1671.
Bilecka, I.; Niederberger, M., Microwave chemistry for inorganic nanomaterials synthesis. Nanoscale 2010,2 (8), 1358-1374.
Hostetler, E. B.; Kim, K.-J.; Oleksak, R. P.; Fitzmorris, R. C.; Peterson, D. A.; Chandran, P.; Chang, C.-H.; Paul, B. K.; Schut, D. M.; Herman, G. S., Synthesis of colloidal PbSe nanoparticles using a microwave-assisted segmented flow reactor. Mater. Lett. 2014,128, 54-59.
Bensebaa, F.; Durand, C.; Aouadou, A.; Scoles, L.; Du, X.; Wang, D.; Le Page, Y., A new green synthesis method of CuInS2 and CuInSe2 nanoparticles and their integration into thin films. J. Nanopart. Res. 2010,12 (5), 1897-1903.
Elinder, C., Cadmium as an environmental hazard. IARC scientific publications 1991, (118), 123-132.
Uehara, M.; Watanabe, K.; Tajiri, Y.; Nakamura, H.; Maeda, H., Synthesis of CuInS2 fluorescent nanocrystals and enhancement of fluorescence by controlling crystal defect. The Journal of chemical physics 2008,129 (13), 134709.
Speranskaya, E. S.; Beloglazova, N. V.; Abe, S.; Aubert, T.; Smet, P. F.; Poelman, D.; Goryacheva, I.; De Saeger, S.; Hens, Z., Hydrophilic, Bright CuInS2 Quantum Dots as Cd-free Fluorescent Labels in Quantitative Immunoassay. Langmuir 2014.
De Trizio, L.; Prato, M.; Genovese, A.; Casu, A.; Povia, M.; Simonutti, R.; Alcocer, M. J.; D\Andrea, C.; Tassone, F.; Manna, L., Strongly Fluorescent Quaternary Cu—In—Zn—S Nanocrystals Prepared from Cu1-x InS2 Nanocrystals by Partial Cation Exchange. Chem. Mater. 2012,24 (12), 2400-2406.
Nam, D.-E.; Song, W.-S.; Yang, H., Noninjection, one-pot synthesis of Cu-deficient CuInS2/ZnS core/shell quantum dots and their fluorescent properties. J. Colloid Interface Sci. 2011,361 (2), 491-496.
Yu, K.; Ng, P.; Ouyang, J.; Zaman, M. B.; Abulrob, A.; Baral, T. N.; Fatehi, D.; Jakubek, Z. J.; Kingston, D.; Wu, X., Low-Temperature Approach to Highly Emissive Copper Indium Sulfide Colloidal Nanocrystals and Their Bioimaging Applications. ACS Appl. Mater. Interfaces 2013,5 (8), 2870-2880.
Zhong, H.; Lo, S. S.; Mirkovic, T.; Li, Y.; Ding, Y.; Li, Y.; Scholes, G. D., Noninjection gram-scale synthesis of monodisperse pyramidal CuInS2 nanocrystals and their size-dependent properties. ACS nano 2010,4 (9), 5253-5262.
Castro, S. L.; Bailey, S. G.; Raffaelle, R. P.; Banger, K. K.; Hepp, A. F., Synthesis and characterization of colloidal CuInS2 nanoparticles from a molecular single-source precursor. J. Phys. Chem. B 2004,108 (33), 12429-12435.
Wu, K.; Wang, D., Temperature dependent Raman investigation of CuInS2 with mixed phases of chalcopyrite and CuAu. physica status solidi (a) 2011,208 (12), 2730-2736.
Fitzmorris, R. C.; Pu, Y.-C.; Cooper, J. K.; Lin, Y.-F.; Hsu, Y.-J.; Li, Y.; Zhang, J. Z., Optical Properties and Exciton Dynamics of Alloyed Core/Shell/Shell CdxZn1-xSe/ZnSe/ZnS Quantum Dots. ACS Appl. Mater. Interfaces 2013,5 (8), 2893-2900.
Park, J.; Kim, S.-W., CuInS 2/ZnS core/shell quantum dots by cation exchange and their blue-shifted photoluminescence. J. Mater. Chem. 2011,21 (11), 3745-3750.
R. J. Kuppler, D. J. Timmons, Q.-R. Fang, J.-R. Li, T. A. Makal, M. D. Young, D. Yuan, D. Zhao, W. Zhuang, and H.-C. Zhou, "Potential applications of metal-organic frameworks," Coord. Chem. Rev., vol. 253, No. 23-24, pp. 3042-3066, Dec. 2009.
N. L. Rosi, J. Kim, M. Eddaoudi, B. Chen, M. O\Keeffe, and O. M. Yaghi, "Rod Packings and Metal Organic Frameworks Constructed from Rod-Shaped Secondary Building Units," J. Am. Chem. Soc., vol. 127, No. 5, pp. 1504-1518, Feb. 2005.
H. Furukawa, K. E. Cordova, M. O\Keeffe, and O. M. Yaghi, "The Chemistry and Applications of Metal-Organic Frameworks," Science, vol. 341, No. 6149, pp. 1230444-1230444, Aug. 2013.
P. D. C. Dietzel, P. A. Georgiev, J. Eckert, R. Blom, T. Strässle, and T. Unruh, "Interaction of hydrogen with accessible metal sites in the metal-organic frameworks M2(dhtp) (CPO-27-M; M=Ni, Co, Mg)," Chem. Commun., vol. 46, No. 27, p. 4962, 2010.

(56) References Cited

OTHER PUBLICATIONS

M. T. Kapelewski, S. J. Geier, M. R. Hudson, D. Stück, J. A. Mason, J. N. Nelson, D. J. Xiao, Z. Hulvey, E. Gilmour, S. A. FitzGerald, M. Head-Gordon, C. M. Brown, and J. R. Long, "M 2 ( m-dobdc) (M=Mg, Mn, Fe, Co, Ni) Metal-Organic Frameworks Exhibiting Increased Charge Density and Enhanced H 2 Binding at the Open Metal Sites," J. Am. Chem. Soc., vol. 136, No. 34, pp. 12119-12129, Aug. 2014.

S. S. Kaye, A. Dailly, O. M. Yaghi, and J. R. Long, "Impact of Preparation and Handling on the Hydrogen Storage Properties of Zn 4 O(1,4-benzenedicarboxylate) 3 (MOF-5)," J. Am. Chem. Soc., vol. 129, No. 46, pp. 14176-14177, Nov. 2007.

A. R. Millward and O. M. Yaghi, "Metal Organic Frameworks with Exceptionally High Capacity for Storage of Carbon Dioxide at Room Temperature," J. Am. Chem. Soc., vol. 127, No. 51, pp. 17998-17999, Dec. 2005.

R. Plessius, R. Kromhout, A. L. D. Ramos, M. Ferbinteanu, M. C. Mittelmeijer-Hazeleger, R. Krishna, G. Rothenberg, and S. Tanase, "Highly Selective Water Adsorption in a Lanthanum Metal-Organic Framework," Chem.—Eur. J., vol. 20, No. 26, pp. 7922-7925, Jun. 2014.

N. L. Rosi, "Hydrogen Storage in Microporous Metal-Organic Frameworks," Science, vol. 300, No. 5622, pp. 1127-1129, May 2003.

D. Saha, R. Zacharia, L. Lafi, D. Cossement, and R. Chahine, "Synthesis, characterization and hydrogen adsorption properties of metal-organic framework AI-TCBPB," Int. J. Hydrog. Energy, vol. 37, No. 6, pp. 5100-5107, Mar. 2012.

S. Chavan, F. Bonino, L. Valenzano, B. Civalleri, C. Lamberti, N. Acerbi, J. H. Cavka, M. Leistner, and S. Bordiga, "Fundamental Aspects of H 2 S Adsorption on CPO-27-Ni," J. Phys. Chem. C, vol. 117, No. 30, pp. 15615-15622, Aug. 2013.

A. Das, P. D. Southon, M. Zhao, C. J. Kepert, A. T. Harris, and D. M. D\Alessandro, "Carbon dioxide adsorption by physisorption and chemisorption interactions in piperazine-grafted Ni2(dobdc) (dobdc=1,4-dioxido-2,5-benzenedicarboxylate)," Dalton Trans., vol. 41, No. 38, p. 11739, 2012.

T. Grant Glover, G. W. Peterson, B. J. Schindler, D. Britt, and O. Yaghi, "MOF-74 building unit has a direct impact on toxic gas adsorption," Chem. Eng. Sci., vol. 66, No. 2, pp. 163-170, Jan. 2011.

Z. R. Herm, E. D. Bloch, and J. R. Long, "Hydrocarbon Separations in Metal-Organic Frameworks," Chem. Mater., vol. 26, No. 1, pp. 323-338, Jan. 2014.

P. Kanoo, A. C. Ghosh, S. T. Cyriac, and T. K. Maji, "A Metal-Organic Framework with Highly Polar Pore Surfaces: Selective CO2 Adsorption and Guest-Dependent On/Off Emission Properties," Chem.—Eur. J., vol. 18, No. 1, pp. 237-244, Jan. 2012.

J. Liu, J. Tian, P. K. Thallapally, and B. P. McGrail, "Selective CO 2 Capture from Flue Gas Using Metal-Organic Frameworks A Fixed Bed Study," J. Phys. Chem. C, vol. 116, No. 17, pp. 9575-9581, May 2012.

Q. Liu, L. Ning, S. Zheng, M. Tao, Y. Shi, and Y. He, "Adsorption of Carbon Dioxide by MIL-101(Cr): Regeneration Conditions and Influence of Flue Gas Contaminants," Sci. Rep., vol. 3, Oct. 2013.

J. J. Perry, S. L. Teich-McGoldrick, S. T. Meek, J. A. Greathouse, M. Haranczyk, and M. D. Allendorf, "Noble Gas Adsorption in Metal-Organic Frameworks Containing Open Metal Sites," J. Phys. Chem. C, vol. 118, No. 22, pp. 11685-11698, Jun. 2014.

P. K. Thallapally, J. W. Grate, and R. K. Motkuri, "Facile xenon capture and release at room temperature using a metal-organic framework: a comparison with activated charcoal," Chem. Commun., vol. 48, No. 3, p. 347, 2012.

X. Wu, Z. Bao, B. Yuan, J. Wang, Y. Sun, H. Luo, and S. Deng, "Microwave synthesis and characterization of MOF-74 (M=Ni, Mg) for gas separation," Microporous Mesoporous Mater., vol. 180, pp. 114-122, Nov. 2013.

J. Liu, L. Chen, H. Cui, J. Zhang, L. Zhang, and C.-Y. Su, "Applications of metal-organic frameworks in heterogeneous supramolecular catalysis," Chem Soc Rev, vol. 43, No. 16, pp. 6011-6061, May 2014.

J. Lee, O. K. Farha, J. Roberts, K. A. Scheidt, S. T. Nguyen, and J. T. Hupp, "Metal-organic framework materials as catalysts," Chem. Soc. Rev., vol. 38, No. 5, p. 1450, 2009.

L. E. Kreno, K. Leong, O. K. Farha, M. Allendorf, R. P. Van Duyne, and J. T. Hupp, "Metal-Organic Framework Materials as Chemical Sensors," Chem. Rev., vol. 112, No. 2, pp. 1105-1125, Feb. 2012.

S. Achmann, G. Hagen, J. Kita, I. M. Malkowsky, C. Kiener, and R. Moos, "Metal-Organic Frameworks for Sensing Applications in the Gas Phase," Sensors, vol. 9, No. 3, pp. 1574-1589, Mar. 2009.

S. Zhang, L. Han, L. Li, J. Cheng, D. Yuan, and J. Luo, "A Highly Symmetric Metal-Organic Framework Based on a Propeller-Like Ru-Organic Metalloligand for Photocatalysis and Explosives Detection," Cryst. Growth Des., vol. 13, No. 12, pp. 5466-5472, Dec. 2013.

S. Rojas, P. S. Wheatley, E. Quartapelle-Procopio, B. Gil, B. Marszalek, R. E. Morris, and E. Barea, "Metal-organic frameworks as potential multi-carriers of drugs," CrystEngComm, vol. 15, No. 45, p. 9364, 2013.

P. Horcajada, T. Chalati, C. Serre, B. Gillet, C. Sebrie, T. Baati, J. F. Eubank, D. Heurtaux, P. Clayette, C. Kreuz, J.-S. Chang, Y. K. Hwang, V. Marsaud, P.-N. Bories, L. Cynober, S. Gil, G. Férey, P. Couvreur, and R. Gref, "Porous metal-organic-framework nanoscale carriers as a potential platform for drug delivery and imaging," Nat. Mater., vol. 9, No. 2, pp. 172-178, Feb. 2010.

J. Liu, Y. Wang, A. I. Benin, P. Jakubczak, R. R. Willis, and M. D. LeVan, "CO 2 /H 2 O Adsorption Equilibrium and Rates on Metal Organic Frameworks: HKUST-1 and Ni/DOBDC," Langmuir, vol. 26, No. 17, pp. 14301-14307, Sep. 2010.

J. A. Mason, M. Veenstra, and J. R. Long, "Evaluating metal-organic frameworks for natural gas storage," Chem. Sci., vol. 5, No. 1, p. 32, 2014.

P. M. Schoenecker, C. G. Carson, H. Jasuja, C. J. J. Flemming, and K. S. Walton, "Effect of Water Adsorption on Retention of Structure and Surface Area of Metal-Organic Frameworks," Ind. Eng. Chem. Res., vol. 51, No. 18, pp. 6513-6519, May 2012.

J. Liu, A. I. Benin, A. M. B. Furtado, P. Jakubczak, R. R. Willis, and M. D. LeVan, "Stability Effects on CO 2 Adsorption for the DOBDC Series of Metal-Organic Frameworks," Langmuir, vol. 27, No. 18, pp. 11451-11456, Sep. 2011.

S. R. Caskey, A. G. Wong-Foy, and A. J. Matzger, "Dramatic Tuning of Carbon Dioxide Uptake via Metal Substitution in a Coordination Polymer with Cylindrical Pores," J. Am. Chem. Soc., vol. 130, No. 33, pp. 10870-10871, Aug. 2008.

P. D. C. Dietzel, B. Panella, M. Hirscher, R. Blom, and H. Fjellvåg, "Hydrogen adsorption in a nickel based coordination polymer with open metal sites in the cylindrical cavities of the desolvated framework," Chem. Commun., No. 9, p. 959, 2006.

L. Paseta, B. Seoane, D. Julve, V. Sebastián, C. Téllez, and J. Coronas, "Accelerating the Controlled Synthesis of Metal-Organic Frameworks by a Microfluidic Approach: A Nanoliter Continuous Reactor," ACS Appl. Mater. Interfaces, vol. 5, No. 19, pp. 9405-9410, Oct. 2013.

M. Faustini, J. Kim, G.-Y. Jeong, J. Y. Kim, H. R. Moon, W.-S. Ahn, and D.-P. Kim, "Microfluidic Approach toward Continuous and Ultrafast Synthesis of Metal-Organic Framework Crystals and Hetero Structures in Confined Microdroplets," J. Am. Chem. Soc., vol. 135, No. 39, pp. 14619-14626, Oct. 2013.

M. Li and M. Dincă†, "Reductive Electrosynthesis of Crystalline Metal-Organic Frameworks," J. Am. Chem. Soc., vol. 133, No. 33, pp. 12926-12929, Aug. 2011.

N. Campagnol, T. Van Assche, T. Boudewijns, J. Denayer, K. Binnemans, D. De Vos, and J. Fransaer, "High pressure, high temperature electrochemical synthesis of metal-organic frameworks: films of MIL-100 (Fe) and HKUST-1 in different morphologies," J. Mater. Chem. A, vol. 1, No. 19, p. 5827, 2013.

J.-S. Lee, S. B. Halligudi, N.-H. Jang, D.-W. Hwang, J.-S. Chang, and Y.-K. Hwang, "Microwave Synthesis of a Porous Metal-Organic Framework, Nickel(II) Dihydroxyterephthalate and its

(56) References Cited

OTHER PUBLICATIONS

Catalytic Properties in Oxidation of Cyclohexene," Bull. Korean Chem. Soc., vol. 31, No. 6, pp. 1489-1495, Jun. 2010.
E. Haque, N. A. Khan, J. H. Park, and S. H. Jhung, "Synthesis of a Metal-Organic Framework Material, Iron Terephthalate, by Ultrasound, Microwave, and Conventional Electric Heating: A Kinetic Study," Chem.—Eur. J., vol. 16, No. 3, pp. 1046-1052, Jan. 2010.
E. Haque and S. H. Jhung, "Synthesis of isostructural metal-organic frameworks, CPO-27s, with ultrasound, microwave, and conventional heating: Effect of synthesis methods and metal ions," Chem. Eng. J., vol. 173, No. 3, pp. 866-872, Oct. 2011.
N. A. Khan and S. H. Jhung, "Synthesis of metal-organic frameworks (MOFs) with microwave or ultrasound: Rapid reaction, phase-selectivity, and size reduction," Coord. Chem. Rev., Nov. 2014.
J. Ren, T. Segakweng, H. W. Langmi, N. M. Musyoka, B. C. North, M. Mathe, and D. Bessarabov, "Microwave-assisted modulated synthesis of zirconium-based metal-organic framework (Zr-MOF) for hydrogen storage applications," Int. J. Mater. Res., vol. 105, No. 5, pp. 516-519, 2014.
C.-M. Lu, J. Liu, K. Xiao, and A. T. Harris, "Microwave enhanced synthesis of MOF-5 and its CO2 capture ability at moderate temperatures across multiple capture and release cycles," Chem. Eng. J., vol. 156, No. 2, pp. 465-470, Jan. 2010.
K.-J. Kim, Y. J. Li, P. B. Kreider, C.-H. Chang, N. Wannenmacher, P. K. Thallapally, and H.-G. Ahn, "High-rate synthesis of Cu-BTC metal-organic frameworks," Chem. Commun., vol. 49, No. 98, p. 11518, 2013.
P. M. Schoenecker, G. A. Belancik, B. E. Grabicka, and K. S. Walton, "Kinetics study and crystallization process design for scale-up of UiO-66-NH 2 synthesis," AIChE J., vol. 59, No. 4, pp. 1255-1262, Apr. 2013.
P. A. Bayliss, I. A. Ibarra, E. Pérez, S. Yang, C. C. Tang, M. Poliakoff, and M. Schröder, "Synthesis of metal-organic frameworks by continuous flow," Green Chem., vol. 16, No. 8, p. 3796, Jun. 2014.
M. Rubio-Martinez, M. P. Batten, A. Polyzos, K.-C. Carey, J. I. Mardel, K.-S. Lim, and M. R. Hill, "Versatile, High Quality and Scalable Continuous Flow Production of Metal-Organic Frameworks," Sci. Rep., vol. 4, Jun. 2014.
M. Gimeno-Fabra, A. S. Munn, L. A. Stevens, T. C. Drage, D. M. Grant, R. J. Kashtiban, J. Sloan, E. Lester, and R. I. Walton, "Instant MOFs: continuous synthesis of metal-organic frameworks by rapid solvent mixing," Chem. Commun., vol. 48, No. 86, p. 10642, 2012.
S. Cadot, L. Veyre, D. Luneau, D. Farrusseng, and E. Alessandra Quadrelli, "A water-based and high space-time yield synthetic route to MOF Ni 2 (dhtp) and its linker 2,5-dihydroxyterephthalic acid," J Mater Chem A, vol. 2, No. 42, pp. 17757-17763, Jul. 2014.
K.-J. Kim, R. P. Oleksak, E. B. Hostetler, D. A. Peterson, P. Chandran, D. M. Schut, B. K. Paul, G. S. Herman, and C.-H. Chang, "Continuous Microwave-Assisted Gas-Liquid Segmented Flow Reactor for Controlled Nucleation and Growth of Nanocrystals," Cryst. Growth Des., vol. 14, No. 11, pp. 5349-5355, Nov. 2014.
S. Horikoshi and N. Serpone, Microwaves in Nanoparticle Synthesis: Fundamentals and Applications. Wiley-VCH, 2013, Chapters 5, 7, and 10.
R. P. Oleksak, B. T. Flynn, D. M. Schut, and G. S. Herman, "Microwave-assisted synthesis of CuInSe 2 nanoparticles in low-absorbing solvents: Microwave-assisted synthesis of CuInSe 2 nanoparticles," Phys. Status Solidi A, vol. 211, No. 1, pp. 219-225, Jan. 2014.
F. Bonino, S. Chavan, J. G. Vitillo, E. Groppo, G. Agostini, C. Lamberti, P. D. C. Dietzel, C. Prestipino, and S. Bordiga, "Local Structure of CPO-27-Ni Metallorganic Framework upon Dehydration and Coordination of NO," Chem. Mater., vol. 20, No. 15, pp. 4957-4968, Aug. 2008.
W. Wang, et al., "Device Characteristics of CZTSSe Thin-Film Solar Cells with 12.6% Efficiency," Adv. Ener. Mater. 4, 1301465 (2014).

B. Flynn, W. Wang, C.-H. Chang, G.S. Herman, Physica Status Solidi A, 209, 2186-2194 (2012).
B. Flynn, I. Braly, P. Glover, R.P. Oleksak, C. Durgan, G.S. Herman, Materials Letters, 107, 214-217 (2013).
B. J. Stanbery, Crit. Rev. Solid State Mater. Sci., 2002, 27, 73.
M. Kemell, M.Ritala and M.Leskela, Crit. Rev. Solid State Mater. Sci., 2005, 30, 1.
S. Siebentritt, Sol. Energy Mater. Sol. Cells, 2011, 95, 1471.
D. Aldakov, A. Lefrancois and P. Reiss, J. Mater. Chem. C, 2013, 1, 3756.
O. Chen, H. Wei, A. Maurice, M. Bawendi and P. Reiss, MRS Bulletin, 2013, 38, 696.
E. Cassette, T. Pons, C. Bouet, M. Helle, L. Bezdetnaya, F. Marchal and B. Dubertret, Chem. Mater.,2010, 22, 6117.
V. A. Akhavan, B. W. Goodfellow, M. G. Panthani, D. K. Reid, D. J. Hellebusch, T. Adachi and B. A. Korgel, Energy Environ.Sci., 2010, 3, 1600.
W.-J. Wang, Y. Jiang, X.-Z.Lan, C. Wang, X.-M. Liu, B.-B. Wang, J.-W. Li, B. Yang and X.-N. Ding, Mater. Sci. Semicond. Process., 2012, 15, 467.
Q. Guo, S. J. Kim, M.Kar, W. N. Shafarman, R. W. Birkmire, E. A. Stach, R.Agrawal and H. W. Hillhouse, Nano Lett., 2008, 8, 2982.
D. B. Mitzi, Adv. Mater., 2009, 21, 3141.
M. E. Norako and R. L. Brutchey, Chem. Mater., 2010, 22, 1613.
M. G. Panthani, V.Akhavan, B.Goodfellow, J. P. Schmidtke, L. Dunn, A.Dodabalapur, P. F. Barbara and B. A. Korgel, J. Am. Chem. Soc., 2008, 130, 16770.
H.Zhong, Y. Li, M. Ye, Z. Zhu, Y. Zhou, C. Yang and Y. Li, Nanotechnology, 2007, 18, 025602.
J. Tang, S. Hinds, S. O. Kelly and E. H. Sargent, Chem. Mater., 2008, 20, 6906.
W. Wang, Y.-W. Su and C.-H. Chang, Sol. Energy Mater. Sol. Cells, 2011, 95 2616.
W. Wang, S.-Y. Han, S.-J. Sung, D.-H. Kim and C.-H.Chang, Phys. Chem. Chem. Phys., 2012, 14, 11154.
S. E. Habas, H. A. S. Platt, M. F. A. M. van Hest and D. S. Ginley, Chem. Rev., 2010, 110, 6571.
H. W. Hillhouse and M. C. Beard, Curr. Opin. Colloid Interface Sci., 2009, 14, 245.
J. Jean, S. Chang, P.R. Brown, J.J. Cheng, P. H. Rekemeyer, M.G. Bawendi, S. Grade•k andV. Bulovi‡, Adv. Mat., 2013, 25, 2790.
I. Gur, N. A. Fromer, M. L. Geier and A. P. Alivisatos, Science, 2005, 310, 462.
A. Shavel, D. Cadavid, M. Ibanez, A. Carrete and A. Cabot, J. Am. Chem. Soc., 2011, 134, 1438.
G.J. Supran, Y. Shirasaki, K.W. Song, J.M. Caruge, P.T. Kazlas, S. Coe-Sullivan, T.L. Andre, M.G. Bawendi and V. Bulovi‡, MRS Bulletin, 2013, 38, 703.
Y. Yin and A. P. Alivisatos, Nature, 2005, 437, 664.
J. Park, K. An, Y. Hwang, J.-G. Park, H.-J. Noh, J.-Y. Kim, J.-H. Park, N.-M. Hwang and T. Hyeon, Nat. Mater., 2004, 3, 891.
J. Park, J.Joo, S. G. Kwon, Y. Jang and T. Hyeon, Angew. Chem. Int. Ed., 2007, 46, 4630.
B. Li, Y. Xie, J. Huang and Y. Qian, Adv. Mater., 1999, 11, 1456.
C. J. Carmalt, D. E. Morrison and I. P. Parkin, J. Mater. Chem., 1998, 8, 2209.
M. A. Malik, P. O'Brien and N. Revaprasadu, Adv. Mater., 1999, 11, 1441.
M. Kar, R. Agrawal and H. W. Hillhouse, J. Am. Chem. Soc., 2011, 133, 17239.
H. D. Jin and C.-H. Chang, J. Nanopart. Res., 2012, 14, 1180.
J. Xu, C.-S. Lee, Y.-B. Tang, X. Chen, Z.-H. Chen, W.-J. Zhang, S.-T. Lee, W. Zhang and Z. Yang, ACS Nano, 2010, 4, 1845.
S. Deka, A. Genovese, Y. Zhang, K. Miszta, G. Bertoni, R. Krahne, C. Giannini and L. Manna, J. Am. Chem. Soc., 2010, 132, 8912.
C. M. Hessel, V. P. Pattani, M. Rasch, M. G. Panthani, B. Koo, J. W. Tunnell and B. A. Korgel, Nano Lett., 2011, 11, 2560.
S. L. Castro, S. G. Bailey, R. P. Raffaelle, K. K. Banger and A. F. Hepp, Chem. Mater., 2003, 15, 3142.
B. Koo, R. N. Patel and B. A. Korgel, J. Am. Chem. Soc., 2009, 131, 3134.

(56) References Cited

OTHER PUBLICATIONS

C. Steinhagen, V. A. Akhavan, B. W. Goodfellow, M. G. Panthani, J. T. Harris, V. C. Holmberg and B. A. Korgel, ACS Appl. Mater. Interfaces, 2011, 3, 1781.
V. A. Akhavan, M. G. Panthani, B. W. Goodfellow, D. K. Reid and B. A. Korgel, Opt. Express, 2010, 18, A411.
S. Jeong, B.-S. Lee, S. J. Ahn, K.H. Yoon, Y.-H. Seo, Y. Choi and B.-H. Ryu, Energy Environ. Sci., 2012, 5, 7539.
Yen, Angewandte Chemie, 2005, 117, 5583.
Abou-Hassan, A., Sandre, O. and Cabuil, V. (2010), Microfluidics in Inorganic Chemistry. AngewandteChemie International Edition, 49: 6268-6286. doi:10.1002/anie.200904285.
Y.-J. Chang, P. H. Mugdur, S.-Y. Han, A. A. Morrone, S. O. Ryu, T.-J. Lee, and C.-H. Chang (2006), NanocrystallineCdS MISFETs Fabricated by a Novel Continuous Flow Microreactor Electrochem. Solid-State Lett. 9(5): G174-G177; doi:10.1149/1.2183847.
Chih-Hung Chang, Brian K. Paul, Vincent T. Remcho, SundarAtre, James E. Hutchison (2008), Synthesis and post-processing of nanomaterials using microreaction technology. Journal of Nanoparticle Research, 10:965-980; doi:10.1007/s11051-007-9355-y.
Li, D. and Komameni, S. (2006), Microwave-Assisted Polyol Process for Synthesis of Ni Nanoparticles. Journal of the American Ceramic Society, 89: 1510-1517. doi:10.1111/j.1551-2916.2006.00925.x.
P. H. Mugdur,Y.-J. Chang, S-.Y. Han, Y-W. Su, A. A. Morrone,S. O. Ryu,T.-J. Lee,and C.-H. Chang (2007), A Comparison of Chemical Bath Deposition of CdS froma Batch Reactor and a Continuous-Flow Microreactor. Journal of The Electrochemical Society, 154(9): D482-D488; doi: 10.1149/1.2757012.
Greg Schabas, Chih-Wei Wang, Ali Oskooei, Huda Yusuf, Matthew G. Moffitt, and David Sinton (2008), Formation and Shear-Induced Processing of Quantum Dot Colloidal Assemblies in a Multiphase Microfluidic Chip. Langmuir 24 (19): 10596-10603; DOI: 10.1021/la8022985.
Yen, B.K.H., Stott, N.E, Jensen, K.F. and Bawendi, M.G. (2003), A Continuous-Flow Microcapillary Reactor for the Preparation of a Size Series of CdSe Nanocrystals. Adv. Mater., 15: 1858-1862. doi:10.1002/adma.200305162.

Wei Xu, Kong Yong Liew, Hanfan Liu, Tao Huang, Chuntao Sun, Yanxi Zhao (2008), Microwave-assisted synthesis of nickel nanoparticles. Materials Letters62 (17-18): 2571-2573; doi:10.1016/j.matlet.2007.12.057.
Huanping Zhou et al., Facile single-component precursor for Cu2ZnSnS4 with enhanced phase and composition controllability, Energy Environ. Sci., 2014, 7, 998-1005.
Spehar, R. L; Anderson, R.L.; Fiandt, J. T.,Toxicity and bioaccumulation of cadmium and lead in aquatic invertebrates. Environmental Pollution (1970) 1978, 15 (3), 195-208.
Jongen, N., Donnet, M., Bowen, P., Lemaître, J., Hofmann, H., Schenk, R., Hofmann, C., Aoun-Habbache, M., Guillemet-Fritsch, S., Sarrias, J., Rousset, A., Viviani, M., Buscaglia, M.T., Buscaglia, V., Nanni, P., Testino, A. and Herguijuela, J.R. (2003), Development of a Continuous Segmented Flow Tubular Reactor and the "Scale-out" Concept—In Search of Perfect Powders. Chem. Eng. Technol., 26: 303-305. doi:10.1002/ceat.200390046.
Axel Günther, Manish Jhunjhunwala, Martina Thalmann, Martin A. Schmidt, and Klays F. Jensen (2005), Micromixing of Miscible Liquids in Segmented Gas-Liquid Flow. Langmuir 2005 21 (4), 1547-1555. DOI: 10.1021/la0482406.
Hiroyuki Nakamura, Yoshiko Yamaguchi, Masaya Miyazaki, Hideaki Maeda, Masato Uehara, and Paul Mulvaney (2002), Preparation of CdSe nanocrystals in a micro-flow-reactor. Chem. Commun. (23); 2844-2845. DOI: 10.1039/B208992K.
H. Zhou, C.-J. Hsu, and Y. Yang, Energy Environ. Sci. 6, 2822-2838 (2013).
Letter from M. Hall dated Feb. 16, 2016.
Email from M. Hall dated Apr. 5, 2016.
Email from M. Hall dated May 16, 2016.
Nist Tip . . . bkp.pdf, Jul. 2010.
Hall email Aug. 10, 2016.
Declaration of George Williams, with attachments, dated Dec. 14, 2016.
Johann M. Köhler, Shuning Li and Andrea Knauer; Why is Micro Segmented Flow Particularly Promising for the Synthesis of Nanomaterials?; Chem. Eng. Technol. 2013, 36, No. 6, 887-899.
Axel Günther, Saif A. Khan, Martina Thalmann, Franz Trachsel and Klavs F. Jensen; Transport and reaction in microscale segmented gas-liquid flow; Lab Chip, 2004, 4, 278-286.

* cited by examiner

CONTINUOUS MICROWAVE-ASSISTED SEGMENTED FLOW REACTOR FOR HIGH-QUALITY NANOCRYSTAL SYNTHESIS

CROSS-REFERENCE TO RELATED APPLICATIONS

This application claims the benefit of U.S. Provisional Application No. 61/921,229, filed Dec. 27, 2013, the entirety of which is incorporated herein by reference.

FIELD OF THE INVENTION

The present invention relates generally to the synthesis of high quality nanocrystals and more particularly but not exclusively to continuous, segmented flow systems and methods for nanocrystal synthesis that employ microwave radiation.

BACKGROUND OF THE INVENTION

Colloidal nanocrystals (NCs) have recently gained attention for their applications in light emitting diodes, lasers, quantum dots, and solar cells. The ability to produce high quality colloidal NCs with high-throughput is a key step in the development of low-cost processing. The ability to control the uniformity of the size, shape, composition and crystal structure of the NCs is also of technological interest.

NCs are generally synthesized by thermal decomposition of the precursors in a mixture of solvents and coordinating ligands. The most common procedure for synthesizing high-quality NCs has utilized a "hot injection" method to achieve burst nucleation. The conductive heating methods (such as isomantles, oil baths, or hot plates) are performed using small volume flasks, leading to low production rates. Furthermore, vessel temperature and mass transfer characteristics are not well defined and significant variation is commonly observed, especially if the vessel size is enlarged. These problems make the commercial scaling up of NCs problematic. Producing colloidal NCs via a continuous method provides an opportunity to reduce the required production time and lower the cost per mass of synthesized colloidal NCs.

The use of microwaves in the synthesis of colloidal NCs eliminates thermal gradients by uniformly heating the solution volume, and can be used to direct energy input to more microwave active species leading to highly controllable reaction conditions. A continuous flow microwave reactor system may be used to prepare large quantities of NCs. However, continuous systems known in the art lead to sparking inside the microwave flow path due to deposition and early precipitation of the NCs in the microwave zone. These, and other issues, are solved by the systems and methods of the present invention.

SUMMARY OF THE INVENTION

The invention sets forth a system and method that overcomes the shortcomings in the art and provides a continuous, segmented flow reactor system that allows for the production of high-quality nanocrystals (NCs), and materials that include such NCs, without sparking or clogging the reactor.

In a first aspect, the invention includes a continuous, microwave-assisted, segmented flow reactor system for NC synthesis that includes an NC precursor source that is configured to include an NC precursor solution. The system may further include a microwave reactor in fluid communication with the NC precursor source and having a fluid passageway passing through the microwave reactor configured to allow the NC precursor solution to pass therethrough. The system may also include a segmentation fluid source disposed in fluid communication with the fluid passageway at a location between the NC precursor source and the microwave reactor, the segmentation fluid source may be configured to provide a segmentation fluid that is immiscible with the NC precursor solution. As used herein, the term "immiscible" refers to two or more fluids being primarily immiscible, partially immiscible, and/or incapable of forming a homogeneous solution.

In a second aspect, the invention includes a method for synthesizing NCs using a continuous, microwave-assisted, segmented flow reactor, the method including the step of providing an NC precursor solution and then segmenting the NC precursor solution with a segmentation fluid that is immiscible with the NC precursor solution to yield a segmented NC precursor solution. In another step of the method, the segmented NC precursor solution may be continuously flowed through a microwave reactor having a microwave zone. Next, the segmented NC precursor solution flowing through the microwave zone may be irradiated to provide NCs. In another embodiment, the method may include growing the NCs in a growth zone.

The present invention provides a system and method that allow for the minimization of material deposition in a microwave reactor, which can lead to catastrophic failure through sparking.

BRIEF DESCRIPTION OF THE DRAWINGS

The foregoing summary and the following detailed description of the exemplary embodiments of the present invention may be further understood when read in conjunction with the appended drawings, in which:

(FIG. 3C), and microwave heating to 180° C. (FIG. 3D); and the deposition of $CuInSe_2$ NCs on the PTFE tube wall at 180° C. after 20 minutes of reaction time in a continuous flow microwave system (FIG. 3E).

FIG. 18A is a UV-Vis absorption spectrum of MW-only QDs referenced to the precursor solution. FIG. 18B is a UV-Vis absorption spectrum of core QDs after growth bath, following cation exchange, and after shell growth. The (a) absorbance of the core QDs is compared to the resulting (b) photoluminescence (PL).

FIG. 20A demonstrates Raman spectra for (a) core QDs and (b) core/shell QDs. FIG. 20B demonstrates an XRD of (a) core QDs and (b) core/shell QDs. The vertical lines indicate the known diffraction patterns for chalcopyrite CIS and ZnS, respectively.

(FIG. 25B) and at 150° C. (FIG. 25C).

DETAILED DESCRIPTION OF THE INVENTION

A significant issue that limits the application of microwave heating for the synthesis of nanoparticles is the deposition of material on the inner tubing in the reactor. The deposition of material leads to sparking in the microwave reaction zone, and unstable reaction conditions. The present invention solves this problem by utilizing a segmentation fluid that is introduced prior to the microwave reaction zone. This results in segmented flow in the microwave reaction zone and minimizes deposition on the tubing or passageway sidewall. In unsegmented flow (laminar flow regime), the fluid velocity decreases the closer a fluid element is to the wall due to drag resulting in a longer residence time for nanoparticles near the wall of the tube, which will grow larger than those in the middle of the tube and potentially deposit on the walls of the tubing. In contrast, for segmented flows the nanoparticles recirculate between fluid-fluid interfaces which results in a uniform residence time for all the nanoparticles. As used herein, the term "fluid-fluid" may include gas-liquid systems, liquid-liquid systems, or combinations thereof. This minimizes deposition on the inner tubing.

Figure 1:
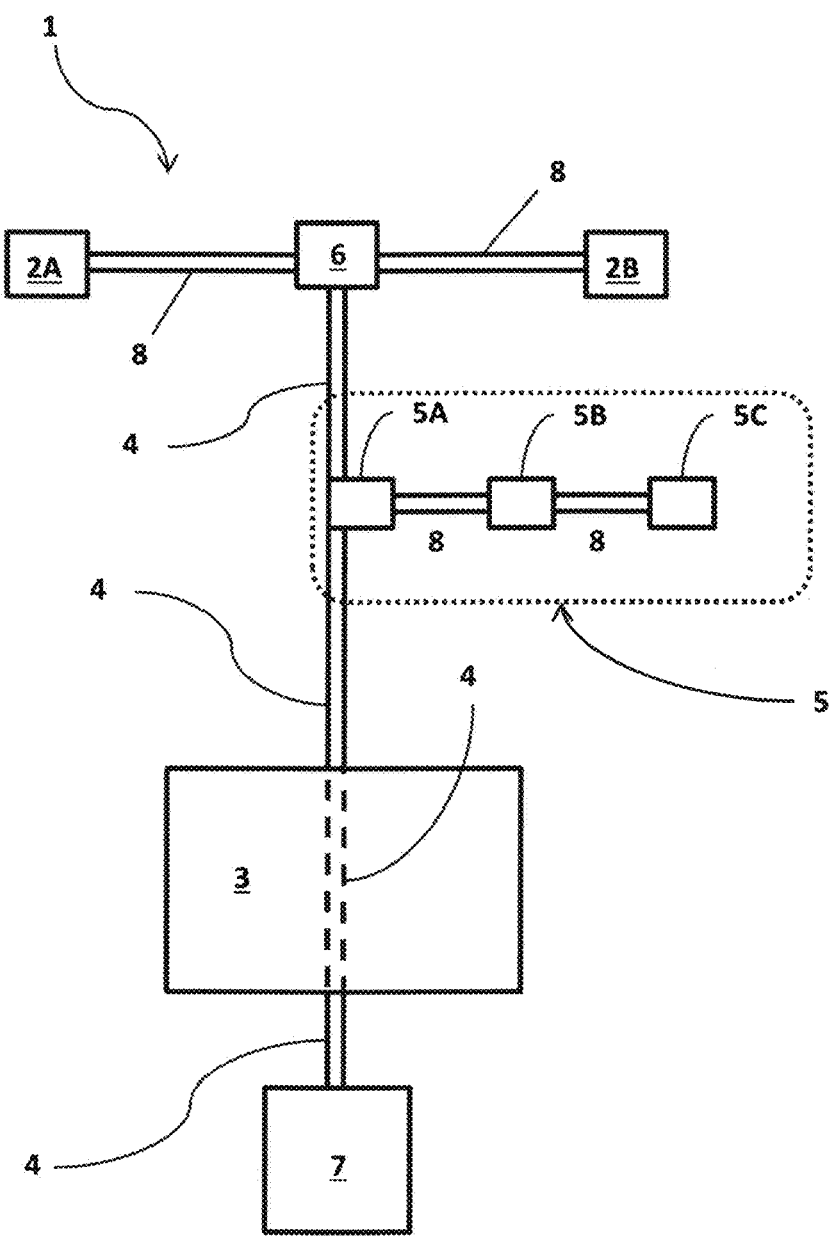
FIG. 1 schematically illustrates an exemplary continuous, microwave-assisted flow reactor system of the invention.

Referring now to the figures, wherein like elements are numbered alike throughout, a system of the invention is disclosed in FIG. 1. The present invention provides a continuous, microwave-assisted, segmented flow reactor system 1 for nanocrystal synthesis. The system 1 includes an NC precursor source 2 (i.e., 2A and/or 2B), a microwave reactor 3 and a fluid passageway 4 that provides fluid communication between the NC precursor source 2 that passes through the microwave reactor 3. Moreover, the system 1 includes a segmentation fluid source 5 that is disposed in fluid communication with the fluid passageway 4 at a location between the NC precursor source 2 and the microwave reactor 3.

Regarding the NC precursor source 2, the source may include more than one NC precursor source. For example, the NC precursor source 2 may include a first NC precursor source (2A) and a second NC precursor source (2B). The first and/or second NC precursor sources (2A and 2B) may include an NC precursor source container (not pictured) that contains an NC precursor solution. Further, the first and/or second NC precursor sources (2A and 2B) may also include one or more pumps to pump the NC precursor solution out of the NC precursor container and toward the fluid passageway 4.

The NC precursor solutions of the invention may include one or more NC precursors, one or more solvents, and/or one or more other agents as determined to be necessary by an ordinary artisan preparing NCs. Moreover, the NC precursor solutions in the first and second NC precursor sources (2A and 2B) may be the same or different. The NC precursors of the invention may include, for example, Ni, Cu, In, S, Ga, Se, Pb, Sn, Zn, P, Cd, Te, Ge, Si, Hg, O, Ag, Sb, Bi, Na, or combinations thereof. The NC precursors of the invention may also include, for example, Cu, In, S, Ga, Se, Pb, Sn, Zn, P, Cd, Te, Ge, Si, Hg, O, Ag, Sb, Bi, Na, or combinations thereof. In certain aspects, the NC precursors of the invention may include Cu, In, S, Se, Pb, Ni, Sn, Zn, or combinations thereof. In another aspect, the NC precursors include Cu, In, Se, or a combination thereof. Additionally, the NC precursors of the invention may be provided in a charged or neutral state, as necessary, and are preferably provided as salts and/or organometallic molecules. Regarding the solvents used in NC precursor solutions of the invention, such solvents may include polar or non-polar solvents, as necessary to substantially dissolve the NC precursors and may include, for example, oleylamine, trioctylphosphine, trioctylphosphine oxide, hexadecylamine, water, triethylene glycol, ethylene glycol, oleic acid, dodecanethiol, dioctyl ether, 1-octadecene, glycerol, 1,3-propanediol-1,4-butanediol, or a combination thereof.

In certain aspects, the NCs prepared by the systems and methods of the invention may include $CuInSe_2$, PbSe, $CuInS_2$, $Cu_2ZnSnS_4$, CPO-27-Ni, or combinations thereof. In a particular embodiment, the NC prepared by the systems and methods of the invention is $CuInSe_2$.

In other aspects, the NC precursors may be in a polar solvent or fluid, and may be in the highest temperature region due to interactions with microwaves. This will lead to activation of the NC precursors leading to nucleation and production of NCs. However, in still other aspects, the NC precursors may be in a non-polar fluid (e.g., non-polar liquid), and the microwave energy will primarily interact with any accompanying polar fluid (e.g., polar liquid), and the intimate contact between the polar and nonpolar solutions will efficiently provide heat to the non-polar fluid. This will lead to activation of the NC precursors leading to nucleation and production of NCs. Moreover, the NC precursors may be dissolved into both polar and nonpolar fluids, and the nucleation reaction will occur in the polar fluid due to the higher microwave absorptivity, and precursor species will diffuse from the lower temperature region to the higher temperature region due to a concentration gradient when the NC precursor is consumed.

Regarding the microwave reactor 3, the reactor is preferably a continuous flow reactor allowing for the fluid passageway 4 to pass through the microwave reactor 3 and, preferably, pass through a microwave zone (not pictured in FIG. 1). In the microwave zone, the fluid passageway 4, and solutions or fluids passing through the fluid passage way 4, are irradiated. The microwave reactor 3 may have a maximum power output of about 0.1 to 10 kW and, more particularly, about 3 kW. The microwave reactor 3 may also produce microwave frequencies in, for example, the microwave zone, of about 0.3-300 GHz. In another aspect, the microwave reactor 3 may produce a frequency of about 0.5-3 GHz and, more particularly about 2.48 GHz. However, the frequency provided may depend on the type of NCs produced, the chemistries used, and the design of the reaction zone as determined by the user as would be understood in the art.

Regarding the segmentation fluid source 5, the source may be disposed in fluid communication with the fluid passageway 4 and at a location between the NC precursor source 2 and the microwave reactor 3. For example, the segmentation fluid source 5 may be placed at a location that is equidistant between the NC precursor source 2 and the microwave reactor 3. The segmentation fluid source 5 provides a segmentation fluid that is immiscible with the NC precursor solution. Thus, by providing a segmentation fluid from the segmentation fluid source 5, the NC precursor solution flowing through the fluid passageway 4 may be segmented or divided, as necessary.

Several approaches can be used for forming segmented fluid flow and are encompassed within the invention. For example: (1) externally induced segmented flow (a) input of inert gas, (b) input of immiscible liquid (which can have low or high microwave susceptibility; and (2) internally induced segmented flow resulting in formation of segmented flow through outgassing of solution and/or formation of segmented flow through gas given off from reaction.

The segmentation fluid source 5 may include a valve 5A, a segmentation fluid pump 5B, and/or a segmentation fluid container 5C. The valve 5A may include any means of inserting or injecting the segmentation fluid into the fluid passageway 4 as would be understood in the art. For example, the valve 5A may include a capillary within a tube, a tee junction, or through flow focusing. However, in particular, the valve 5A includes a tee junction that allows for segmentation fluid to be inserted or injected into the fluid passageway 4. The segmentation fluid container 5C may be any container that can be configured to hold or contain a segmentation fluid. For example, the segmentation fluid container 5C may be a Tedlar bag. The segmentation fluid may include a gas, a liquid, or a combination thereof. The segmentation fluid of the invention includes those fluids that are immiscible with the NC precursor solution. For example, the segmentation fluid may be a gas, such as argon. Additionally, the segmentation fluid may be a liquid, such as a liquid comprising a nonpolar solvent that is immiscible with the NC precursor solution when the NC precursor solution comprises a polar solvent. By providing the segmentation fluid to the fluid passageway 4, the NC precursor solution is segmented or divided to produce segmented flow.

For example, segmented flow may be achieved by using two immiscible liquids. A common property that is used to define immiscible liquids is the solution polarity, where polar liquids (e.g., water) do not become a homogeneous solution with non-polar liquids (e.g., oil). Depending on the properties of the liquids, the relative flow rates of each liquid, and the physical means of mixing the two liquids, it is possible to form full segmented flow with slugs of the two solutions where both are in contact with the walls of the tubing, or bubble/drop flow where the first liquid forms liquid bubbles/drops which are carried in the second liquid. This process may be taken to an extreme where mixing may result in an emulsion, which includes very small bubbles/droplets of one liquid in another. Bubbles/droplets of the dispersed phase are produced by the fluid-fluid interfacial tension, and the flow generated shear force. Potential modalities of delivering the liquid-liquid segmented flow include, as stated above, a capillary within a tube, a tee junction, or through flow focusing. Benefits of segmented flow using two immiscible liquids include preferential microwave heating of the polar liquid, as opposed to the non-polar liquid, and the possibility of using segmented flow while performing reactions under pressure.

The segmentation fluid pump 5B may be any pump that will allow for drawing or pumping segmentation fluid from the segmentation fluid container 5C through the valve 5A into the fluid passageway 4. For example, the pump may be a peristaltic or diaphragm pump. Although FIG. 1 provides an arrangement of the pump 5B as disposed between the valve 5A and the container 5C, it is within the scope of the invention that the pump may be provided to force the segmentation fluid out of the container 5C and through the valve 5A, and thus need not be placed between the valve 5A and the container 5C. Additionally, in certain aspects of the invention, the segmentation fluid pump 5B may be omitted. Indeed, the segmentation fluid may be drawn from the container 5C by a vacuum created from the flow of precursor solution through the fluid passage way 4 or the container may be pressurized, for example.

Additionally, where a first precursor source 2A and second precursor source 2B is used, the first and second precursor solutions flowing therefrom to the fluid passageway 4 may be mixed before entering the fluid passageway 4 via a mixer 6. The mixer 6 may include a tee junction or, for example, a μ T-mixer.

The system 1 may also include a growth chamber 7 that is in fluid communication with the microwave reactor 3 through the fluid passageway 4. Indeed, the growth chamber 7 may include a coil of tubing through which the product of the microwave reactor 3 passes after being irradiated in the microwave zone of the microwave reactor 3. The growth chamber 7 may include a water bath, oil bath, or a fluidized sand bed, for example. For an oil bath, the coil of tubing rests in the oil bath, which may be heated, as necessary. In the invention, the length of the coil of tubing, as well as the flow rate therethrough may be modified or adjusted to allow for the production and growth of NCs.

Certain features of the invention may be connected by tubing 8, as necessary, to provide for fluid communication. For example, the first and/or second NC precursor sources may be connected to the mixer 6 via tubing 8. Moreover, the valve 5A, pump 5B, and/or container 5C may also be interconnected by tubing 8. Tubing 8 may be Tygon and/or PTFE tubing. Moreover, the fluid passageway 4 may also include Tygon and/or PTFE tubing.

The invention also includes a method for synthesizing NCs using the system described above. In an exemplary method, an NC precursor solution is prepared at an NC precursor source 2. The NC precursor solution may then be mixed in a mixer 6 and directed into a fluid passageway 4. Along the fluid passageway 4, the NC precursor solution may flow through or passed the segmentation fluid source 5, which inserts or injects a segmentation fluid into the fluid passageway 4 thereby segmenting or dividing the NC precursor solution into a continuous stream of NC precursor solution segments. Indeed, the segmentation fluid is immiscible with the NC precursor solution. As set forth above, the segmentation fluid may be a gas, liquid, or a combination thereof.

The segmented NC precursor solution then continuously flows through a microwave reactor 3 or, more specifically, the microwave zone of the microwave reactor 3 wherein the segmented NC precursor solution is irradiated. Following irradiation, nucleation occurs within the segmented NC precursor solution which leads to the formation of NCs. In certain aspects, the segmented NC precursor solution may be irradiated in the microwave zone and have a residence time of about 0.1 to 10 seconds, or 0.1 to 100 seconds or, preferably, about 5 seconds. Additionally, the microwave zone of the microwave reactor may heat the segmented NC precursor solution at a temperature of about 25 to 250° C. In another aspect, the temperature of the microwave zone may be about 50° C. to 200° C. or, preferably, about 180° C.

Additionally, after irradiation in the microwave reactor 3, the segmented NC precursor solution may proceed into a growth chamber 7, which allows for growth of the NCs in a growth zone. Solution passing through the growth zone may have a residence time of about 5 to 30 minutes or, preferably, about 20 minutes. Moreover, the growth zone may have a temperature of about 50 to 250° C. or, preferably, about 210° C. In the growth chamber 7, the NCs may grow and then be recovered and isolated.

Figure 2:
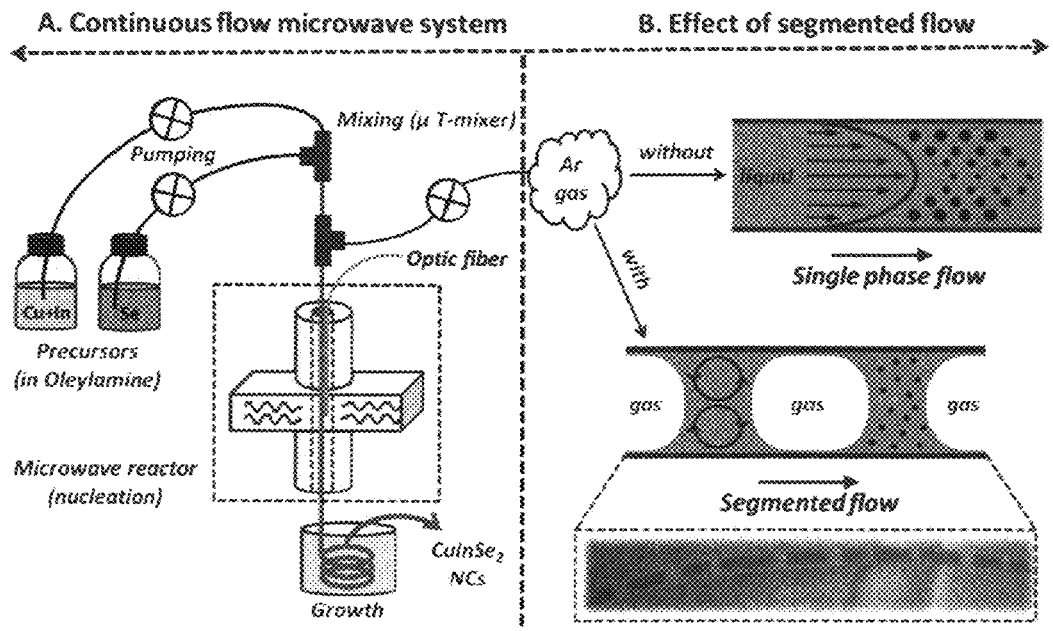
FIG. 2 illustrates both an exemplary continuous flow microwave system (A) and the effect of segmented flow in a passageway or tubing (B)

In a specific embodiment of the present invention, we introduce a continuous synthesis of colloidal NCs using a microwave-assisted reactor for the first time (FIG. 2). The use of this continuous flow microwave reactor allows for finely tuned synthesis parameters to achieve a high level of control over the reaction. A significant issue that limited the application of microwave heating in the continuous flow microwave reactor is the deposition of synthesized NCs on the inner tubing in the microwave reactor. This led to sparking in the reactor and microwave absorption of deposited material resulting in undesirable temperature spikes during synthesis. An exemplary segmented gas-liquid flow system of the invention developed to solve these issues is shown schematically in FIG. 2. The segmented flow also provides a recirculation motion in the liquid layer to enhance mixing and improve uniformity of NCs synthesized in the reactor.

In addition to solving the issue of material deposition, the segmented flow provided significant improvement in reaction uniformity. In single-phase laminar flow, a parabolic velocity profile exists causing NCs near the tubing wall to spend a longer time in the tubing than those in the center, leading to a large distribution of residence times. On the contrary, segmentation introduces recirculation (as shown in FIG. 2) within the liquid bringing synthesized NCs from the tubing wall to the center, which facilitates rapid mixing and eliminates the effect of dispersion in residence times. It also more rapidly consumes the available precursors in solution, allowing for better size control and smaller size distributions. Here, a segmented flow may be utilized for the ternary $CuInSe_2$ NC synthesis in a continuous microwave system of the invention to eliminate issues with reactor wall fouling and improve the overall reaction uniformity.

Relating to other aspects of the invention, inorganic semiconductor quantum dots (QDs) have been the subject of fundamental and applied academic research for the past 30 years, but only recently have these materials been utilized in consumer products. Display manufacturers have recently incorporated QDs into their displays to expand the color gamut and improve efficiency. White light-emitting diodes (LEDs) containing a QD downconversion film are now available commercially that have improved color quality compared to bulk phosphors. Now that QDs are being produced on an industrial scale it is important to improve the scalability of QD synthesis and to develop more environmentally benign QD materials for use in consumer products.

The hot-injection method of QD synthesis has allowed researchers to control the particle size distribution which is essential for getting QD solutions with the narrow PL spectrum desired for application in LEDs. This method involves the injection of a precursor into the reaction vessel at high temperature to quickly nucleate QDs which then begin the growth phase. This method is very effective on a scale of about 100 mL where the injection can be done in under a second and the reagents can mix quickly. On a larger scale the injection process is slower causing a temporal overlap of nucleation and growth leading to a broad particle size distribution. Another method called the non-injection or heat-up method where all reagents are mixed and then the reaction vessel is quickly heated to the critical temperature for nucleation of nanocrystals. The heat-up method suffers from a temperature gradient between the hot walls of the reactor and the solution in the center that becomes more of a problem for larger reactor volumes. Now that QDs have entered consumer products, more scalable synthetic techniques are desired.

Continuous flow reactors (CFRs), such as those described herein, provide alternatives to batch reactors for the synthesis of nanocrystals where reagents are pumped through heating zones for nucleation and growth of QDs. CFRs facilitate experimentation on a very small scale and simple scale up by running the CFR for longer times or with multiple CFRs in parallel. Temperature gradients can be minimized through the use of small-diameter tubing, and mixing can be improved by using segmented flow. Microwave heating allows for rapid, direct, volumetric heating of precursors with no warm-up time. Microwave assisted continuous flow reactors (MWCFRs) have been used to synthesize PbSe, $CuInSe_2$, and $CuInS_2$ QDs with good control over particle size distribution.

As QDs enter more consumer applications toxicity becomes a major concern. The most studied and highest performing visible light emitting QDs are composed of cadmium, which has been shown to have adverse effects on humans and the environment. The most common visible light emitting QDs that do not include cadmium are InP and $CuInS_2$ (CIS). CIS has the advantage of being a ternary material which allows for tuning the optical properties by changing the ratio of Cu and In atoms in the lattice. Cu poor CIS QDs have been shown to have increased photoluminescence quantum yield (PLQY) and blue shifted PL compared to stoichiometric CIS. The chalcopyrite crystal phase of CIS is similar to the ZnS crystal structure with Cu and In atoms replacing the Zn. The similarity between the CIS and ZnS allows for Zn to be alloyed into the lattice, creating a quaternary material, and a ZnS shell can be grown on the CIS surface due to the small lattice mismatch between the two materials.

As exemplary demonstrations of the foregoing inventions, several different nanocrystal containing materials were developed using the systems and methods of the invention. For example, copper indium diselenide ($CuInSe_2$) NCs were used as a model system. This material is particularly regarded as a potential candidate for next generation photovoltaic applications. Several results are reported in the literature for the synthesis of $CuInSe_2$ by microwave heating in batch reactors, but all syntheses resulted in unstable solutions and poor uniformity in size, shape and composition [Inorg. Chem., 2003, 42, 7148; J. Am. Ceram. Soc., 2010, 93, 1879; J. Nanosci. Nanotechnol., 2010, 10, 303; Chem. Mater., 2010, 22, 4185; Energy Environ. Sci., 2012, 5, 7539; Green Chem., 2010, 12, 1248]. The results discussed herein demonstrate use of the continuous flow microwave-assisted reactor for synthesis of CuInSe$_2$ NCs with excellent control over these properties.

In addition to the CuInSe$_2$ NCs, other nanocrystal and nanoparticle embodiments have been developed including PbSe NCs, CuInS$_2$ NCs, CPO-27-Ni NCs, and Cu$_2$ZnSnS$_4$ (CZTS) NCs.

The following examples are provided to describe the invention in further detail. These examples are provided for illustrative purposes only and are not intended to limit the invention in any way.

EXAMPLES

Example 1

Preparation of CuInSe$_2$Nanocrystals Via Continuous-Flow Microwave Assisted Reactor Chemicals.

Copper(I) chloride (CuCl, >90%), indium(III) chloride (InCl$_3$, 99.99%), selenium powder (Se, 99.5%) were purchased from Alfa Aesar. Technical grade oleylamine (OLA, >70%) and anhydrous toluene (>99.5%) were delivered from Sigma-Aldrich and ACS grade of ethanol (>99.5%) from Macron chemicals. All chemicals were used as purchased without further purification.

Preparation of Precursors.

Two Media Storage Bottles (100 mL, KIMAX) with two holes were placed on individual hot plates; one hole was connected to a vacuum or purge line, and a thermocouple was inserted through the other hole to measure the temperature. A solution consisting of CuCl (1.32 mmol), InCl$_3$ (1.32 mmol), and OLA (120 mL) in the first bottle was stirred under vacuum at 80° C. for 60 min, then purged with Ar gas (99.9999%) at 130° C. for 60 min while stirring. This solution was marked solution A. Meanwhile, Se (2.64 mmol) was added to a 40 mL of OLA in a second bottle and stirred under vacuum at 80° C. for 60 min, then purged with Ar gas (99.9999%) at 130° C. for 180 min. This solution was marked solution B.

Synthesis.

CuInSe$_2$ NCs were synthesized by a continuous flow microwave system with 3 kW maximum output power (shown in FIG. 2). In a typical synthesis, each solution was initially pumped using a peristaltic pump (REGLO Digital, Ismatec) into the Tygon tubing (i.d.: 1.52 mm, IDEX) at a flow rate of 0.6 mL/min for solution A and 0.2 mL/min for solution B. Both precursors were connected to Ar gas via a Tedlar bag during pumping in order to maintain an inert environment. The solutions were mixed in a PEEK Tee (i.d.: 0.51 mm, IDEX) before entering microwave reactor. In case of segmented flow, Ar gas of 0.2 mL/min was supplied continuously between the micro T-mixer and microwave zone (FIG. 2). The temperature of the microwave zone was controlled by adjusting reflected power and was measured using an optic fiber sensor (Neoptix). PTFE tubing (o.d.: 3.18 mm, i.d.: 1.59 mm, wall: 0.79 mm) was utilized for the microwave zone resulting in a 5 second residence time. Subsequently, the reaction was carried out in an oil bath maintained at 210° C. The sample was collected in a 30 mL glass vial for 10 min. 10 mL of ethanol was added to precipitate the NCs followed by centrifuging at 7,000 rpm for 10 min. The supernatant was discarded, and 10 mL of toluene and 5 mL of ethanol were added to flocculate the NCs followed by an additional centrifuging at 7,000 rpm for 10 min. The supernatant was decanted, and the final product was re-dispersed in 10 mL of toluene for further characterization. The different reaction conditions used in the synthesis of CuInSe$_2$ NCs are summarized in Table 1.

TABLE 1

Experimental conditions used in this work and measured Cu/In/Se compositions.

| Flow | Temperature (° C.)[a] | Residence time (min)[b] | Precursor composition (atomic % Cu:In:Se) | Product composition (atomic % Cu:In:Se)[c] | Bandgap (eV)[d] |
|---|---|---|---|---|---|
| Single | 25[e] | 20 | 1:1:2 | 1.00:0.21:1.25 | |
|  | 150 | 20 | 1:1:2 | 1.00:0.23:1.17 | |
|  | 180 | 20 | 1:1:2 | 1.00:0.49:1.70 | |
| Segment | 180 | 20 | 1:1:2 | 1.00:0.97:2.22 | 1.15 |
|  | 180 | 20 | 1:1:1 | 1.00:1.01:2.26 | 1.09 |
|  | 180 | 10 | 1:1:1 | 1.00:0.15:1.08 | 2.15 |

[a]Temperatures at microwave zone (temperature measurements have an error of ca. ± 1.5° C.),
[b]Residence times at growth zone maintained at 210° C.
[c]Compositions measured by EDS (EDS spectra were collected from 4 randomly selected areas on a Si substrate and the average compositions were calculated).
[d]Optical band-gaps were determined by extrapolating the linear region of a plot of the squared absorbance versus the photon energy.
[e]Without microwave heating (i.e., heating bath only).

Characterization.

The crystalline phases were identified by X-ray diffraction (D8 Discover, Bruker) operating at 40 kV and a current of 40 mA with Cu Kα 1 radiation (0.154 nm) in the 2θ scan range from 20° to 90° with a step size of 0.05°. The ultraviolet-visible absorption spectrum was measured using a UV-Vis-NIR spectrophotometer (V-670, Jasco) in the range of 300-1500 nm. The absorption spectra were recorded using 10 mm path length quartz cuvettes. The size and morphology of the samples were observed using a high resolution transmission electron microscopy (Titan 80-300, FEI). The solution was dropped onto a carbon-coated gold grid (300 mesh, Ted Pella Inc.). Average particle sizes were determined by manually counting at least 450 particles in the micrographs. The electron diffraction pattern was obtained by Fourier transform patterns of the high resolution transmission electron microscopy images. Energy dispersive spectroscopy spectra for bulk CuInSe$_2$ NCs were also performed on an EDAX Genesis Apex system. Samples were prepared by drop-casting the toluene suspension onto a silicon substrate and dried under N$_2$ gas.

Heat Capacity Measurement of OLA.

Figure 11:
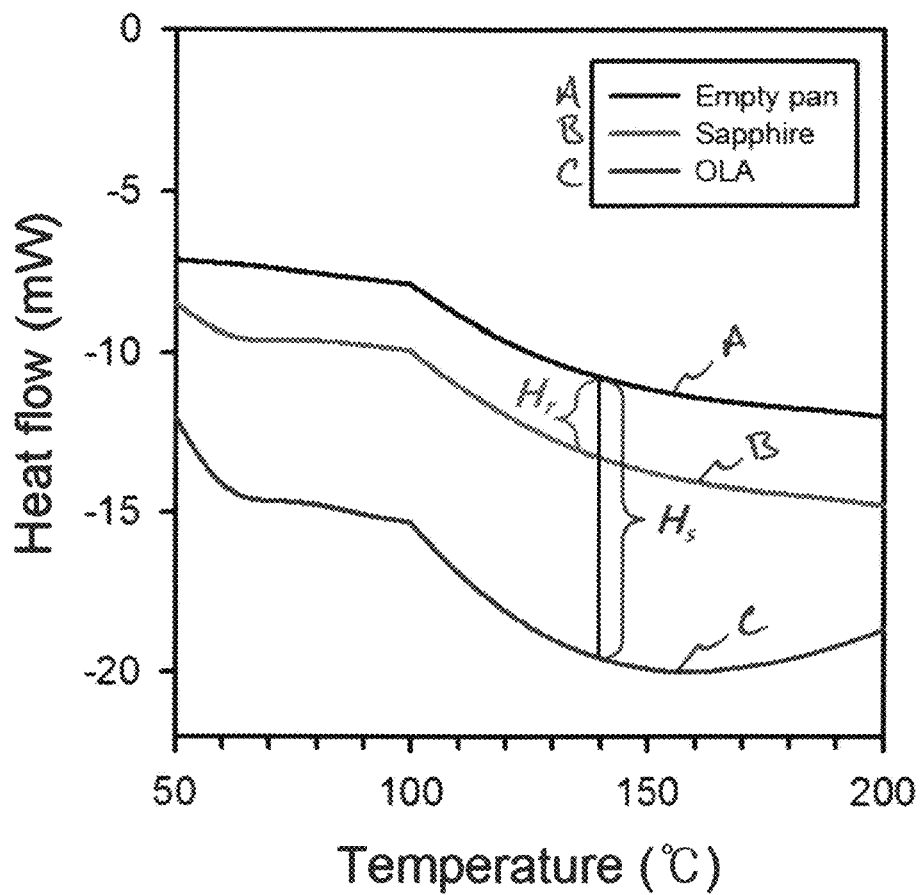
FIG. 11 graphically illustrates DSC curves of an empty pan (A), sapphire (B), and OLA (C) to determine the specific heat capacity of the OLA. $H_s$ and $H_r$ represent the heat flows for the sample and the reference material, respectively.

Using differential scanning calorimetry (DSC), it is possible to measure the specific heat capacity ($C_p$) of the OLA. The sapphire method is commonly used and provides reliable results. DSC was performed on a TA instrument SDT Q600 under a nitrogen flow. Baseline data for the empty heating chamber was collected between temperatures of 25° C. and 350° C. The energy axis was calibrated by collecting heat flow data on a sapphire sample of 17.9 mg and the commercial OLA sample of 25.6 mg was used to the calorimeter. The heat flow data were collected using a temperature ramp rate of 10° C. min$^{-1}$ in the temperature range of 50 to 350° C. and the results shown in FIG. 11. The specific heat capacity was obtained using the following equation (eq1):

$$Cps = \frac{H_s}{H_r} \cdot \frac{m_r}{m_s} \cdot Cp_r \qquad (eq1)$$

where $Cp_s$ and $Cp_r$ represent the specific heat capacities of the sample and reference material (sapphire=0.959 J g$^{-1}$ K$^{-1}$), $H_s$ and $H_r$ represent the heat flows for the sample and reference material detected by the calorimeter with respect to an empty pan, and $m_s$ and $m_r$ represent the experimental masses of the sample and reference material, respectively. With the sapphire method, the heat capacity of the OLA was estimated to be 2.352 J g$^{-1}$ K$^{-1}$.

Thermal Model.

In order to approximate the temperature of the processing fluid within the tubing where the tube's wall temperature was obtained using a fiber optic sensor, a thermal model must be developed. A heat transfer balancing model is used to simulate the fluid temperature. The heat transfer from the fluid to the tube wall is set equal to the heat transfer from the tube wall to the environment. The convection within the tube is modeled using an energy balance, and the log mean temperature difference to approximate the temperature. The heat transfer from the fluid to the tube wall ($q_{in}$) and the heat transfer from the wall to the environment ($q_{out}$) are set equal (eq2~eq4).

$$q_{in} = q_{out} \qquad (eq2)$$

$$A_{in}\overline{h}_{in}(T_m - T_s) = A_{out}\overline{h}_{out}(T_s - T_\infty) \qquad (eq3)$$

$$(T_m - T_s) = \frac{A_{out}\overline{h}_{out}(T_s - T_\infty)}{A_{in}\overline{h}_{in}} \qquad (eq4)$$

where, A is the surface area of either the internal ($A_{in}$, 0.224×10$^{-3}$ m$^2$) or external ($A_{out}$, 0.449×10$^{-3}$ m$^2$) tube, $\overline{h}$ is the mean convection coefficient of either the internal ($\overline{h}_{out}$) tube and T is the temperature of bulk ($T_m$, to be determined), surface ($T_s$, measured using a fiber optic sensor) and environmental ($T_\infty$, 25° C.).

The convection coefficient within the tube is given by eq5.

$$\overline{h}_{in} = \frac{\dot{m}C_p(T_{m,o} - T_{m,i})}{\pi D_l L \Delta T_{lm}} \qquad (eq5)$$

where, $\overline{h}$ is the mean convection coefficient, $\dot{m}$ is the mass flow rate (1.355×10$^{-5}$ kg s$^{-1}$), $C_p$ is the specific heat (2.352×J g$^{-1}$ K$^{-1}$), $D_i$ is the inner diameter (1.588×10$^{-3}$ m), L is the length (0.045 m), $T_{m,o}$ is the exit bulk mean temperature, $T_{m,i}$ is the inlet bulk mean temperature and $\Delta T_{lm}$ is the log mean temperature difference (49.53), and defined as below eq6.

$$\Delta T_{lm} = \frac{(T_s - T_{m,o}) - (T_s - T_{m,i})}{\ln\left(\frac{T_s - T_{m,o}}{T_s - T_{m,i}}\right)} \qquad (eq6)$$

The heat transfer from the tubing wall to the environment is modeled using free convection from a cylindrical tube. The $\overline{h}_{out}$ (25.97 W K$^{-1}$ m$^{-2}$) is approximated in the following eq7, $$\overline{h}_{out} = \frac{\overline{Nu}_D k}{D_o} \qquad (eq7)$$

where, $\overline{Nu}_D$ is the Nusselt number (2.54) for a cylindrical tube, k is the thermal conductivity (0.0313 W m K$^{-1}$) and $D_o$ is the outer diameter (3.175×10$^{-3}$ m). The $\overline{Nu}_D$ is approximated using the following empirical relationship in eq8.

$$\overline{Nu}_D = \left(0.6 + \frac{0.387\sqrt[6]{Ra_D}}{\left[\sqrt[27]{\left(1 + \sqrt[16]{\left(\frac{0.559}{Pr}\right)^9}\right)^8}\right]}\right)^2 \qquad (eq8)$$

where, $Ra_D$ is the Rayleigh number (177.153×m s$^{-2}$) (eq9) and Pr is the Prandtl number (0.697).

$$Ra_D = \frac{g\beta\rho(T_s - T_\infty)D_o^3}{\mu a} \qquad (eq9)$$

where, g is the acceleration of gravity (9.8 m s$^{-2}$), $\beta$ is the thermal expansion coefficient (2.725×10$^{-3}$ K$^{-1}$), $\rho$ is the fluid density (813 kg m$^{-3}$), $\mu$ is the viscosity (2.28×10$^{-5}$ m$^2$ s$^{-1}$) and $\alpha$ is the thermal diffusivity (3.28 m$^2$ s$^{-1}$). So putting all this together gives the following eq10, $$(T_m - T_s) = \frac{A_{out}k\left(0.6 + \frac{0.387\sqrt[6]{\frac{g\beta\rho(T_s - T_\infty)D_o^3}{\mu\alpha}}}{\sqrt[27]{\left(1 + \sqrt[16]{\left(\frac{0.559}{Pr}\right)^9}\right)^8}}\right)^2 (T_s - T_\infty)}{A_{in}\frac{\dot{m}C_p(T_{m,o} - T_{m,i})\ln\left(\frac{T_s - T_{m,o}}{T_s - T_{m,i}}\right)}{\pi L \Delta T_{lm}((T_s - T_{m,o}) - (T_s - T_{m,i}))}} \qquad (eq10)$$

These empirical relationships given by the equations above are reported to have an error of 15%, so the change in temperature has a range of plus 15% and minus 15%. Given the parameters from the above equations, including eq10, the approximate fluid bulk mean temperature may be observed as set forth in Table 2.

TABLE 2

Parameters to approximate the fluid bulk mean temperatures obtained by a heat transfer balancing model.

| $T_{in}$ (° C.)[a] | Ts (° C.)[b] | (Tm - Ts) (° C.)[c] | Tm (° C.)[d] | Tmin (° C.)[e] | $T_{max}$ (° C.)[f] |
|---|---|---|---|---|---|
| 60 | 150 | 51.0 | 201.0 | 193.4 | 208.7 |
|  | 180 | 67.0 | 247.0 | 236.9 | 256.9 |

[a]Inlet temperature of the fluid prior to microwave heating;
[b]Temperatures measured using an optic fiber sensor;
[c]Changes in temperature calculated using eq10;
[d]Approximated temperatures of the fluid bulk; and Temperatures of a range of
[e]minus 15% and
[f]plus 15%.

Results and Discussion.

Figure 3A:
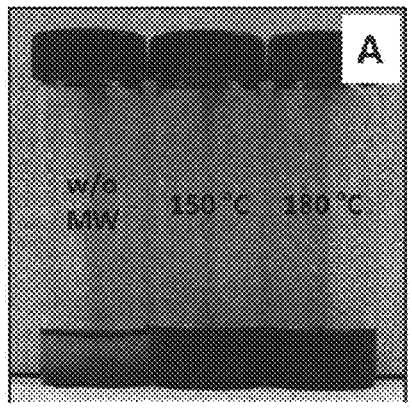
FIGS. 3A to 3E pictorially demonstrate: the effect of temperature and microwave irradiation on $CuInSe_2$ NCs after being re-dispersed in toluene (FIG. 3A); TEM images of $CuInSe_2$ NCs synthesized without microwave (FIG. 3B), microwave heating to 150° C.
Figure 3B:
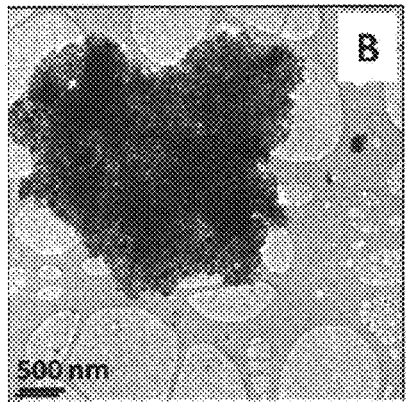
Figure 3C:
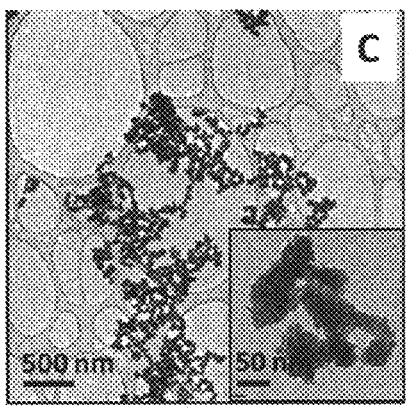
Figure 3E:
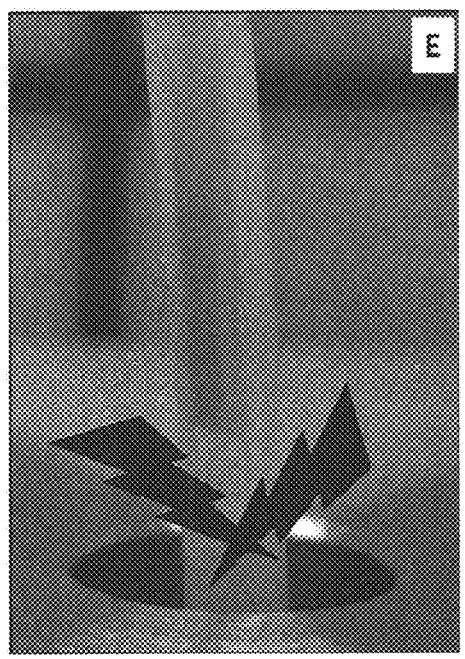
Figure 3D:
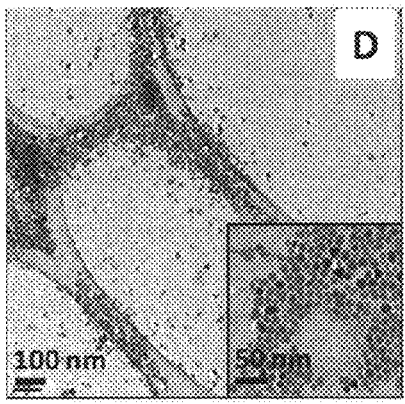

FIG. 3A shows the photographs of CuInSe$_2$ NCs synthesized at different microwave heating conditions in a single phase continuous flow microwave system. The unstable CuInSe$_2$ NCs in solution were obtained without microwave irradiation. EDS result reveals (Table 1) the indium and selenium deficiency (Cu$_{1.00}$; In$_{0.21}$; Se$_{1.25}$) indicating that the longer reaction time or higher reaction temperature is required. TEM image (FIG. 3B) also shows the aggregated CuInSe$_2$ NCs synthesized without microwave heating. On the contrary, it can be clearly seen that solution-stable CuInSe$_2$ NCs were synthesized by using microwave heating. The colors of the solutions appear darker with increasing microwave heating temperature, indicating more CuInSe$_2$ NCs are formed. FIG. 3C and FIG. 3D show the TEM images of the CuInSe$_2$ NCs synthesized by different microwave heating conditions. TEM images indicate that the CuInSe$_2$ NCs synthesized at the higher temperature (180° C.) are mono-disperse in solution with an average diameter of 18 nm and a coefficient of variation (COV) of 31.7%. It can also be seen that the CuInSe$_2$ NCs are a mixture of spherical, hexagonal, and trigonal shapes. However, deposition of synthesized CuInSe$_2$ NCs on the inner wall of PTFE tubing after 20 min of heating time resulted in sparking (FIG. 3E), indicating that some adaptation to the system is required in order to perform controllable syntheses.

Figure 4:
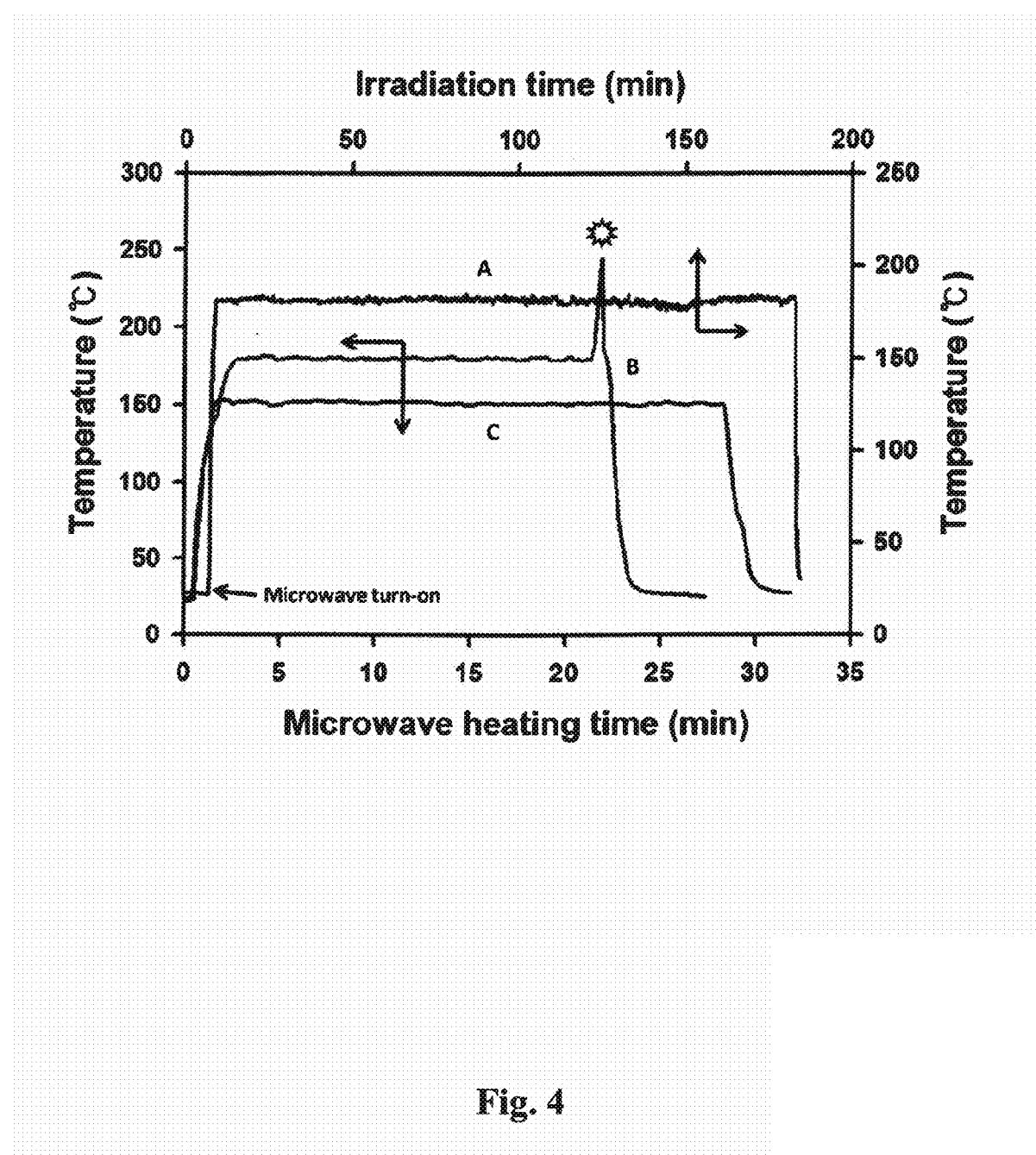
FIG. 4 graphically illustrates temperature profiles by microwave heating with single phase and segmented flow in continuous flow microwave systems where the peak indicated by the "star" is the temperature rising rapidly due to sparking; wherein FIG. 4 compares (A) segmented flow (180° C.), (B) single phase flow (180° C.), and (C) single phase flow (150° C.).

The temperature profiles of single phase flow and segmented flow during microwave heating in the continuous flow microwave system are shown in FIG. 4. The temperature was rapidly ramped to the set point (150° C. and 180° C.) in a few seconds. However, microwave heating at 180° C. after 20 min using a single phase flow led to extremely high temperature due to sparking as seen in FIG. 4 (indicated by the "star"). To solve this sparking issue, Ar gas was supplied continuously between the micro T-mixer and microwave zone leading to gas-liquid segmented flow in tubing, as shown in FIG. 2. The segmented flow approach solved the sparking problem by preventing fouling on the reactor walls. As a result, the temperature (180° C.) was maintained for 3 h with high precision (±1.5° C.) by the continuous supply of Ar gas.

Figure 5:
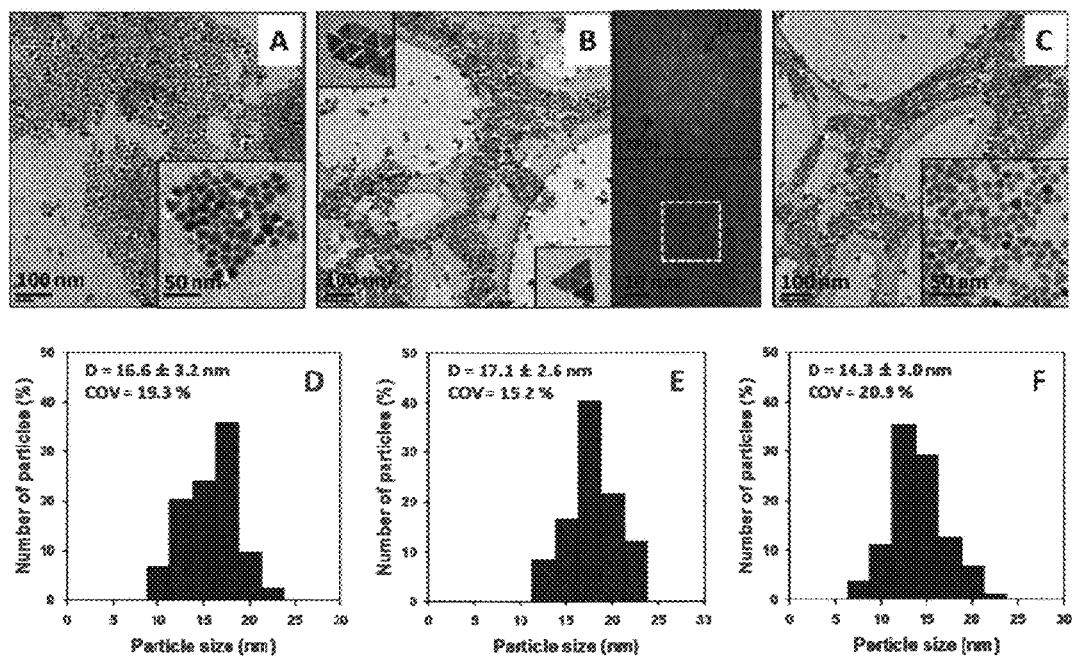
FIG. 5 illustrates TEM images (A to C) and particle size distributions (D to F) for $CuInSe_2$ NCs prepared by the present invention; specifically, (A) provides Cu/In/Se=1:1:2 with a growth zone residence time of 20 mins; (B) provides Cu/In/Se=1:1:1 with a growth zone residence time of 20 mins; and (C) provides Cu/In/Se=1:1:1 with a growth zone residence time of 10 mins.

The size and morphology of CuInSe$_2$ NCs synthesized by a continuous flow microwave system with segmented flowing of Ar gas was observed by low and high-resolution TEM. FIG. 5 shows the TEM images of CuInSe$_2$ NCs synthesized with microwave heating at 180° C. All CuInSe$_2$ NCs synthesized with segmented flow yielded highly stable solutions with very narrow size distributions, as indicated in the histograms (FIGS. 5D-5F). The CuInSe$_2$ NCs synthesized at 210° C. for 20 min from 1:1:2 ratios of Cu:In:Se precursors were particularly monodisperse (average diameter of 16.6±3.2 nm and COV of 19.3%) and had irregular shapes (trigonal, hexagonal, and spherical) as shown in FIG. 5A.

FIG. 5B shows the TEM image of the CuInSe$_2$ NCs synthesized by segmented flow microwave heating at 180° C. for 20 min with 1:1:1 ratios of Cu:In:Se precursors. These CuInSe$_2$ NCs exhibited the nearly a perfect trigonal shape particles with an average diameter of 17.1±2.6 nm and a COV of 15.2% indicating a very narrow size distribution. The Fourier transform image (inset of FIG. 5B) showed very well formed single crystals indexed to chalcopyrite (tetragonal) CuInSe$_2$ phase. The reaction time at 210° C. is changed to 10 min, and result is shown in FIG. 5C. TEM image indicates that synthesized CuInSe$_2$ NCs have an average particle size of 14.3±3.0 nm.

Figure 6:
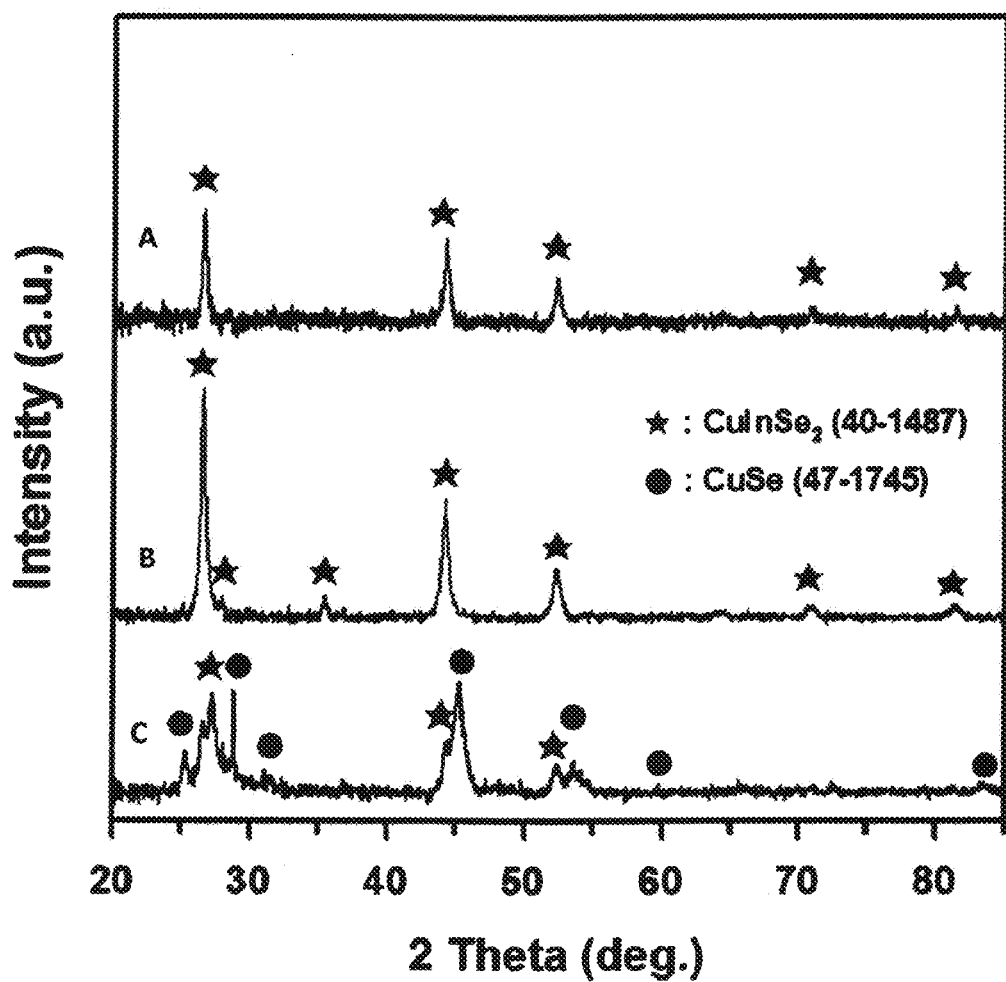
FIG. 6 graphically demonstrates x-ray diffraction (XRD) patterns of $CuInSe_2$ NCs synthesized at different reaction conditions with segmented flow microwave heating; wherein (A) is Cu/In/Se=1:1:2, with a growth zone residence time of 20 mins; (B) is Cu/In/Se=1:1:1, with a growth zone residence time of 20 mins; and (C) is Cu/In/Se=1:1:1 having a growth zone residence time of 10 mins.

The crystal structures of the CuInSe$_2$ NCs synthesized with segmented flow microwave heating at 180° C. were investigated using XRD (FIG. 6). The XRD patterns of the both CuInSe$_2$ NCs synthesized for 20 min with 1:1:2 and 1:1:1 ratios of Cu:In:Se precursors show the chalcopyrite (tetragonal) phase of CuInSe$_2$ (JCPDS No. 40-1487) with an intense peak at 2θ=26.6° oriented along the (112) direction. The other distinct reflection peaks with 2θ values of 44.2°, 52.4°, and 70.8° are indexed to (204)/(220), (312)/(116) and (316)/(332) planes of tetragonal CuInSe$_2$. In addition to these intense peaks, weaker peaks were observed at 27.8°, 30.9°, 35.5°, and 64.3° which correspond to the (103), (200), (211), (400) planes, and are unique to the chalcopyrite CuInSe$_2$ phase (FIG. 6B). EDS results reveal the CuInSe$_2$ NCs consists of Cu, In, and Se with the desired stoichiometry of 1:1:2 with a slight excess of selenium ion (Table 1). With decreasing reaction time by 10 min, the different XRD pattern of CuInSe$_2$ NCs could be indexed to the tetragonal Cu$_3$Se$_2$ phase (JCPDS No. 47-1745). The compositions of the Cu/In/Se also shows an indium and selenium deficiency which is attributed to the Cu$_3$Se$_2$ phase.

Figure 7:
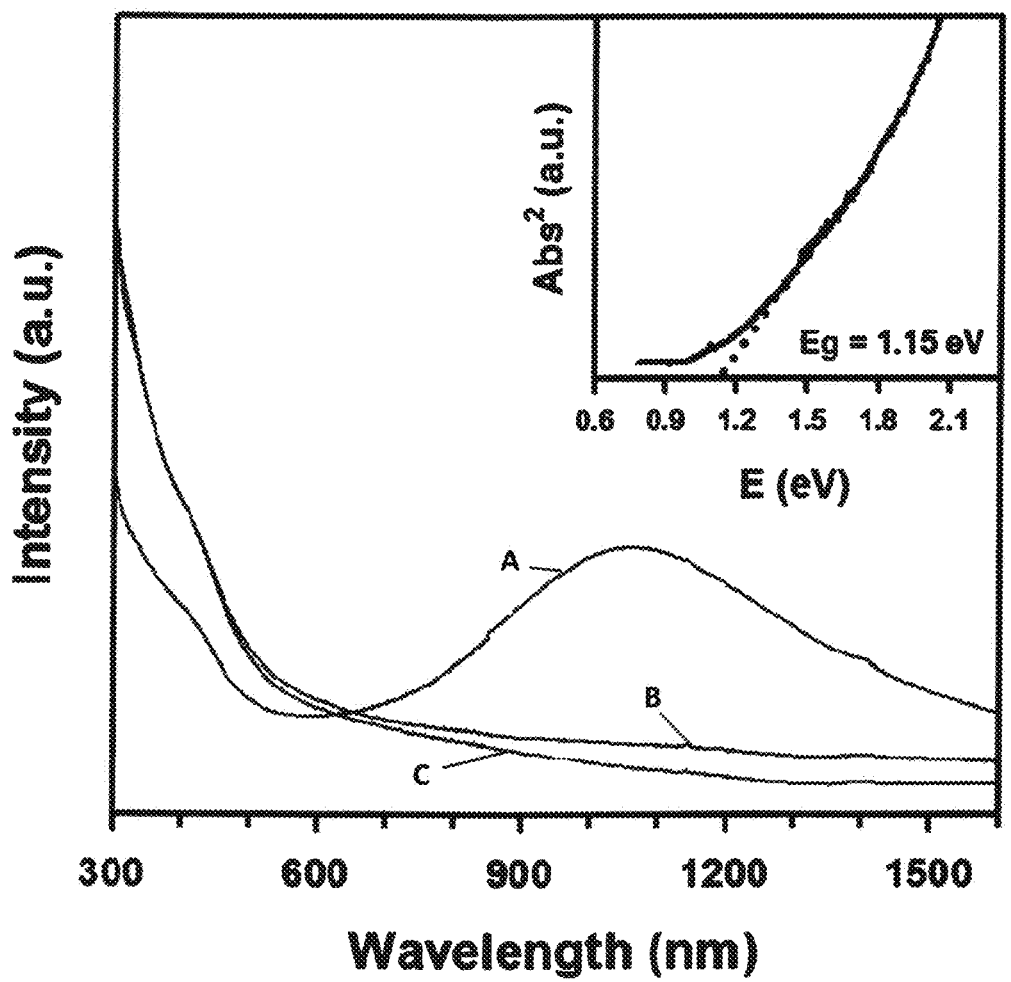
FIG. 7 graphically demonstrates UV-Vis absorption spectra of the $CuInSe_2$ NCs synthesized at different reaction conditions with segmented flow microwave heating; wherein (A) is Cu/In/Se=1:1:1, with a growth zone residence time of 10 mins; (B) is Cu/In/Se=1:1:2, with a growth zone residence time of 20 mins; and (C) is Cu/In/Se=1:1:1, with a growth zone residence time of 20 mins.

The absorption spectra of the CuInSe$_2$ NCs synthesized by segmented flow microwave heating suspended in toluene were measured using UV-Vis absorbance spectroscopy (FIG. 7). The absorption peak located at 420 nm was obtained, indicative of chalcopyrite CuInSe$_2$. The inset in FIG. 6 shows the linear extrapolation band-gap estimation method, yielding a value of 1.15 eV, which is in a good agreement with that of bulk chalcopyrite CuInSe$_2$ (1.05 eV). A broad and intense absorbance peak for the CuInSe$_2$ NCs synthesized at reaction time of 10 min was observed at 1050 nm, which is attributed to transitions involving the indirect band gap of copper selenide.

Figure 12:
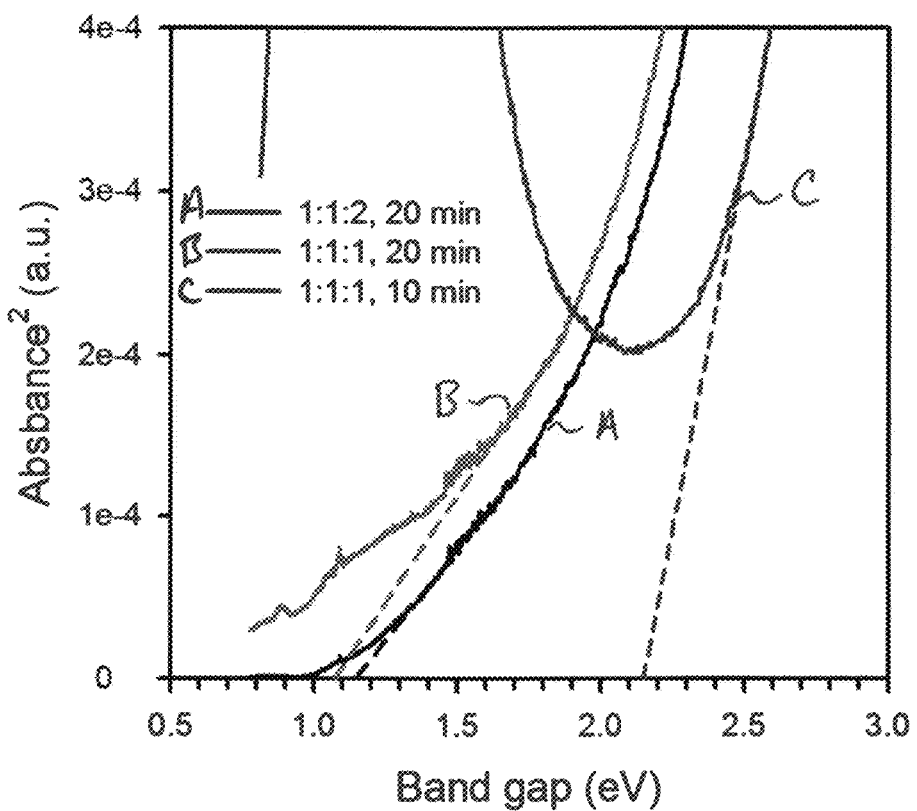
FIG. 12 graphically illustrates the optical energy gap of $CuInSe_2$ NCs synthesized at different reaction conditions with segmented flow microwave heating according to the invention of 247° C. (A) Cu/In/Se=1:1:2, growth time=20 min; (B) Cu/In/Se=1:1:1, growth time=20 min; (C) Cu/In/Se=1:1:1, growth time=10 min. For each reaction condition, the band gap was determined by extrapolating the linear region of a plot of the squared absorbance versus the photon energy. The band gap of copper selenide may not be well defined because of the wide variety of stoichiometric ratios, bulk copper selenides are typically reported to possess a direct band gap of 2.1 eV-2.4 eV. The obtained band gap values are consistent with reported values and the $CuInSe_2$ NCs synthesized at growth times of 20 min, with 1:1:1 ratios of Cu:In:Se precursors was found to be 1.09 eV, which is in a good agreement with that of bulk chalcopyrite $CuInSe_2$ (1.04 eV).

FIG. 7 demonstrates the optical absorption spectra of these NCs suspended in toluene. A broad and intense absorbance peak for the NCs synthesized at growth time of 10 min was observed at 1050 nm, which is attributed to the indirect band gap of copper selenide. This peak disappears with an increase in growth time to 20 min, indicating the conversion to CuInSe$_2$ in agreement with TEM, XRD, and EDS data. The estimated direct band gap values for each reaction condition are consistent with a decrease in copper selenide (Table 1, FIG. 12), yielding a value of 1.09 eV for 1:1:1 ratios of Cu/In/Se precursor at growth times of 20 min, which is in a good agreement with that of bulk chalcopyrite CuInSe$_2$ (1.05 eV).

Figure 8:
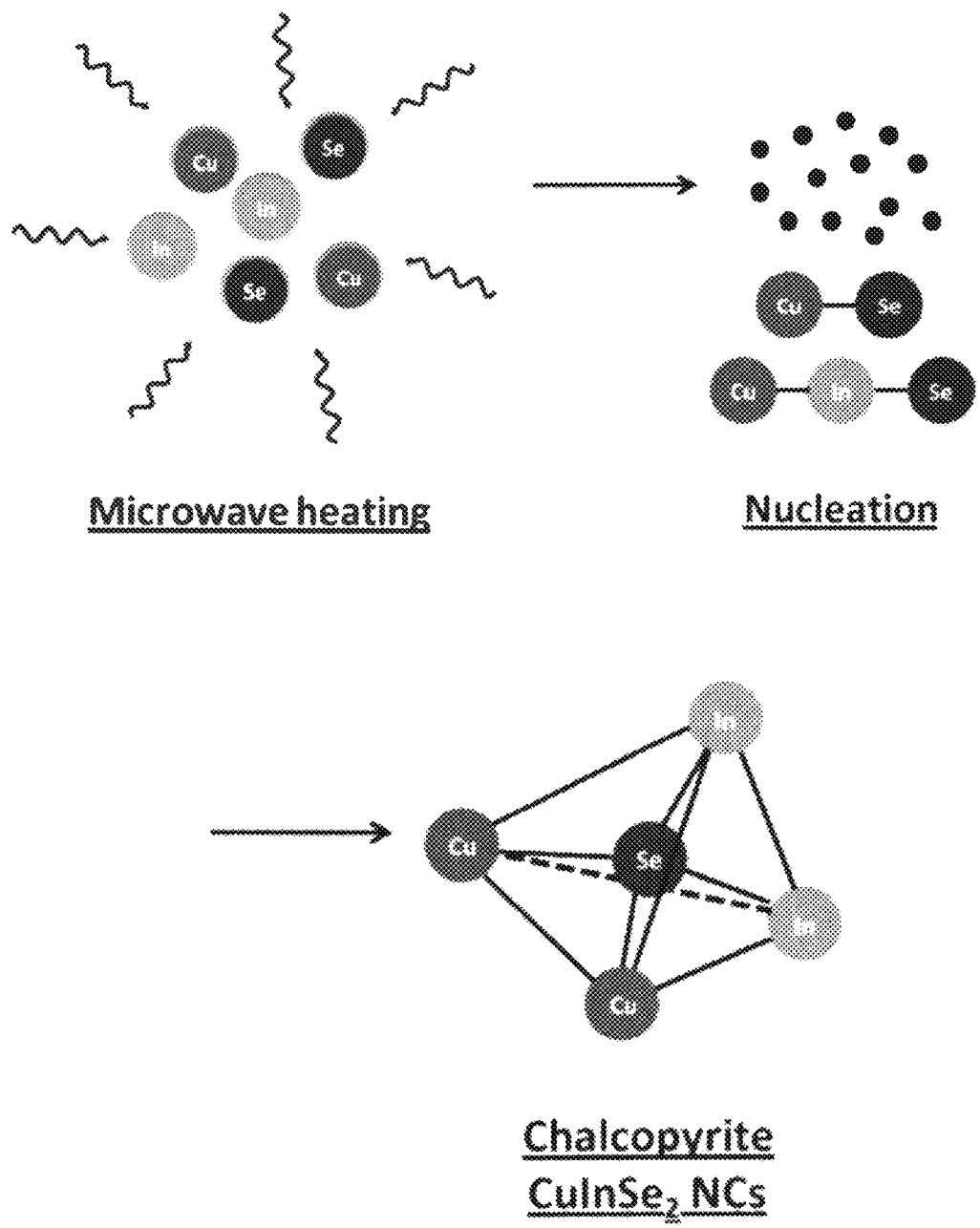
FIG. 8 schematically illustrates the synthesis of $CuInSe_2$ NCs by a continuous flow microwave-assisted reaction.

Based on the XRD and UV-Vis data, and without being limited to any one theory of the invention, we postulate that initially copper selenide intermediates (or indium/selenium deficient CuInSe$_2$ NCs) are formed, followed by their reaction with indium ions as reaction time is increased, finally resulting in chalcopyrite (tetragonal) phase CuInSe$_2$ NCs (FIG. 8).

Figure 9A:
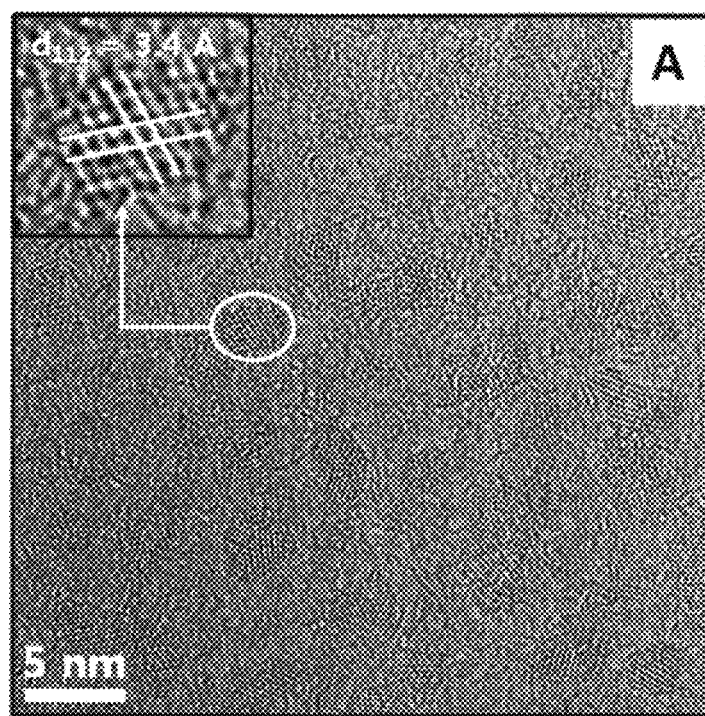
FIG. 9A pictorially demonstrates a TEM image of $CuInSe_2$ QDs with an average diameter of 2.6±0.4 nm (inset shows an HRTEM image of single QDs with lattice spacings of 0.34 nm corresponding to the (112) plane of $CuInSe_2$). EDS analysis confirms the presence of Cu, In, and Se and shows the composition to be $Cu_{1.00}In_{0.98}Se_{2.19}$).
Figure 9B:
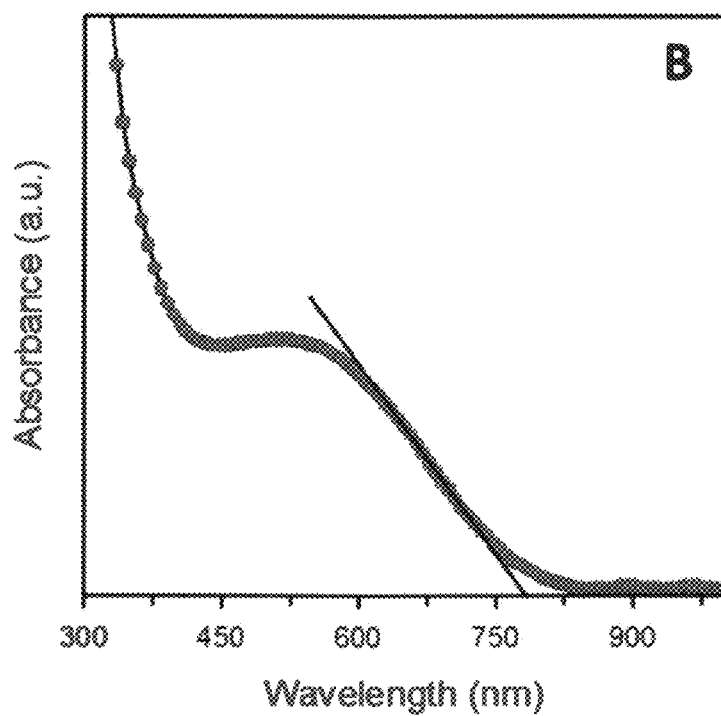
FIG. 9B graphically illustrates the absorption spectrum of the QDs synthesized using microwave heating at 247° C. for 5 s without further growth from 1:1:1 ratios of Cu/In/Se precursor. The linear extrapolation of FIG. 5B of the absorption spectrum indicates a band gap of 1.59 eV (or 780 nm).

A sample synthesized with segmented flow microwave heating to 180° C. (as measured by optic sensor) without further growth from 1:1:1 ratios of Cu/In/Se precursor was analyzed to investigate early stages of the NC reaction pathway. A TEM image (FIG. 9A) revealed the presence of NCs, and the structure determined from high-resolution TEM (HRTEM) and composition from EDS indicates NCs synthesized via 5 s of microwave heating with no further heating consists of CuInSe$_2$ quantum dots (QDs). FIG. 9B shows the optical absorbance spectrum of the OLA-caped CuInSe$_2$ QDs and was found to have a band edge at 780 nm (1.59 eV) determined at linear region of the absorption spectrum x-intercept. The band edge is blue-shifted by approximately 0.54 eV in relation to bulk CuInSe$_2$ (1.04 eV). This is due to the quantum confinement when size decreases below the Bohr exciton radius of the CuInSe$_2$ (10.6 nm), and the shift is in good agreement with that expected for QDs of this size according to DFT calculations.

The rapid synthesis of uniform, rather small diameter CuInSe$_2$ QDs with only 5 s of microwave heating is an intriguing result.

Conclusion.

We have developed a continuous microwave-assisted segmented flow reactor for high-quality NC synthesis. A key obstacle during reactions was deposition of synthesized NCs on the reactor tube wall resulting in sparking. This issue was solved by the present invention where Ar gas was introduced prior to microwave heating, resulting in segmented flow which minimized deposition of the NCs on the wall surface.

More specifically, CuInSe$_2$ QDs are formed during microwave heating consuming a fraction of dissolved precursors and are sufficiently coordinated with OLA ligands. Incorporating the heating bath following nucleation by microwave heating allows for growth of the stabilized CuInSe$_2$ QDs via diffusion of dissolved Cu, In, and Se ions and/or controlled Ostwald ripening while simultaneously nucleating CuSe, which is common to slow heating procedures using these chemistries. In contrast, using only the heating bath results in unstable (or aggregative) NCs in solutions consisting primarily of CuSe intermediates due to poor reaction uniformity from lack of distinct nucleation events. Thus, precursors subjected to microwave heating prior to the growth zone resulted in CuInSe$_2$ while those without microwave resulted primarily in CuSe intermediate. Furthermore, the reaction containing stoichoimetric precursor concentrations (Cu/In/Se=1:1:2) resulted in the ordered chalcopyrite phase. In the case of stoichiometric precursors, the reaction likely proceeds via the reaction of binary CuSe and InSe leading to the formation of sphalerite CuInSe$_2$. In the case of Se deficiency in the precursors, formation of CuInSe$_2$ is more likely to occur via reaction of CuSe with dissolved InCl$_3$ and thus leads to chalcopyrite CuInSe$_2$. This data suggests microwave nucleation plays a role in the formation of high-quality NCs and that this process may be suitable for formation of other complex multinary NC systems which are very difficult to produce with significant uniformity via batch type hot-injection.

Figure 10A:
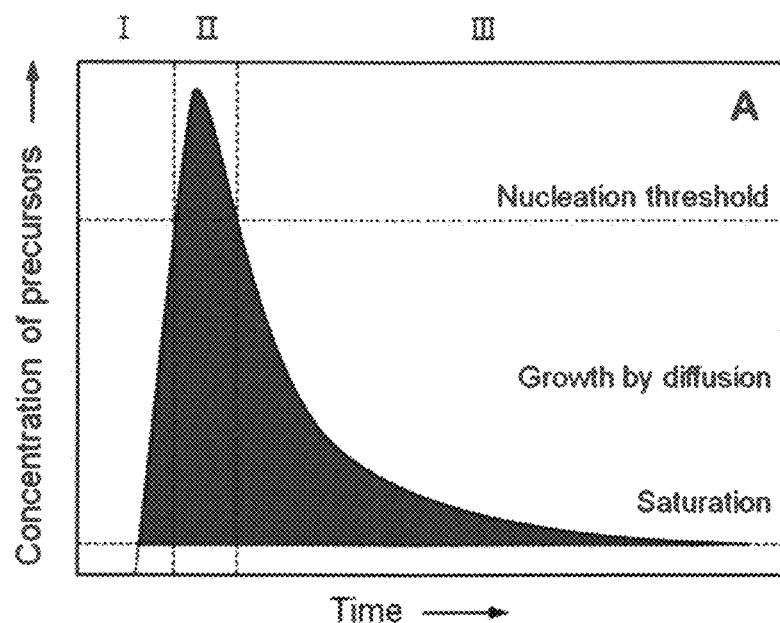
FIGS. 10A and 10B graphically illustrate free precursor concentration profiles as a function of reaction time (or distance along the reactor) showing the different stages of nucleation and growth for a typical hot-injection system (FIG. 10A) and the synthesis of high-quality NCs using the segmented flow system of the invention (FIG. 10B).

The different stages of nucleation and growth for the precise control of kinetics for NCs in the present system may be compared with the hot-injection technique shown in FIG. 10. The initial nucleation events may partially relieve the supersaturation condition, preventing nucleation of new NCs. During the final stage, slower and more controlled NC growth continues only from existing nuclei resulting in increased NC uniformity over time. As shown, the rapid hot-injection of precursors instantly raises the concentration above the critical nucleation threshold (Stage II in FIG. 10A). This supersaturation is then partially relieved by a short intense burst of nucleation, as well as a rapid temperature decrease causing the precursor concentration to fall below the critical threshold. In most cases, precipitation of NCs occurs by growth of existing nuclei during the remaining reaction time. If the growth of NCs continuous in the solution, secondary growth by Ostwald ripening can occur because some smaller NCs are consumed and eventually disappear, and thus NCs are still growing leading to large size distributions.

Figure 10B:
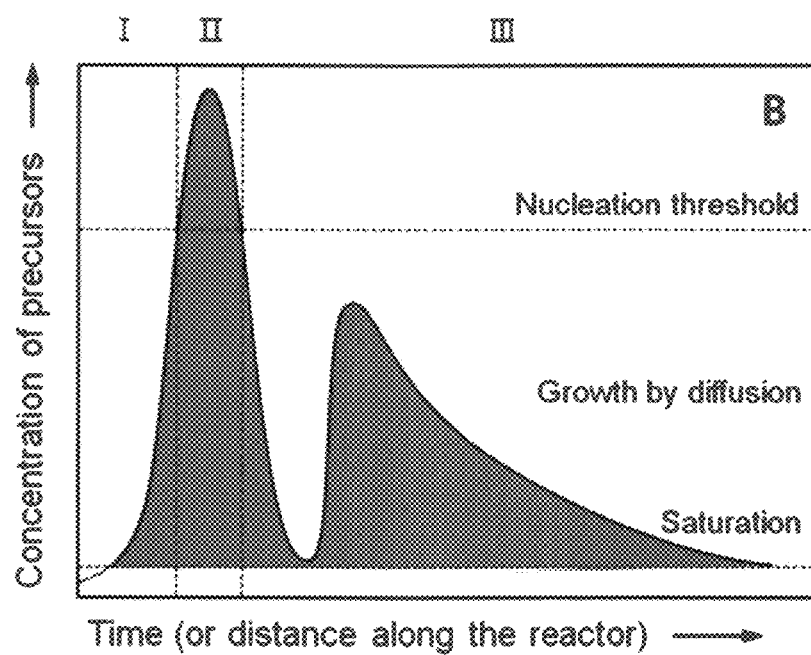

In contrast, FIG. 10B demonstrates the different concentration profile of the continuous microwave system of the invention as a function of reaction time (or distance along the reactor). Note that the initial precursors were already mixed homogenously prior to microwave heating (stage I in FIG. 10B) since the reactions could be separated into nucleation and growth zone in the continuous microwave system of the invention. The NCs are formed having a burst nucleation event in the microwave heating (stage II in FIG. 10B), diminish the temperature and concentration gradients within the reactor by uniform volumetric heating and very rapid heating rates, then the concentration of precursors quickly decreases over time until it reaches the level at which the nucleation rate is zero. After this, the system enters the growth stage (stage III in FIG. 10B), sufficient to provide the thermal activation necessary for continued growth of existing nuclei, but insufficient to allow for any appreciable nucleation to occur. Thus, nucleation and growth are successfully divided, providing the optimum conditions needed to produce monodisperse and narrow size distribution of NCs. The results presented here show that the continuous microwave system of the invention is very suitable for synthesizing high-quality NCs with good control over NCs size and can reproducibly and reliably generate large quantities of uniform NCs.

As a model system to demonstrate these concepts of the invention, we have synthesized high quality colloidal chalcopyrite CuInSe$_2$ NCs with an average diameter of 17.1 nm and COV of 15.2%. Utilization of a continuous microwave-assisted segmented flow reactor of the invention has key advantages over traditional synthetic methods enabling for high control of the sizes and shapes of CuInSe$_2$ NCs.

Example 2

Synthesis of Colloidal PbSe Nanoparticles Using a Microwave-Assisted Segmented Flow Reactor Lead selenide nanoparticles (PbSe NPs) are of considerable interest due to their large Bohr exciton radius (46 nm) and small direct bulk bandgap (0.28 eV). These properties make PbSe NPs useful for solar cells, photodetectors, and infrared emitters. The large Bohr exciton radius allows the optical properties of PbSe NPs to be tuned by controlling their size. Solution-based approaches for the synthesis of colloidal PbSe NPs include solvothermal, sonochemical, photochemical, pH induced precipitation, microwave-assisted, continuous flow, and hot injection methods. For these applications narrow PbSe NP size distributions are important, and hot injection techniques are most commonly used for synthesis of PbSe NPs.

In this study, a microwave-assisted segmented flow reactor was used to synthesize colloidal PbSe NPs. We have found that chemistries developed for hot injection methods can be readily adapted to the microwave-assisted segmented flow reactor and that the NP size could be controlled by varying the microwave nucleation temperature ($T_{\mu W}$).

Materials and Methods.

Lead(II) oxide (PbO powder, >90%), tri-n-octylphosphine (TOP, 90%), and selenium powder (Se, 325 mesh, 99.5%) were obtained from Alfa Aesar, Oleic acid (OA, 90%), toluene, and 1-octadecene (ODE, 90%) were obtained from Marcon, and acetonitrile was obtained from JT Baker. All chemicals were used without further purification.

Two separate precursor solutions were formed in a nitrogen glovebox. The first contained 0.20 M PbO and 0.50 M OA in ODE. The second contained 0.40 M Se and 0.60 M TOP in ODE. The two solutions were stirred for 120 min at 150° C. The precursors were transferred from the glovebox to the reactor in sealed sample containers. The precursors were held at 150° C. for 20 min under vacuum, then reduced to 90° C. while Ar gas was bubbled through the solution for an additional 20 min.

A peristaltic pump delivered the two precursors at a rate of 0.30 mL/min into a polyether ether ketone (PEEK) micro T-mixer. A second PEEK microT-mixer was connected downstream from the first to obtain segmented flow using Ar gas with a constant flow rate of 0.15 mL/min. Initially, the segmented solution flowed at a rate of 0.75 mL/min, however, the flow rate was not constant through the entire volume since the Ar gas expands with decreased pressure and increased temperature. High temperature polytetrafluoroethylene (PTFE) tubing (1.6 mm inner diameter) was used for the nucleation, growth, and quench zones of the reactor.

The segmented solution entered the nucleation zone through an aluminum chimney and was irradiated over a 4 cm length using a microwave reactor (Sairem model PCCMWR340PVMR1PE GMP 30 k; 3 kW; 2.45 GHz) with a residence time of ~6 s. A pyrex tube was sued to center the top and bottom of the PTFE tube in the microwave reactor. A fiber optic probe (Neoptix) was attached to the outside of the PTFE tube PTFE tape and was positioned in the center of the microwave region. The $T_{\mu W}$ was controlled by setting the microwave power between 270 and 360 W and then adjusting the reflector to achieve a maximum temperature. After exiting the microwave the segmented solution entered the growth zone which consisted of 350 cm of coiled tubing submerged in a 140° C. oil bath, resulting in a growth zone residence time of ~9 min. Upon exiting the oil bath the solution entered the quench zone where the tubing was cooled by ambient air over the last 10 cm prior to collection in a glass vial. During the PbSe NP synthesis the reactor was run continuously for 3.5-6 h. For each sample the $T_{\mu W}$ was adjusted and allowed to stabilize prior to collecting the product for 10 min. Addition of methanol followed by centrifugation was used to precipitate the PbSe NPs, which were resuspended in toluene. This process was repeated a minimum of three times prior to analysis, and NPs remained stable in solution for several weeks.

Compositions were determined using energy dispersive X-ray spectroscopy (EDS) with a FEI Quanta 3D (30 kV beam energy). Crystal structures were determined using X-ray diffraction (XRD) with a Bruker D8 Discover diffractometer (Cu Kα radiation). Size and crystal structures were determined using a FEI Titan FEG transmission electron microscope (TEM) (200 kV beam energy), where the TEM images were analyzed with ImageJ software. A minimum of 300 NPs were counted and sized for each condition to find an average diameter ($\bar{X}$) and standard deviation (σ). To determine if the mean nanoparticle size obtained for different experimental conditions was statistically different we performed an analysis of variance (ANOVA).

Results and Discussion.

Figure 13:
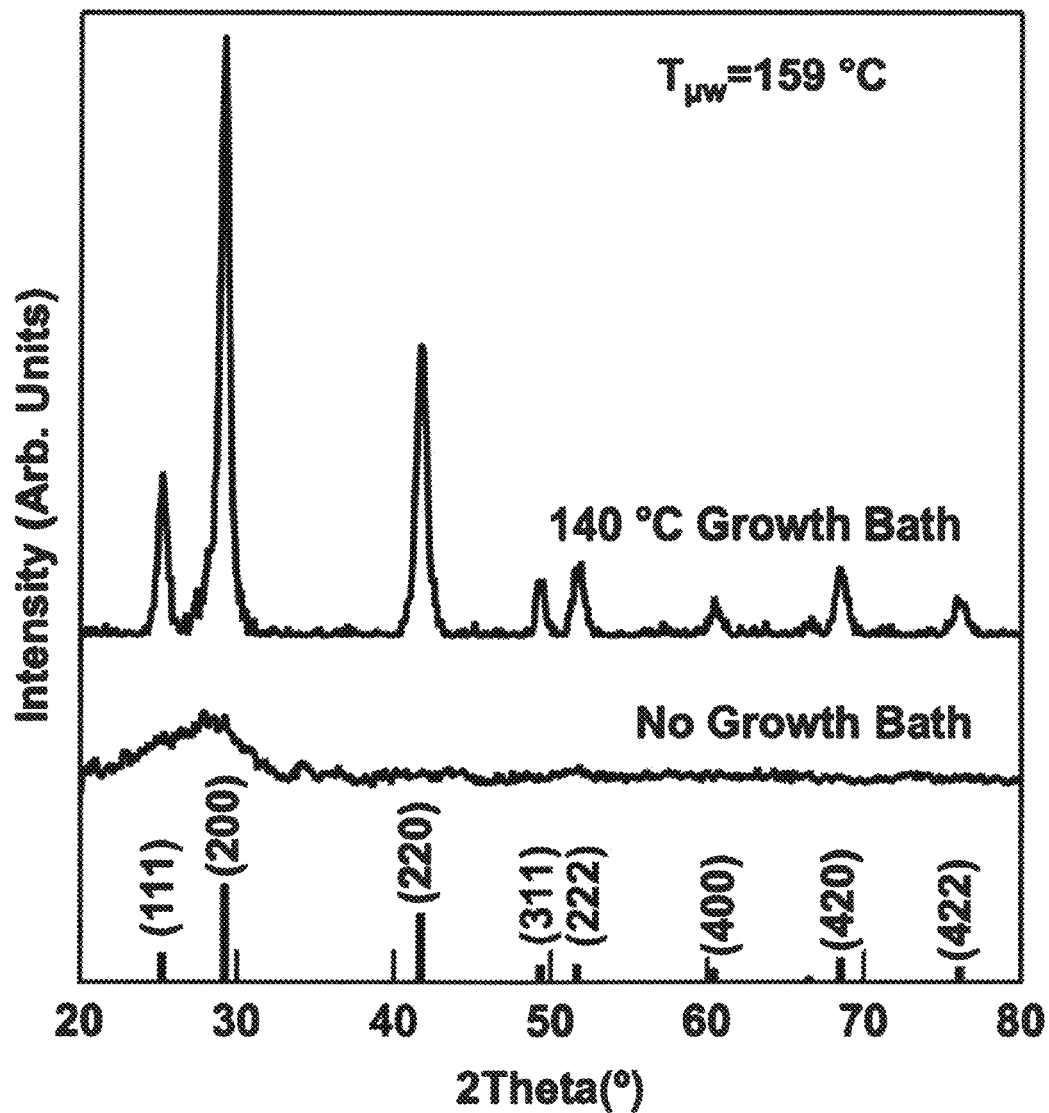
FIG. 13 graphically illustrates XRD patterns for PbSe NP material synthesized with a $T_{\mu W}$ of 159° C. with (upper) and without (lower) a growth temperature of 140° C.

A series of reactions were performed with $T_{\mu W}$ varying between 124, 142, and 159° C. followed by a constant growth zone temperature (140° C.). Dropcast films of PbSe NPs were characterized using XRD and a typical diffraction pattern is shown in FIG. 13. The XRD patterns have eight main diffraction peaks at 2θ=25.2°, 29.1°, 41.7°, 49.3°, 51.7°, 60.4°, 68.5°, and 76.1°, which correspond to the (111), (200), (220), (311), (222), (400), (420), and (422) planes, respectively, of PbSe clausthalite (JCPDS 00-006-0354) and are indicated in the bottom of the figure. No impurity peaks were observed in the XRD patterns, suggesting phase pure PbSe NPs. An XRD pattern from a sample that had a $T_{\mu W}$ of 159° C. but no growth zone is shown in FIG. 13. In this case only a broad diffraction feature is observed suggesting very small particle sizes and/or amorphous materials.

EDS was performed on dropcast films to determine the Pb:Se stoichiometry for different growth conditions. Table 3 indicates that $T_{\mu W}$, with a 140° C. growth zone, influenced the stoichiometry of the PbSe NPs, where lower $T_{\mu W}$ resulted in a slight excess of Se. However, it should be noted that the PbSe NP stoichiometries for these conditions were within the standard deviation of the desired 1:1 atomic composition. EDS obtained from a sample synthesized using a $T_{\mu W}$ of 159° C., but without the growth zone, indicated formation of Pb rich material. We were unable to obtain HR-TEM images from these samples despite through cleaning procedures due to significant carbon contamination during imaging, and possibly due to the amorphous nature of the particles as suggested by the XRD.

TABLE 3

Summary of PbSe NP composition and size after synthesis with different reaction conditions.

| $T_{\mu W}$ (° C.) | EDS (Pb At %) | EDS (Se At %) | Average Diameter (nm) | Diameter Standard Deviation (nm) | Coefficient of Variation (%) |
|---|---|---|---|---|---|
| 159 | 47 | 53 | 11.2 | 1.7 | 15 |
| 142 | 46 | 54 | 12.5 | 2.0 | 16 |
| 124 | 44 | 56 | 13.9 | 2.1 | 15 |
| 159 (without growth zone) | 93 | 7 | N/A | N/A | N/A |

Our results provide insights into PbSe NP growth mechanisms. Without being limited to any one theory, two possible routes for PbSe synthesis are shown in the following Chemical Equations 1 and 2, where $R_a=(CH_2)_7CH=CH(CH_2)_7CH_3$, $R_b$=phenyl, and $(R_aCO)O(OCR_a)$ is oleic anhydride. The large excess of Pb in the microwave only sample suggests that nucleation of PbSe NPs occurs via Chemical Equation 2 where reduction of lead oleate $(Pb(OA)_2)$ to $Pb^0$ by diphenyl phosphine (a contaminant in 90% TOP) precedes the formation of PbSe and may be accelerated by microwave radiation.

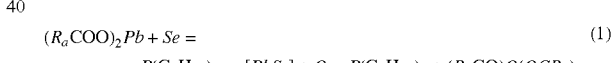

$$(R_aCOO)_2Pb + Se = \quad (1)$$
$$P(C_8H_{17})_3 \rightarrow [PbSe] + O = P(C_8H_{17})_3 + (R_aCO)O(OCR_a)$$

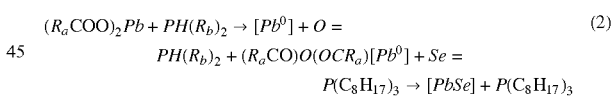

$$(R_aCOO)_2Pb + PH(R_b)_2 \rightarrow [Pb^0] + O = \quad (2)$$
$$PH(R_b)_2 + (R_aCO)O(OCR_a)[Pb^0] + Se =$$
$$P(C_8H_{17})_3 \rightarrow [PbSe] + P(C_8H_{17})_3$$

Excess Pb may indicate either the presence of Pb nanoparticles or PbSe nuclei with a Pb shell. Previous reports of Pb rich PbSe NPs have shown increasing Pb content with decreasing particle size. We found that samples synthesized using a $T_{\mu W}$ of 159° C., but without the growth zone, resulted in Pb:Se ratios ~9× larger than previously reported for 3.3 nm diameter PbSe NPs having a Pb shell. This suggests that our nuclei have a Pb shell and are much smaller than 3 nm diameter, or they are inherently Pb rich.

Figure 14:
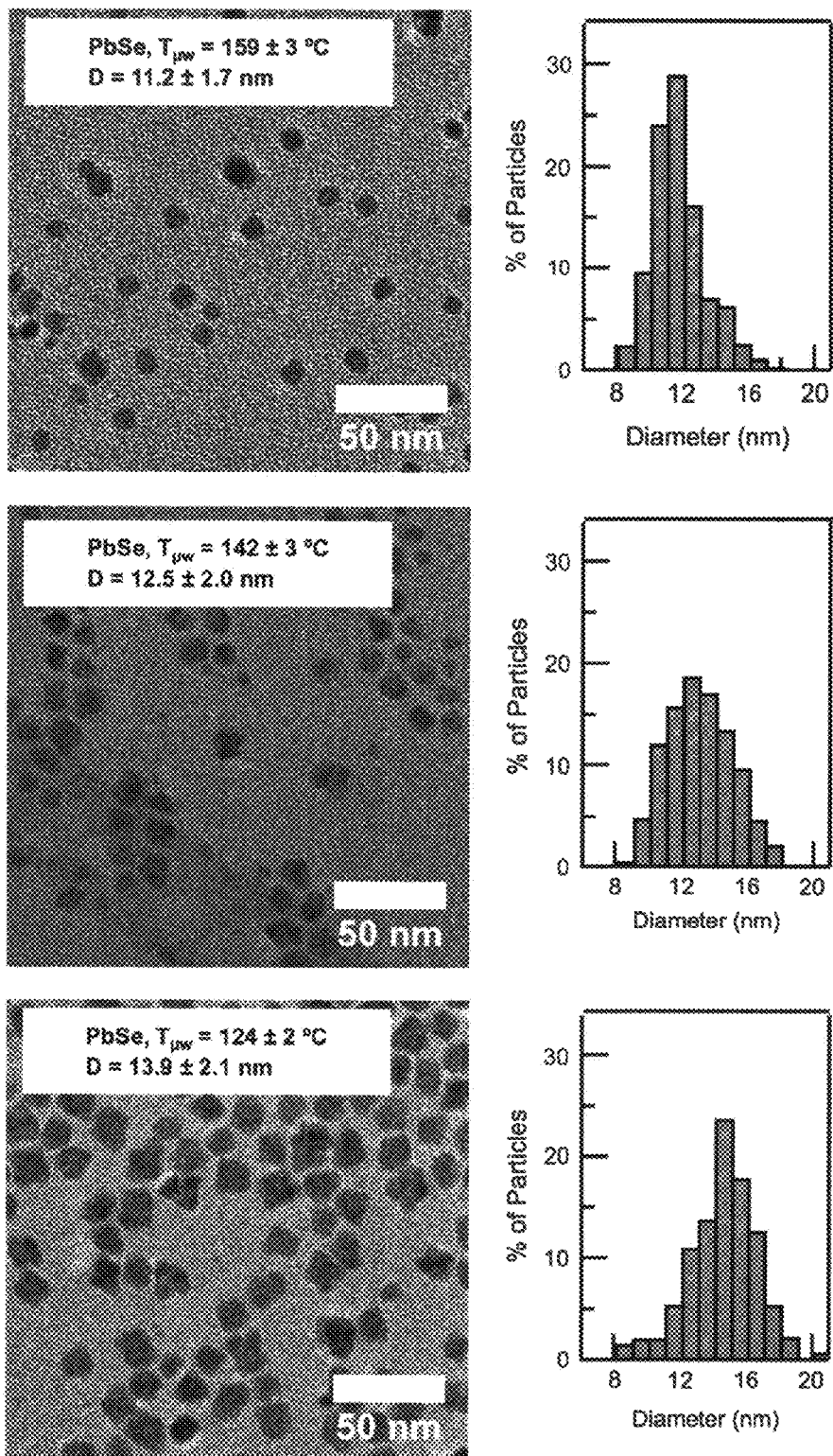
FIG. 14 graphically illustrates TEM images and particle size histograms for PbSe NPs synthesized with a $T_{\mu W}$ of 124, 142, and 159° C. and a growth temperature of 140° C.

Typical TEM images and size histograms for each $T_{\mu W}$ followed by a 140° C. growth zone are shown in FIG. 14. Average PbSe NP diameters are found to decrease with increasing $T_{\mu W}$ (Table 3). Average PbSe NP diameters were found to be 13.9, 12.5, and 11.2 nm for $T_{\mu W}$ of 124, 142, and 159° C., respectively. A coefficient of variation (100%×σ/$\bar{X}$) of ~15-16% was obtained without further size selection. Further analysis was performed to confirm that $\bar{X}$ and σ were statistically distinct using the ANOVA method for the three sets of data. The analysis indicated that the three distributions are significantly different where the calculated F value of 272 is significantly higher than the critical F value of 3.0. The smaller PbSe NP size for higher $T_{\mu W}$ is likely due to an increase in the number of nuclei generated in the microwave nucleation zone, with a corresponding decrease in dissolved precursor available during the growth stage. Additionally, increased heating ramp rates are expected to cause a more rapid a uniform nucleation event.

Figure 15:
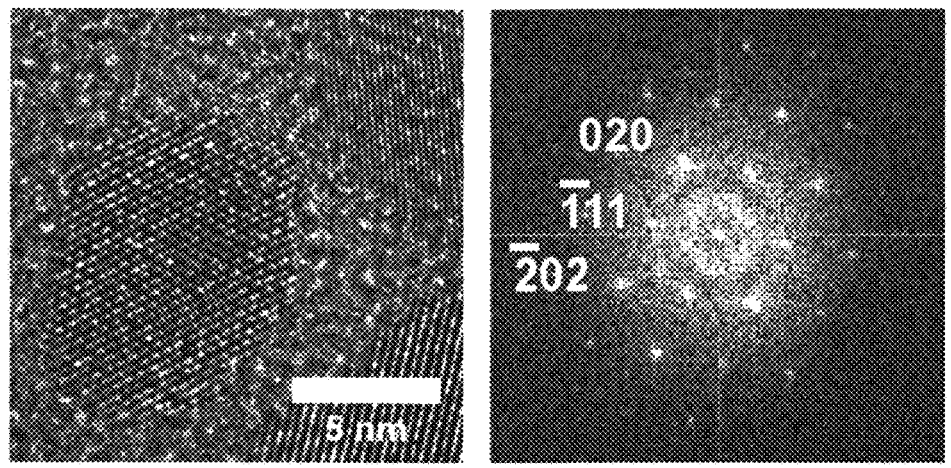
FIG. 15 pictorially illustrates HR-TEM and FFT images of PbSe NPs synthesized with a $T_{\mu W}$ of 124, 142, and 159° C. and a growth temperature of 140° C.
Figure 15:
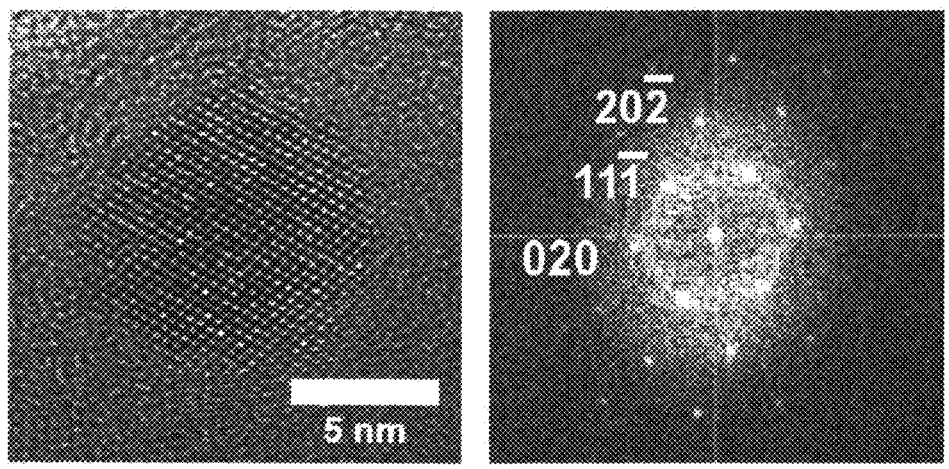
Figure 15:
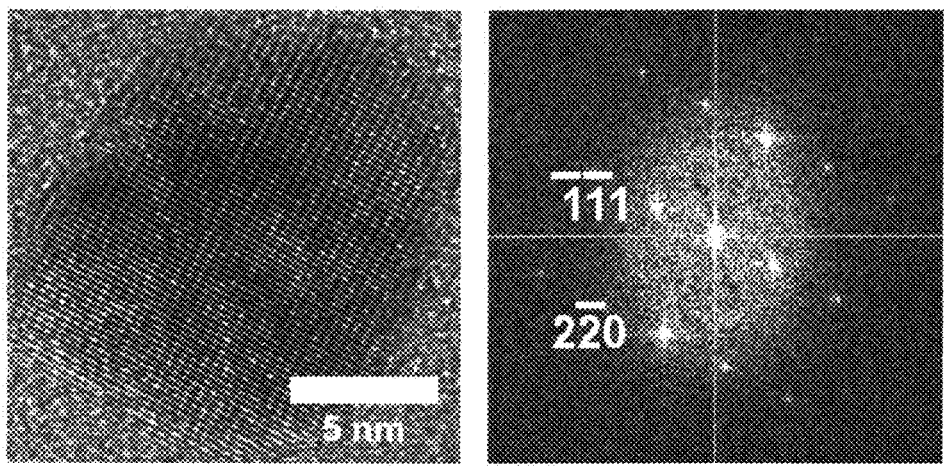
Figure 16:
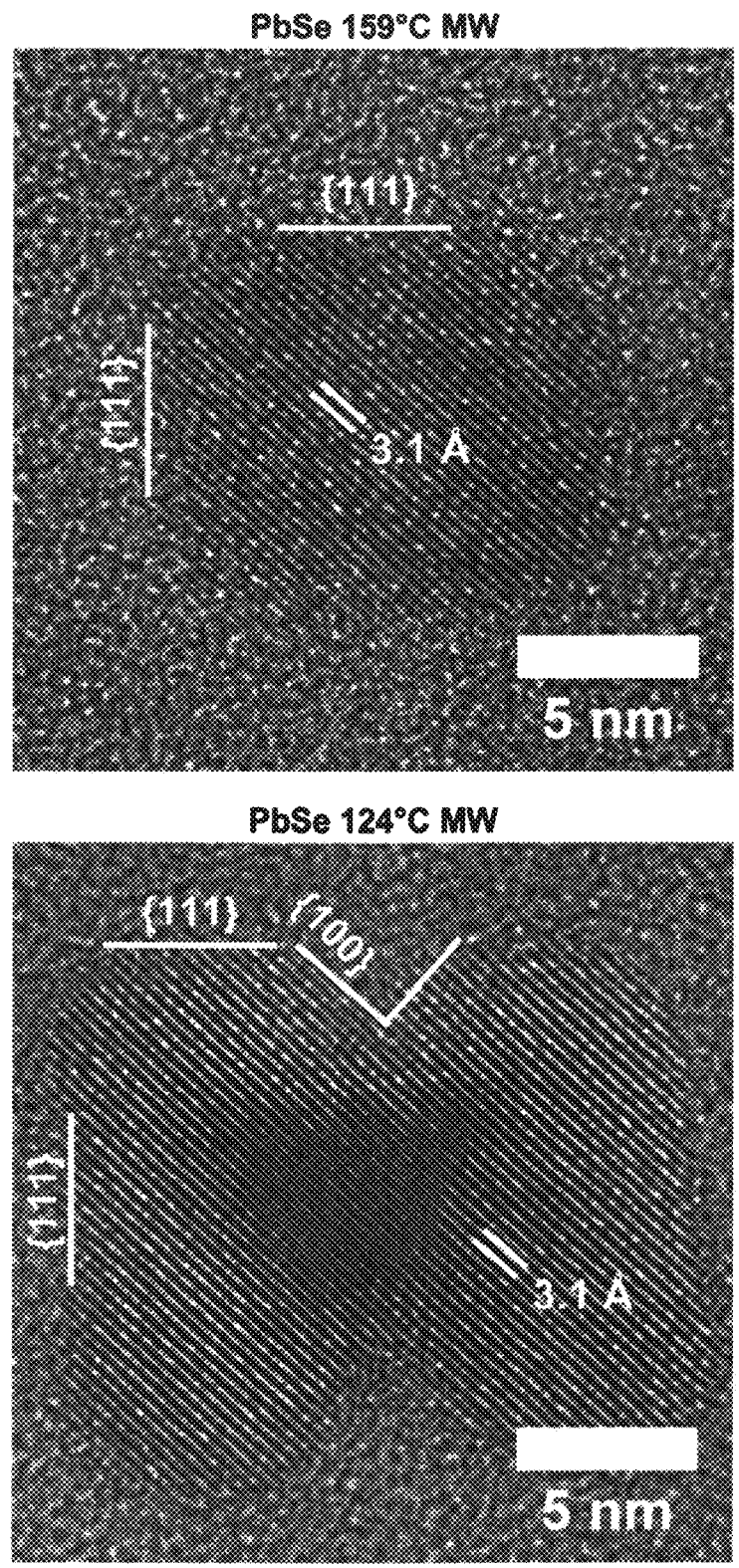
FIG. 16 pictorially illustrates HR-TEM images showing the shape of PbSe NPs synthesized with a $T_{\mu W}$ of 159 and 124° C. followed by a growth temperature of 140° C.

High-resolution TEM (HR-TEM) images of individual NPs were used to determine crystal structure by indexing fast Fourier transforms (FFT) of the images shown in FIG. 15. Only select planes in the FFT were labelled for clarity. The analyzed particles are shown along the [101] zone axis $T_{\mu W}$ of 159 and 142° C., and the [112] zone axis for a $T_{\mu W}$ of 124° C. In all cases the atomic spacings matched that expected for cubic PbSe and are in agreement with XRD results. TEM images (FIG. 14) of PbSe NPs synthesized using a $T_{\mu W}$ of 159 and 124° C. show particles with semi-spherical to rounded square shapes and more rectangular shapes, respectively. Closer examination of HR-TEM images for PbSe NPs from these reactions is shown in FIG. 16. For $T_{\mu W}$ of 159° C. the dominant sides of the square shaped PbSe NPs correspond primarily to the {111} surface planes and minority {100} surface planes that result in an octahedral or truncated octahedral morphology. For $T_{\mu W}$ of 124° C. the dominant sides of the particles correspond primarily to the {111} surface planes, however, facets in these surface planes are readily observed and we find these facets correspond to {100} surface planes. A statistical analysis was performed on over 500 PbSe NPs for each growth condition, and we found that 52%, 25%, and 10% had {100} surface plane facets for $T_{\mu W}$ of 124, 142, and 159° C. The (100) PbSe surface is significantly lower in energy than the (111) surface, which would suggest that the lowest energy state for PbSe NPs is cubic structures with exposed {100} surfaces. However, these studies also show the modification of relative surface energies due to adsorbed surface ligands.

We have found that varying microwave intensity in the microwave zone, and the resulting nucleation temperature, affected both size and shape of particles. Increasing the microwave intensity in the nucleation zone increases the heating rate of the solution and maximum temperature obtained. The increased microwave intensity causes an increase in the nucleation rate, resulting in a lower monomer concentration in the growth bath. With an increased number of nuclei and a lower concentration of monomers during the growth phase, the resulting PbSe NPs have a smaller average diameter and a spherical shape.

Conclusion.

In summary, a microwave-assisted segmented flow reactor was used to synthesize high quality PbSe NPs with low coefficients of variation (~15%). No additional crystalline impurities were observed in XRD. PbSe NP diameters were found to increase from 11.2 to 13.9 nm with decreasing $T_{\mu W}$. As the PbSe NP size increased the shapes of the particles were observed to evolve from semispherical and octahedral to multi-faceted structures. Observation of crystalline planes indicates that particles have a {111} truncated octahedral morphology for a $T_{\mu W}$ of 124° C. Pb rich nucleates were observed directly after the microwave indicating that reduction of Pb occurs during the nucleation zone, and that PbSe NPs form in the growth zone. These results demonstrate the use of a microwave-assisted segmented flow reactor as an effective method for the synthesis of high quality colloidal NPs.

Example 3

Figure 17:
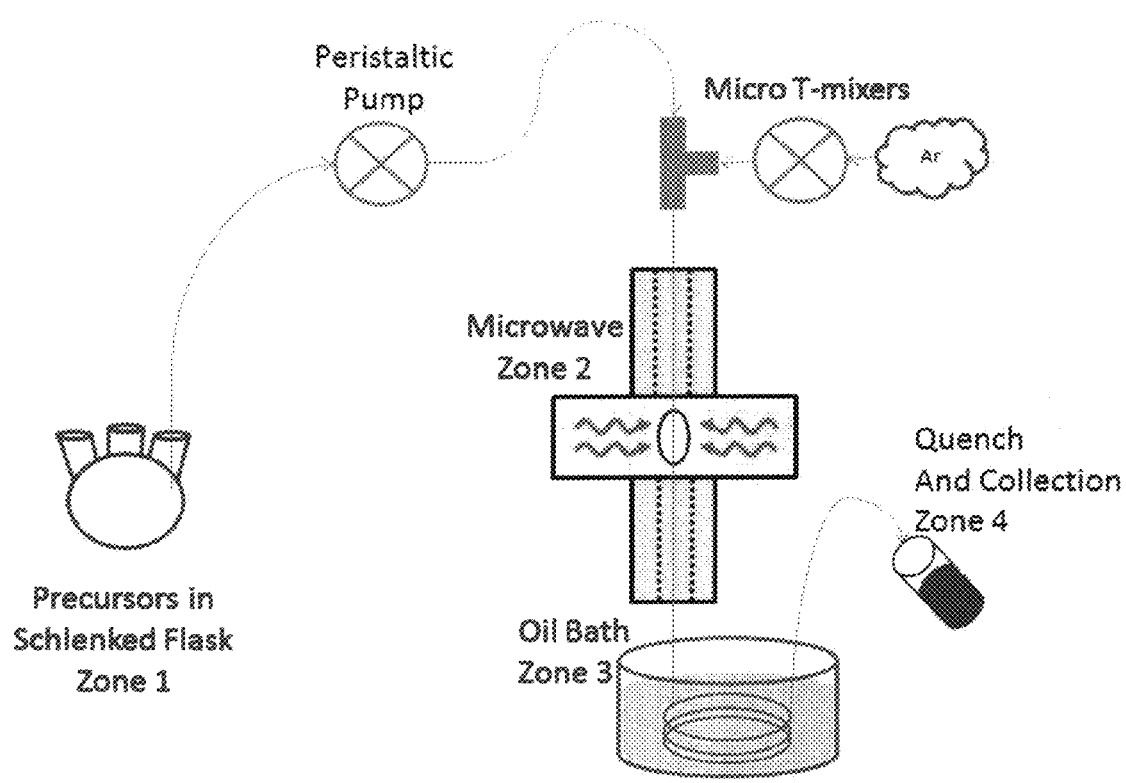
FIG. 17 diagrammatically illustrates an exemplary embodiment of the invention that may be used for the synthesis of $CuInSe_2$, $CuInS_2$, PbSe QDs. Precursor solutions are prepared in an air free three neck flask on a Schlenk line and peristaltic pumps are used to move the solution through PTFE tubing into the microwave heating zone, through an oil heating bath, and finally into the sealed collection vial under $N_2$ gas.

Microwave-Assisted Continuous Flow Synthesis of $CuInS_2$ Quantum Dots and Subsequent Cation-Exchange and ZnS Shell Growth Herein we describe a method for the production of $CuInS_2$ QDs using a microwave-assisted continuous, segmented, flow reactor (MWCFR) (see FIG. 17) for nucleation followed by growth in a conventional heat bath. The resulting QDs underwent Zn cation exchange and a ZnS shell was grown on the surface resulting in a photoluminescence quantum yield (PLQY) of 65%.

Experimental.

Core QD Synthesis: All reagents were stored in a glovebox. 1.8 mmol CuI and 3.6 mmol In(ac)$_3$ were dissolved in 47.5 g OLA, separately 7.2 mmol S powder was dissolved in 7.5 mmol diphenylphosphine (DPP) by heating to 50° C. in a $N_2$ filled glove box. The diphenylphosphine sulphide (DPPS) was mixed with 46 g ODE and then added at room temperature to the OLA solution. The resulting precursor solution was pale yellow and was always used within 24 hours. The solution was placed in a three neck flask attached to a schlenk line and run through several vacuum and purge cycles to remove any oxygen. Teflon tubing with 1/16" inside diameter was inserted through a septum into the flask and used to pump the solution to a tee where it combined with a flow of argon gas. Flow rates for solution and argon were set at 0.12 mL/min using the same peristaltic pump. The segmented flow of solution and argon gas bubbles then traveled into the microwave reactor (Sairem model PCCMWR340PVMR1PE GMP30 K; 3 kW; 2.45 GHz) where it was heated to approximately 125° C. in five seconds to nucleate nanocrystals. The solution then passed through a 5 m coil (approximately 9 minute residence time) of tubing immersed in a 160° C. oil bath to grow the particles and improve crystallinity. The particles were collected in a septum topped vial under a flow of nitrogen gas.

Cation exchange and ZnS Shell Growth: A solution of zinc oleate was prepared in a three neck flask by dissolving 13.8 mmol zinc acetate dihydrate in 30.4 mmol oleic acid and 22 mL ODE. This solution was brought to 140° C. under argon and thoroughly degassed. The solution was dropped to 100° C. and 10 mL of the CIS core reaction mixture was injected into the flask using a gas-tight syringe. The mixture was vigorously stirred and quickly brought up to 255° C. where the solution turned from black to blood red as zinc was incorporated into the CIS particles. After alloying the temperature was dropped to 210° C. and additional DPPS was added to grow a thicker ZnS shell on the particle surface. Our results have shown that adding this additional shell growth step does not significantly improve the PLQY in raw reaction mixtures but it helps the solutions retain their PL after washing.

Purification: Solutions were washed using liquid-liquid extraction first with methanol, then with mixtures of methanol and increasing fractions of acetone. Finally the particles were crashed using pure acetone, resuspended in toluene, crashed again using methanol, and resuspended in toluene.

Electrohydrodynamic Printing: Orange emitting core/shell QDs were washed and redispensed in a saturated solution of thiophenol in hexane to form a concentrated QD ink. The electrohydrodynamic ink jet printer uses an electric field to eject ink from the nozzle to the substrate. The substrate is mounted onto a stage equipped with a Parker MX80LTO3MP electronic x-y translation system. Ink is dispensed from a syringe attached to a Au/Pd coated glass needle mounted vertically above the substrate. The vertical distance between the needle and substrate is controlled by moving the needle along the z-axis with a Parker MX80MT02MS motor. The glass needle had a 30 μm tip diameter and was supplied from World Precision Industries. The needle was sputter coated with 20 nm of Au/Pd to make it conductive. The metal coated needle was dipped in 1H,1H,2H,2H-Perfluorodecanethiol from Sigma-Aldrich for 2 minutes to make the outside of the needle hydrophobic. A Trek 677B voltage amplifier supplied a pulsed DC voltage between the needle and grounded substrate. The stage can be leveled using a two axis tilt mount to keep the vertical height constant while the stage is moving. Pressure applied to the back of the syringe is controlled by an E/P pressure transducer. The pressure helps drive the ink through the capillary and to the tip. An Infinity 2-2 camera is mounted to help position the needle and monitor printing. The system is controlled by custom labview software.

Characterization: Photoluminescence quantum yield (PLQY) measurements were taken from cleaned QD solutions in toluene. 1 cm path length quartz cuvette mounted in an integrating sphere with a 440 nm LED with cutoff filters to narrow the excitation light. UV-vis absorption measurements were taken using a (specs from PLT) spectrometer. X-ray diffraction (XRD) was done using an Ultima Rapid diffractometer using Cu K-α radiation, particles were drop casted onto glass slides and a 2 theta scan rate of 5 degrees/minute was used. Raman spectra were taken using a Horiba Jobin-Yvon HR800 confocal spectrometer with a 532 nm diode laser passed through a notch filter. The confocal pin-hole was set at 100 μm, a 100× objective was used, and signals were detected using a Synapse charge coupled device (CCD). TEM images were taken using a FEI Titan field emission gun microscope. Clean QDs were suspended in toluene and dropped onto a gold, lacey carbon TEM grid with an ultrathin carbon film, excess toluene was wicked away with a tissue.

Results.

Figure 18A:
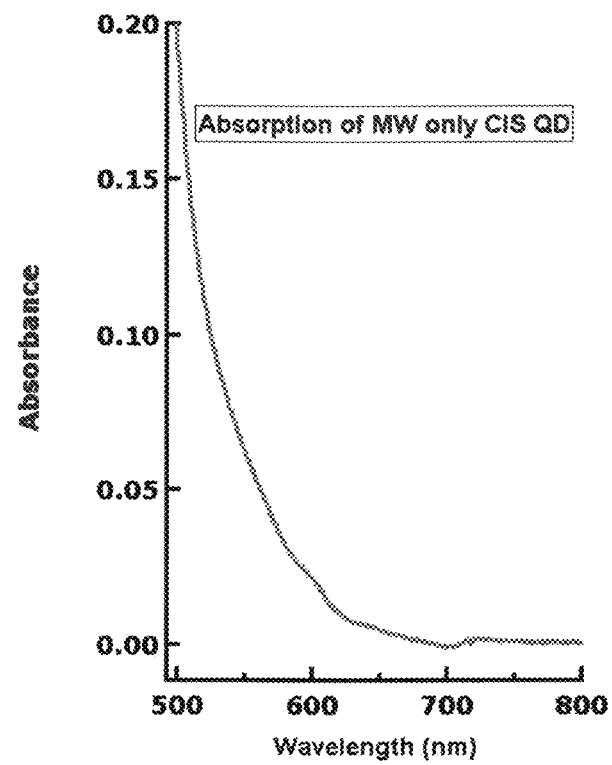
FIGS. 18A and 18B graphically illustrate UV-Vis spectra of $CuInS_2$ QDs prepared by systems of the claimed invention.
Figure 18B:
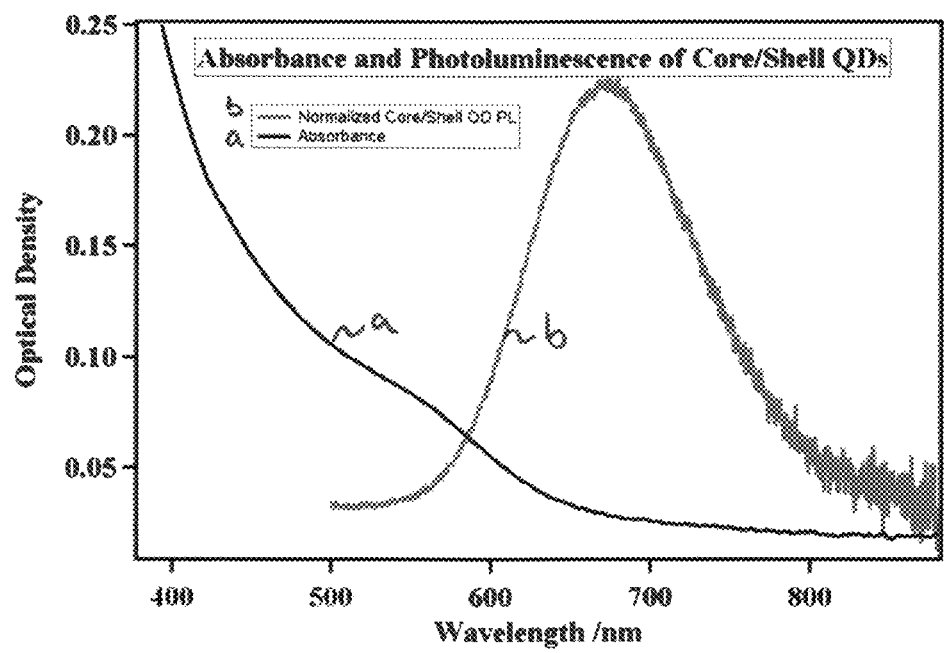

UV-vis and observations: Stable precursor solutions which appeared pale yellow-green became a darker yellowish-orange after passing through the microwave zone. The change in color was evaluated by taking a UV-vis spectrum of the solution leaving the microwave zone, FIG. 18 hereafter called MW only, while using the precursor solution as a blank. The spectrum shown in FIG. 18 is typical for small (<4 nm) $CuInS_2$ nanocrystals with an absorption onset at 610 nm. After leaving the microwave reactor and entering the 170° C. oil bath the solution changes from yellow to red to black in two seconds. A UV-vis spectrum of the solution collected after a 9 minute residence time in the 170° C. bath, hereafter referred to as core solution, shows an onset of absorption near 700 nm consistent with larger $CuInS_2$ quantum dots. As prepared core solution was mixed with Zn-oleate and heated to 250° C., a color change from black to reddish brown was observed which is attributed to cation exchange with zinc. UV-vis spectra of the QDs after cation exchange (FIG. 18) show the absorption onset blue-shifts to 600 nm. After adding additional zinc and sulfur precursors to grow a protective ZnS shell over the QDs the absorption onset remains at 600 nm but the absorption increases in the region between 300 and 400 nm indicative of ZnS growth.

Photoluminescence: PL spectra were compared for the MW only, core, cation exchange, and core/shell samples. The MW only samples showed no PL, and the core samples showed very weak, broad PL from 600 to 880 nm. This broad, red-shifted PL is indicative of a large number of trap states present on the surface. Aliquots taken during cation exchange show a gradual blue-shift in the PL peak and a drastic increase in intensity. Despite the bright PL observed in the as-prepared cation exchange solutions, the PL was extinguished after cleaning. Core/shell samples retained the PL peak position of the cation exchange samples and also retained their PL after cleaning. PLQY measurements were performed on the best core/shell sample and 69% of 450 nm photons were downconverted by the sample into longer wavelength photons.

Figure 19A:
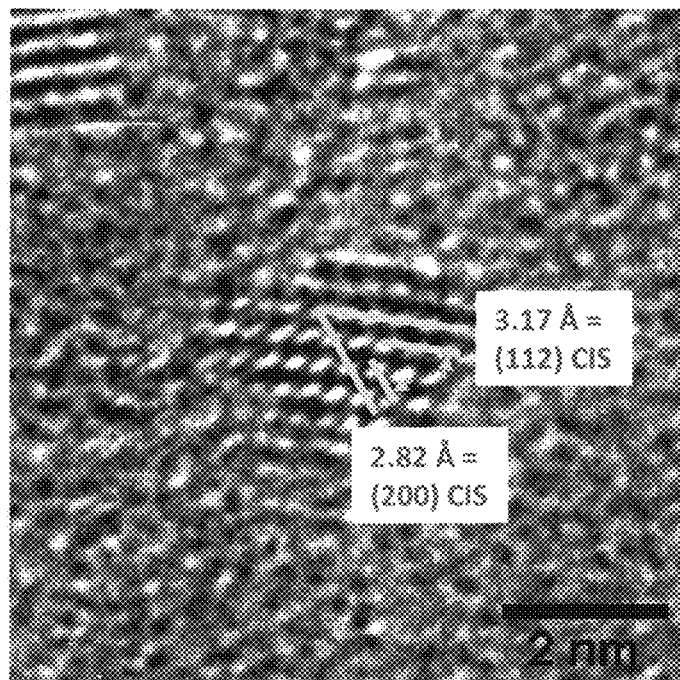
FIGS. 19A and 19B pictorially demonstrate HR-TEM images of (FIG. 19A) core $CuInS_2$ QDs and (FIG. 19B) core/shell QDs.
Figure 19B:
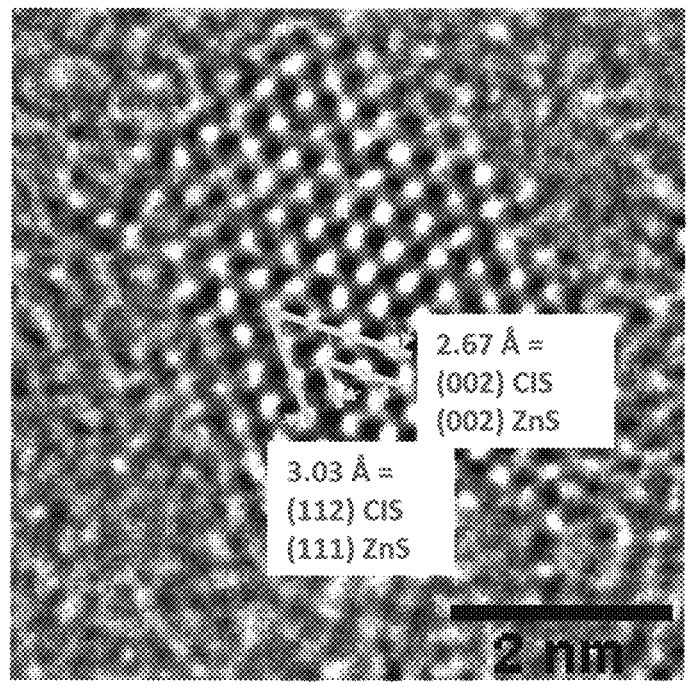
Figure 20A:
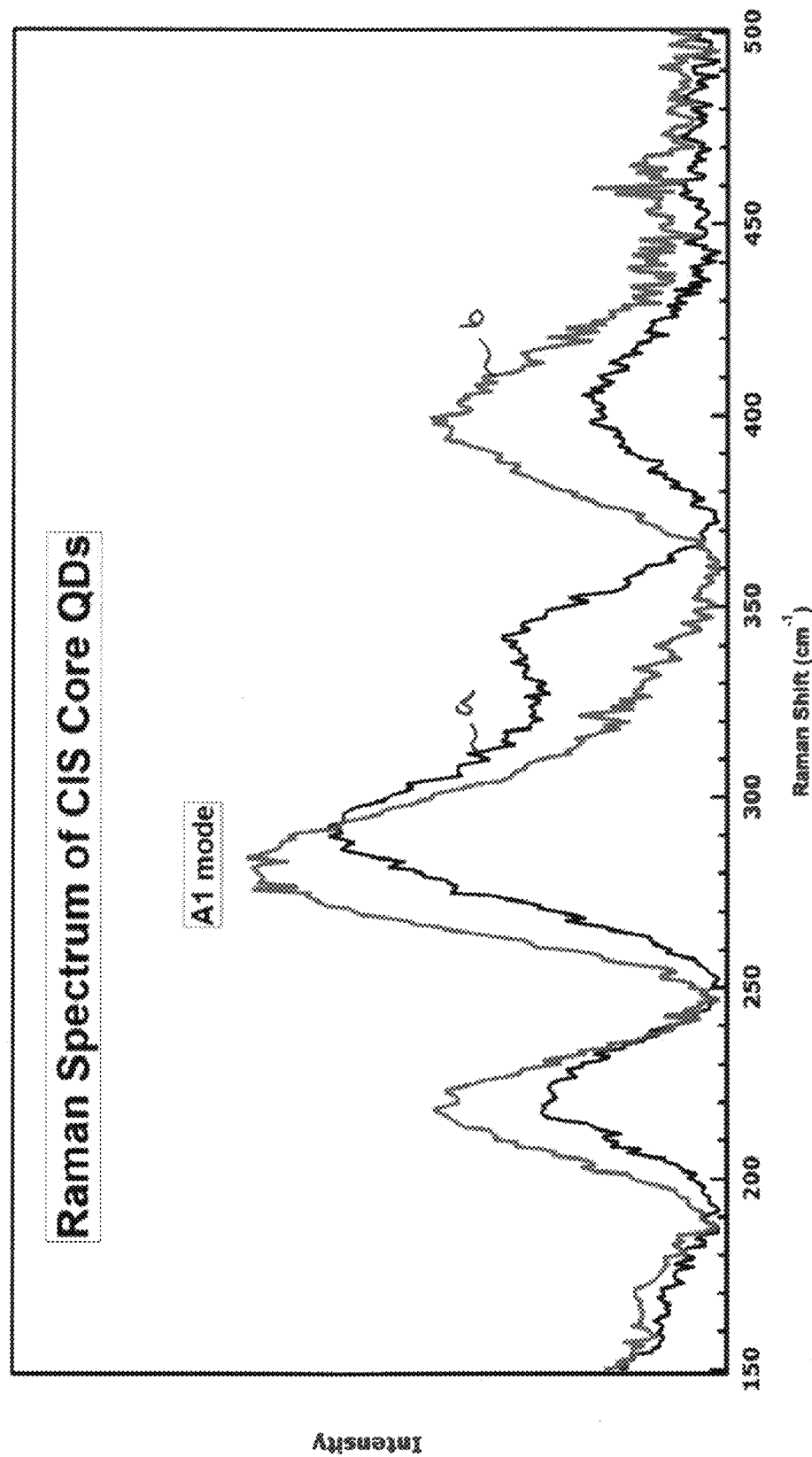
FIGS. 20A and 20B graphically illustrate Raman spectra of $CuInS_2$ QDs prepared by systems of the claimed invention.
Figure 20B:
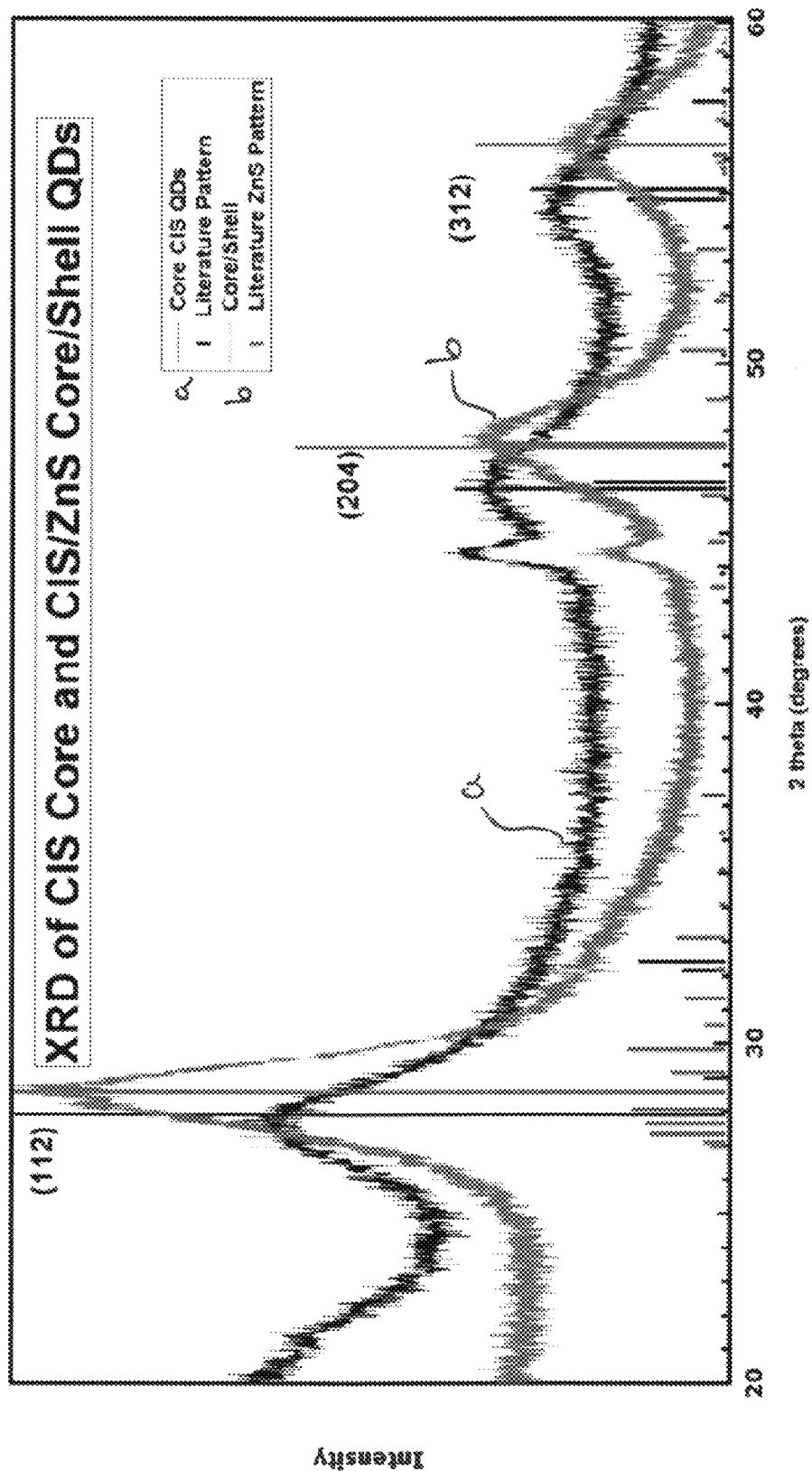

Transmission electron microscopy: TEM imaging indicated that the core particles were 3.4±2.2 nm in diameter, spheroidal, and HRTEM indicated that the atomic spacings are consistent with the $CuInS_2$ chalcopyrite crystal structure. Core/shell QDs were 4.1±2.7 nm, spheroidal, and HRTEM showed that they had adopted the shorter atomic spacings of ZnS. The change in the lattice parameter can also be seen by XRD in FIG. 19 where the diffraction peaks move to longer 2θ after cation exchange and shell growth. Raman spectroscopy showed a similar trend with the main peak, the A1 vibrational mode, moving from a Raman shift of 291 $cm^{-1}$ for the core to 281 $cm^{-1}$ for the core/shell sample (see FIG. 20A). The 291 $cm^{-1}$ position for the A1 peak has been reported previously for chalcopyrite $CuInS_2$, and the shorter shift is consistent with the decreased bond length in ZnS. The core sample has an additional Raman peak at 340 $cm^{-1}$ which has previously been attributed to a Cu vacancy defect in the crystal. FIG. 20B indicates an XRD of the CIS core and the CIS/ZnS Core/Shell QDs prepared by the methods described herein.

Composition: The ratios of metals in both the core and core/shell QDs were determined by ICP. Core QDs were found to contain 23% copper and 77% indium while the core/shell QDs contained 98% zinc with 0.3% copper and 0.9% indium. The 1:3 ratio of copper to indium is consistent with the ratio added in the synthesis and does not appear to have changed significantly during cation exchange.

Printing: QD ink was used to print the letters OSU onto a silicon wafer using a custom electrohydrodynamic printer. After drying overnight in air the printed letters appeared bright orange under a UV light. Visible light microscope imaging revealed the letters to be approximately 250 microns in height with a line thickness of 35 microns.

Discussion.

Our goals for the reactor included that it must be easily scalable for industrial applications, allow for strictly air-free synthesis and provide independent control over nucleation and growth of QDs. Our method of inserting PTFE tubing directly through the septum of a Schlenked three-neck flask was effective in keeping the solution strictly air-free and avoiding side reactions with oxygen. The use of a MWCFR for nucleation of the QDs allowed for rapid, direct, volumetric heating of the precursor solution. Ideally, the monomers traveling through the nucleation zone will reach a temperature at which they will decompose and form very small nanocrystals and significantly reduce the monomer concentration in the solution to prevent continued nucleation. By heating the solution directly using microwaves, rather than by conduction through the tubing, the nucleation of colloidal QDs is promoted over the deposition of QDs on the walls of the tubing. Segmenting the solution flow by introducing argon gas into the flow also reduced sidewall deposition by increasing circulation. The microwave intensity in the nucleation zone can be precisely tuned and the residence time can be altered by changing either the flow rate or the diameter of tubing to achieve the desired heating rate and maximum temperature. For this reaction, the microwave reactor was tuned to achieve a very slight color change consistent with very small CIS QDs.

The growth bath was added after the nucleation zone to increase the QD size, consume the remaining copper and indium precursors, and improve crystallinity of the QDs. The ICP results confirm that the ratio of metal ions in the precursor solution is preserved in the core QDs indicating that all of the copper and indium was consumed. Previous studies on the growth of CIS QDs have shown that copper reacts preferentially with sulfur and longer reaction times are required to incorporate Indium into the QDs. The conditions for growth of the QDs can be optimized by changing the temperature of the oil bath, and the residence time can be controlled by changing the tubing diameter and length of tubing.

Cation exchange and Shell Growth: The core CIS QDs showed essentially no visible PL as expected for oleylamine capped CIS. Cation exchange was used to increase the band-gap and passivate trap states on the QD surface to increase PLQY. By exchanging the surface copper and indium ions with zinc the surface becomes essentially a ZnS surface which will facilitate epitaxial ZnS shell growth later. The core CIS QDs were grown with an excess of the sulfur source, DPPS, which could allow some shell growth during the cation exchange step, though previous studies have shown that excess sulfur is not needed during cation exchange. The blue shift seen in the PL spectra during cation exchange show that the cation exchange was effective in increasing the bandgap of the QDs but the PL decreased over time when exposed to air indicating that the cation exchange was not preventing charge carriers from reaching the QD surface. The high temperatures necessary to exchange ions in CIS (250° C.) were above the safe limits for the oil bath and PTFE tubing so the cation exchange and shell growth were done in a batch reactor.

Shell growth was carried out at between 200 and 210° C. to allow for growth of ZnS without providing the high temperature necessary for mobilizing copper and indium ions remaining in the lattice. The impressive PLQY achieved for the core/shell QDs indicates that we were successful in isolating charge carriers to the core of the nanocrystal. Collectively, the cation exchange and shell growth converted the core CIS QDs into slightly larger core/shell QDs that have the lattice parameter of ZnS and approximately 99% ZnS composition. At this low level of Cu and In concentration, these two elements are essentially acting as co-dopants within the ZnS lattice and the PL is dominated by this donor-acceptor emission.

Conclusion.

$CuInS_2$ QDs were synthesized for the first time using an air-free MWCFR. These QDs underwent cation exchange with zinc in a batch reaction and were then coated in ZnS. TEM, XRD and ICP showed that the resulting QDs were composed mostly of ZnS with CIS present at about 1% by metals basis. The core/shell QDs downconverted 450 nm LED light with 69% efficiency, showing great promise for these materials as a heavy metal-free downconversion material for LEDs.

Example 4

Gas-Liquid Segmented Flow Microwave-Assisted Synthesis of CPO-27-Ni Under Moderate Pressures $Ni_2(dhtp)(H_2O)_2 \cdot 8H_2O$ (CPO-27-Ni) based NCs or metal organic frameworks (MOFS) were synthesized in a continuous-flow microwave assisted reactor obtaining high space-time yield (~90 $g \cdot h^{-1} \cdot L^{-1}$ and 96.5% of reagents conversion). Separation between nucleation and growth was attempted by using uniform and rapid microwave heating to induce nucleation and substantially increase conversions in shorter reaction times under milder conditions of pressure. High yields were achieved in minutes as opposed to days for typical batch syntheses as well as control over material properties due to more uniform nucleation and growth steps. A microwave-assisted continuous flow reactor using gas-liquid segmented flow was employed to induce fast nucleation which should accelerate MOFs synthesis while facilitating control over its particle size. Optimization of microwave reactor parameters has led to improvements in the MOF's crystallinity, reagent conversion, and production rates. Differences in crystallinity were observed as smaller grains were formed when higher microwave power was applied. Crystallinity differences led to different final adsorption behaviors and surface areas. Herein we could show a continuous high space-time yield synthesis of CPO-27-Ni which allowed control over nucleation using the advantages of microwave heating.

Chemicals:

All chemicals were used as purchased without any further purification. Nickel acetate tetrahydrate (>98%) was obtained from Alfa Aesar, 2,5-dihydroxyterepthalic acid (>98%), (DOBDC), was obtained from TCI America, and Dimethylformamide (DMF) (99.8%) was obtained from EMD.

Figure 21:
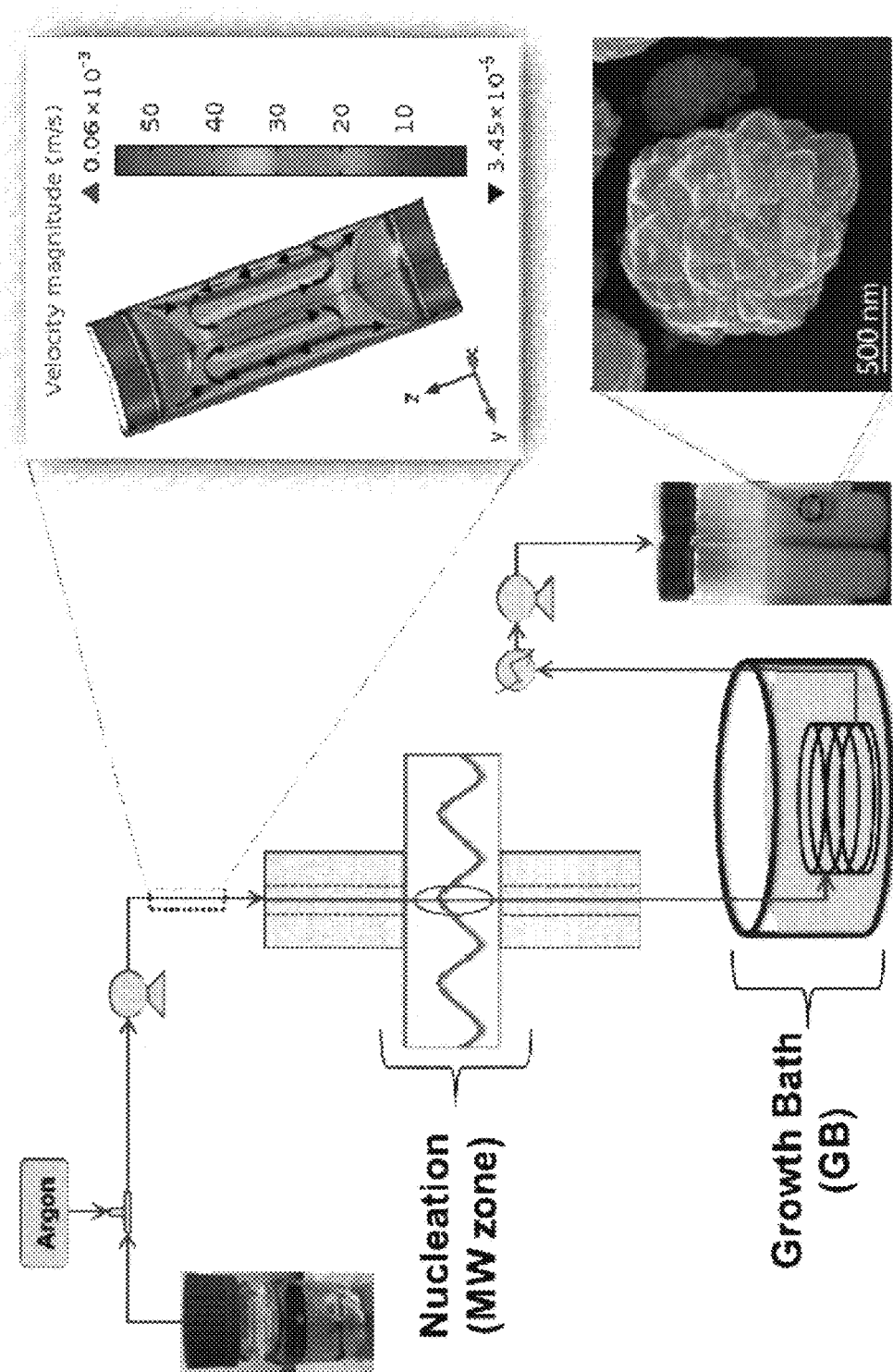
FIG. 21 schematically illustrates a continuous flow microwave-assisted system of the invention used in the synthesis of CPO-27-Ni NPs at 2.5 bar.

Synthesis:

Continuous microwave-assisted synthesis of CPO-27-Ni was performed at 2.5 bar under solvothermal conditions with a second peristaltic pump as a back pressure regulator as illustrated in FIG. 21. Precursor solution was prepared by mixing 50 mL of Nickel (II) acetate tetrahydrate dissolved in DI water (0.12 M) with 50 mL 2,5 dihydroxyterepthalic acid (DOBDC) dissolved in DMF (0.06 M). Argon gas was injected into the system through T-junction with precursors to attain segmented flow regime. The reaction system consisted of Teflon® tubing (⅛ in outer diameter, 1/16 in inner diameter) in the microwave zone and growth bath. After reaction, liquid dispersion of products was then centrifuged to separate particles from solvents and unconverted reagents. MOF particles were then cleaned by sonicating products in water for about two minutes being followed by new centrifugation and addition of methanol. Particles were sonicated in fresh methanol then centrifuged and more 10 mL of fresh methanol were added to sample. Procedure was repeated four times in three days. Activation procedure was executed on three days by keeping samples under vacuum at 80° C. until powder was completely dry before characterization.

Characterization:

Powder X-ray diffraction (PXRD) was performed at room temperature in a Rigaku Ultima IV diffractometer (Cu—Kα=0.1542 nm). Points were collected from 2θ=5-50°. Before experiments, dried powder was ground for about 2 min using a mortar and pestle. Thermogravimetric analysis (TGA/MS) was performed using a TA Instruments TGA 2950. Samples were heated up to 700° C. at 5° C./min under $N_2$ flow of 80 mL/min. Transmission electron microscopy (TEM) imaging was performed using a FEI Titan FEG at 200 kV. For TEM imaging, samples were prepared from ethanol dispersion of MOF samples which were sonicated for 30 min prior to preparation. A carbon coated copper grid was dipped into the MOF dispersion twice and taken into microscope after drying at room temperature. Scanning electron microscopy (SEM) imaging was performed using an FEI Quanta 600 FEG SEM with 15-30 kV accelerating voltage. Raman spectra were obtained from samples exposed to air using a Horiba-Jobin Yvon HR-800 Raman spectrometer with a 532 nm incident laser source. Conversion data was evaluated by performing UV-Vis spectroscopy using an AvaSpec-3648 spectrometer on precursor solution and supernatant obtained from centrifuged reaction product. N2physisorption measurements were taken on an ASAP 2020 (Micromeritics). Particle size was determined using dynamic light scattering (DLS) on a Zeta Potential analyzer—Brookhaven Instruments Corp. CPO-27-Ni suspensions in hexanes were analyzed after 30 min of sonication.

Results and Discussion:

The synthesis shown in this work was performed after optimization of the combined nucleation zone (Microwave reactor) and growth zone (Heating bath) in a continuous-flow reactor. Several parameters were varied with the objective of maximizing reagent conversion with shortest residence time under mild reaction conditions. The effect of microwave power on the synthesis process was investigated to understand the underlying mechanism.

Gas-liquid segmented flow was introduced to the reactor to facilitate longer reaction times. Fouling and deposition on reactor walls are common in nanoparticle synthesis which can cause tubing to clog and create hot spots in the microwave zone where a deposited particle can cause strong microwave absorption, which can lead to arcing and tube rupture. Segmented flow was already employed in nanoparticle synthesis for inducing circulation within aqueous slugs and promoting better mass/heat transfer which results in more uniform products.

Figure 22:
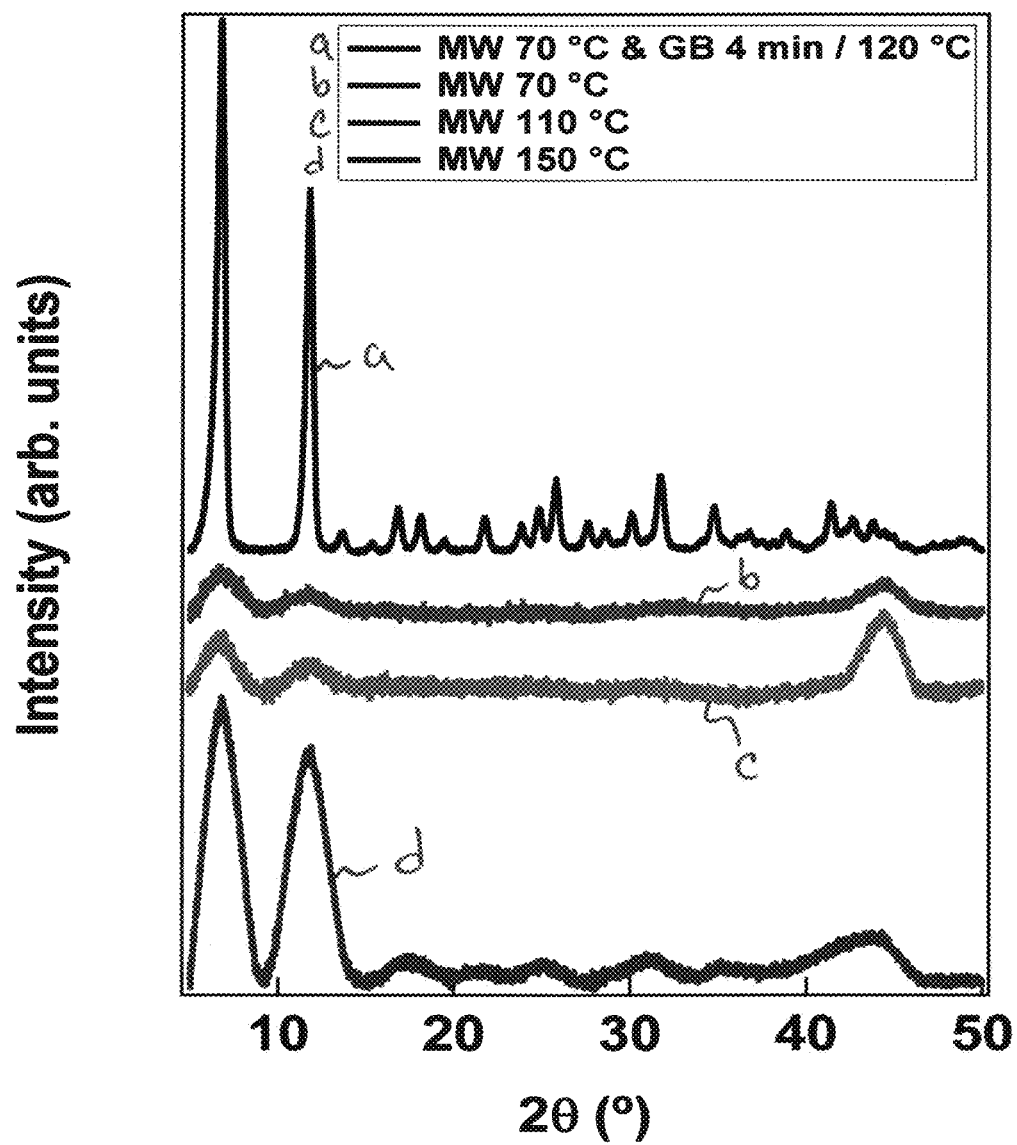
FIG. 22 graphically illustrates X-ray diffractograms (XRD) of CPO-27-Ni NPs synthesized at different temperatures in MW zone compared to a sample, which has been synthesized using a combination of a microwave zone and a heating bath: (a) microwave at 70° C. and growth bath at 4 mins at 120° C.; (b) microwave at 70° C.; (c) microwave at 110° C.; and (d) microwave at 150° C. (Peak at 2θ=44° present in samples from microwave only synthesis is due to X-ray diffractometer metal stage).

X-ray diffraction was employed to show effects of different synthetic conditions on the long range order in the MOF particles. FIG. 22 shows PXRD data for particles synthesized using the microwave zone and a heating bath as well as samples collected after the microwave zone with no heating bath. The sample collected using a 70° C. microwave zone temperature and 120° C. growth bath exhibits a typical pattern for CPO-27-Ni which is in agreement with available crystallographic information. The most intense peaks are at $2\theta=6.8°$ and $11.8°$ which correspond to $d_{hkl}=12.99$ Å and $7.51$ Å that are related to planes (-120) and (030). Broad peaks are seen in the pattern obtained from material synthesized using the microwave zone only which can indicate formation of smaller grains or an amorphous phase. Results for samples synthesized using only microwaves show increasing peak intensities in x-ray diffraction patterns as temperature in microwave reactor increased, which points to a formation of more crystalline materials as power increases. However, growth bath seems to prepare highly crystalline MOFs.

Raman spectroscopy analysis helped identify all peaks that belong to CPO-27-Ni. Bands at 1619, 1560, 570 cm$^{-1}$ are assigned to benzene ring. Stretch vibrations are associated to the former and ring deformation vibrations to the latter. Peaks at 1501 and 1416 cm$^{-1}$ are related to $\nu(COO^-)_{asym}$ and $\nu(COO^-)_{sym}$ respectively. The very intense peak at 1275 cm$^{-1}$ is associated to $\nu(CO)$ species after deprotonation of hydroxyl groups. The peak at 827 cm$^{-1}$ is related to benzene ring C—H bending modes and finally, the band at 410 cm$^{-1}$ is associated to $(Ni-O_{ligand})$ bond vibration. All peaks are present with similar intensity and broadness for all samples synthesized at different temperatures in microwave zone alone which confirmed formation of CPO-27-Ni for reactions run at low and high temperatures but heating bath increased crystallinity as sharper peaks were once again seen for the sample that went through both zones. (See FIG. 23).

Based on the results of PXRD and Raman spectroscopy, microwaves seem to change relative crystallinity of CPO-27-Ni as a function of power applied. In comparison to conventional heating, higher microwave power led to formation smaller due to higher nucleation rates in the presence of microwaves. The presence of smaller and dispersed crystals exhibited superior adsorption properties because of higher surface area exposure.

Samples were synthesized at different heating rates in nucleation zone to evaluate microwave effects on CPO-27-Ni crystallinity as a function of microwave power when all samples went through a heating bath. A preliminary work performed in single phase flow, showed that the microwave zone increased conversions by a factor of up to 50% for a 150° C. in MW zone/120° C. heating bath compared to the heating bath alone. In fact, if evaluating conversions in the MW reactor alone using single phase flow, we could observe formation of particles from 70° C. (~4% conversion) to 150° C. where reagents conversion reached a little above 50%. However, the increase in conversion also resulted in reduction of relative crystallinity when MW zone is held at higher temperatures. Although, the MW reactor when operated at lower powers would not produce the same increase on conversion, a slightly higher crystallinity could be observed for the samples synthesized at lower temperatures in microwave zone. (See X-ray diffraction Full Width at the Half Maximum, FWHM, summarized in Table 4; see also FIGS. 23 and 24).

Figure 23:
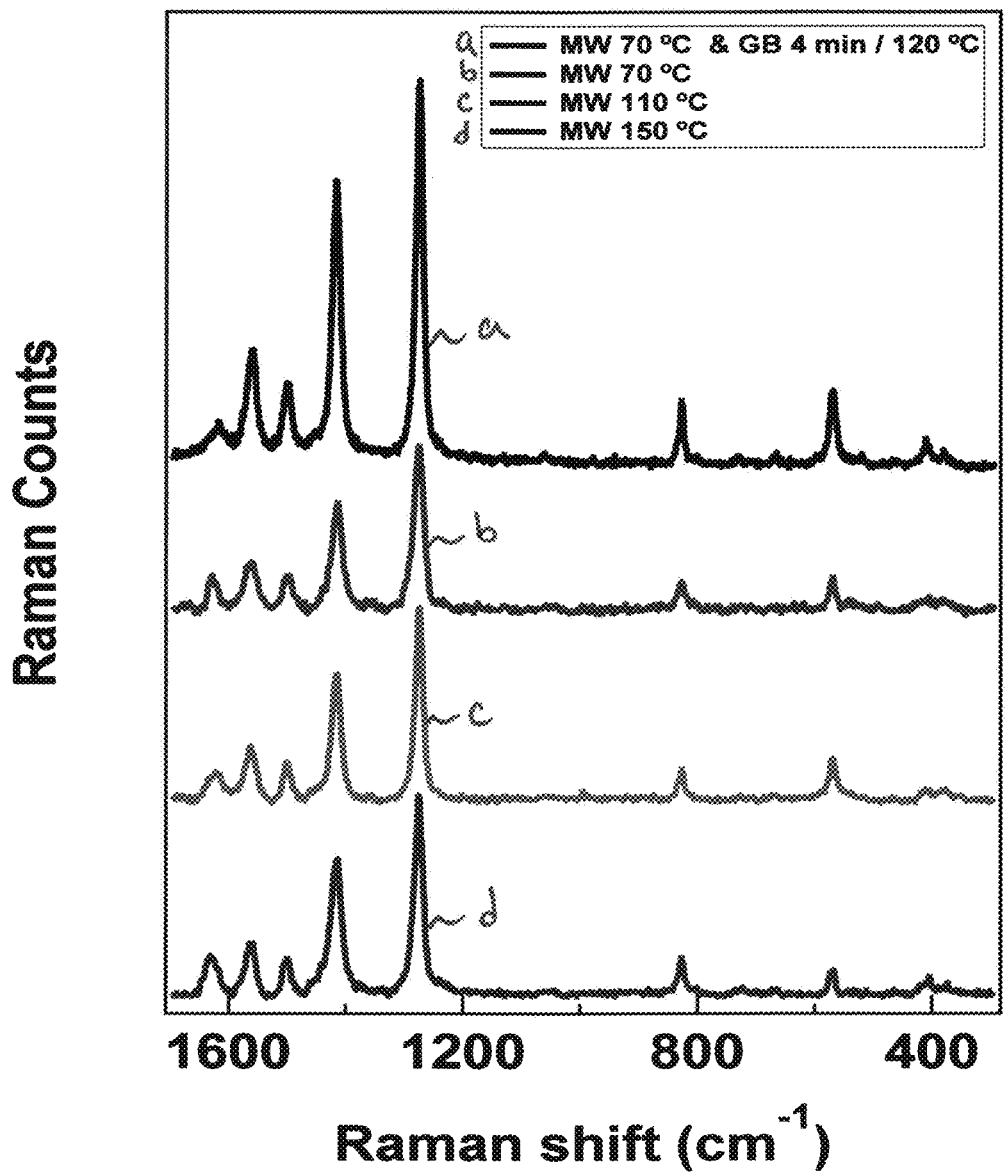
FIG. 23 graphically illustrates Raman spectra of CPO-27-Ni samples which were synthesized at different in MW zone compared to a sample that went through a combination of the microwave zone and a heating bath: (a) microwave at 70° C. and growth bath at 4 mins at 120° C.; (b) microwave at 70° C.; (c) microwave at 110° C.; and (d) microwave at 150° C.

Raman spectroscopy was employed as a complementary technique to X-ray diffraction to investigate changes to bonds related to CPO-27-Ni linker or linker-Metal under different reaction conditions. Results showed the expected CPO-27-Ni pattern for all samples without shifts of any expected peaks (FIG. 23). However, the same trend observed on XRD results was observed since Raman peaks broaden with higher heating rates in the microwave zone and narrower and more intense peaks were observed for low MW temperatures. Both techniques agreed on the general trend of reduction of relative crystallinity. The specific effects were again implying differences which are related to a relative decrease of crystallinity when microwave power is varied. However, such effects were still embedded in the broadness of the peaks which could caused by defects formed during the fast crystallization induced in MW zone, or by formation of smaller grains leading to a polycrystalline material, or combination of both.

TABLE 4

Reagents conversion (evaluated using UV-Vis spectroscopy for Ni$^{+2}$ concentration), Mass production rate of CPO-27-Ni, and XRD Full Width at Half Maximum from reactions operated in segmented flow at different microwave powers.

| Conditions | Conversion (%) | Mass Prod. Rate of CPO-27-Ni (g/h) | XRD FWHM at 31.75° (°) | BET isotherm surface area (m$^2$/g) |
|---|---|---|---|---|
| No MW | 90.8 | 3.93 | 0.660 | 1012 ± 6 |
| MW 70° C. | 92.3 | 4.46 | 0.536 | 938 ± 6 |
| MW 110° C. | 94.3 | 4.51 | 0.662 | 936 ± 6 |
| MW 150° C. | 96.5 | 4.56 | 0.850 | 840 ± 3 |

Transmission electron microscopy images were used to investigate effects of power in the microwave zone and correlate its effects with the differences in crystallinity pointed out by X-ray diffraction and Raman spectroscopy.

Figure 25A:
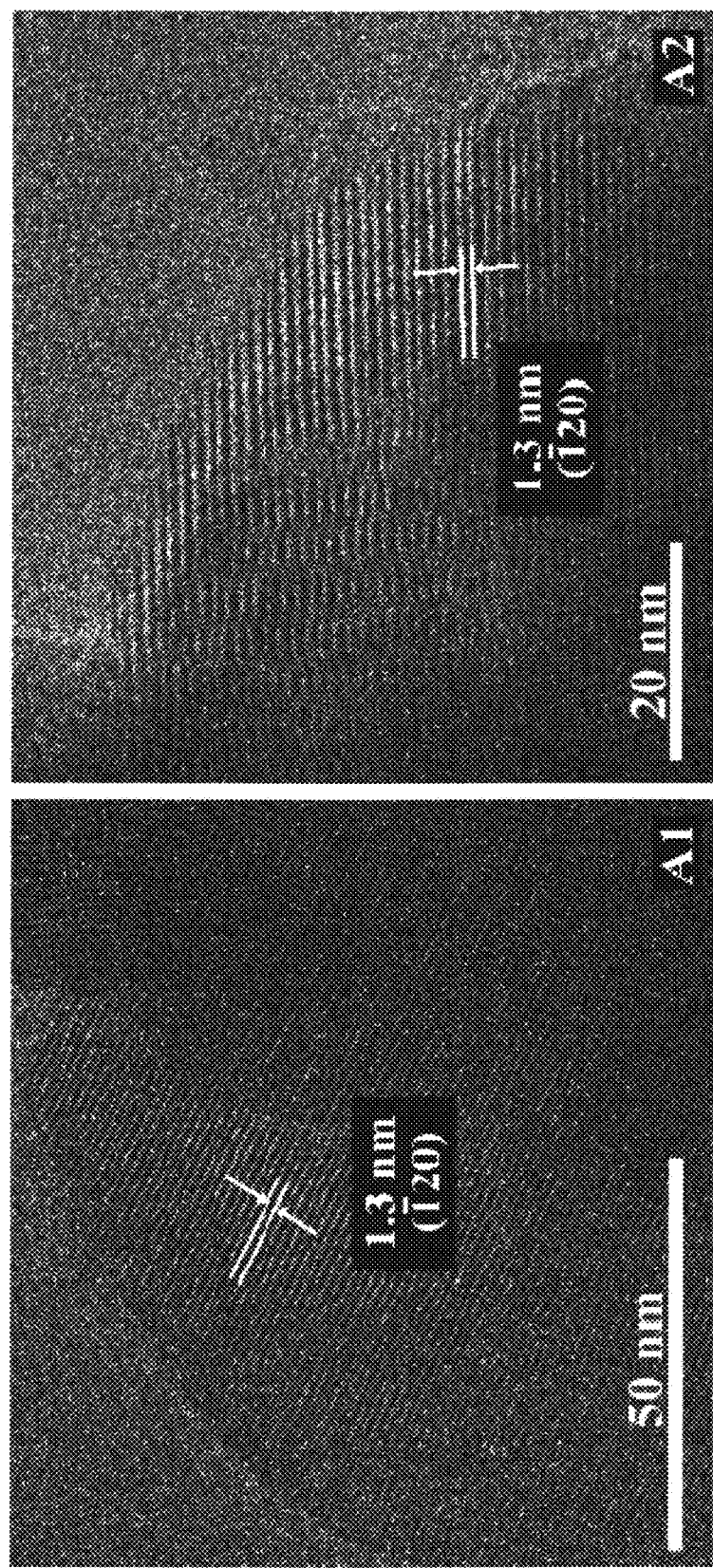
FIGS. 25A to 25C pictorially illustrate TEM images of samples synthesized without microwaves (FIG. 25A) and at two different temperatures in the microwave zone at 70° C.
Figure 25B:
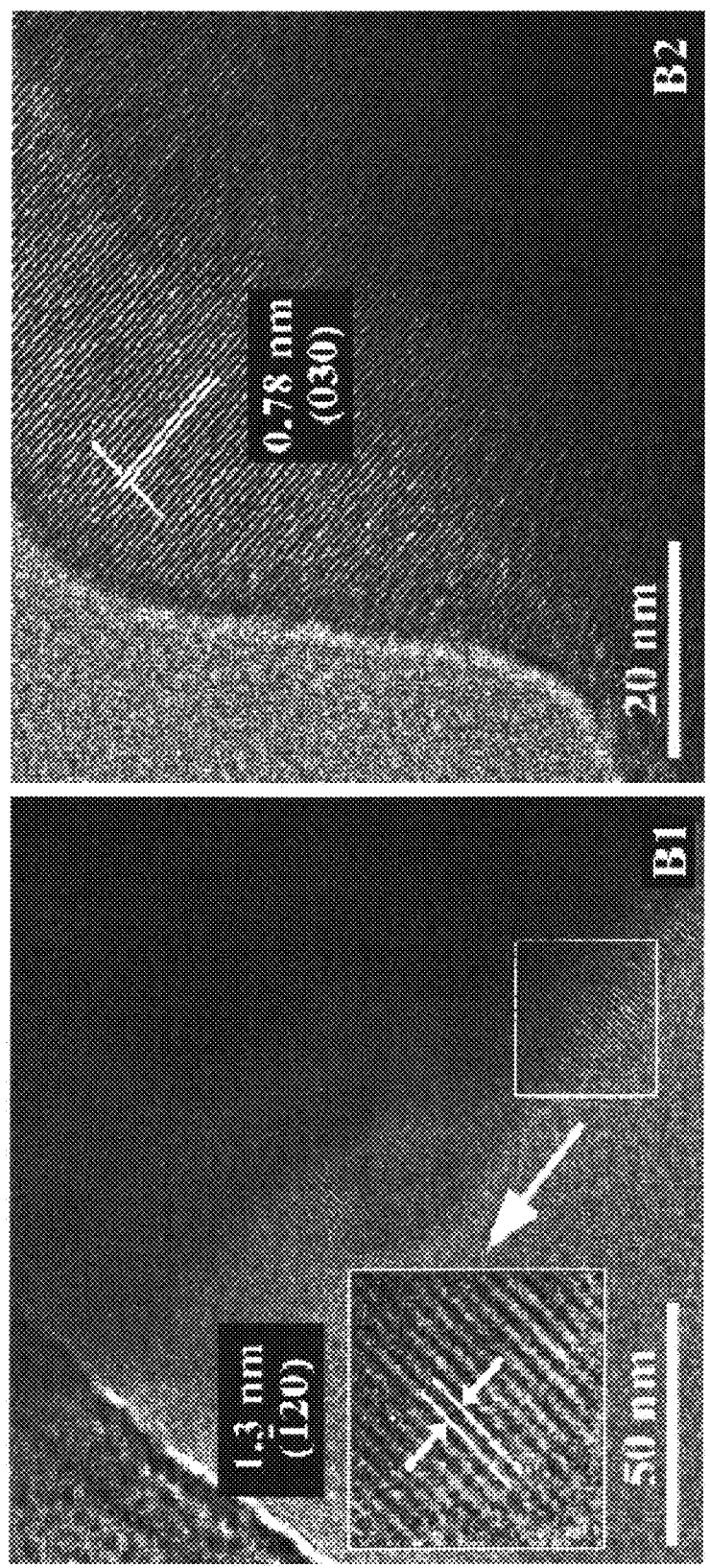
Figure 25C:
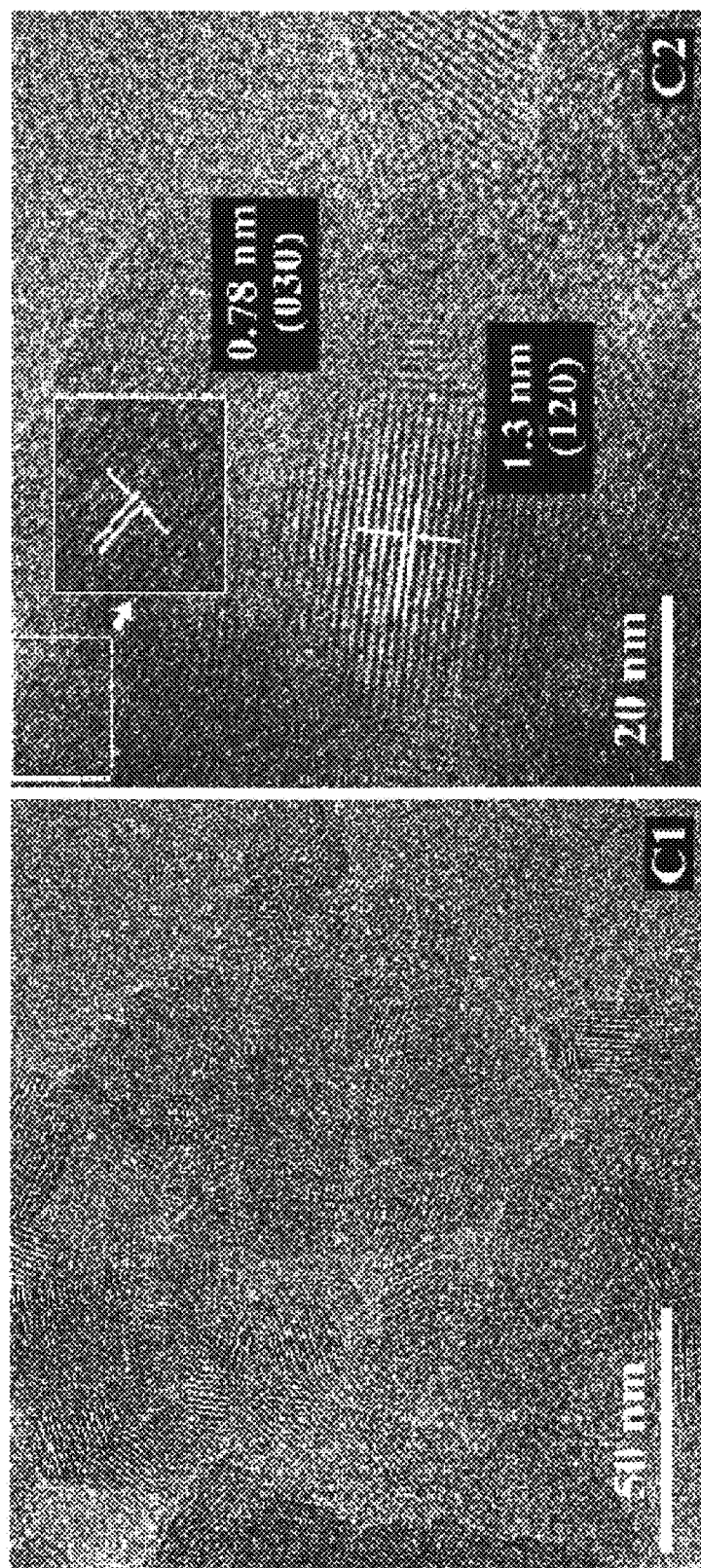
Figure 26:
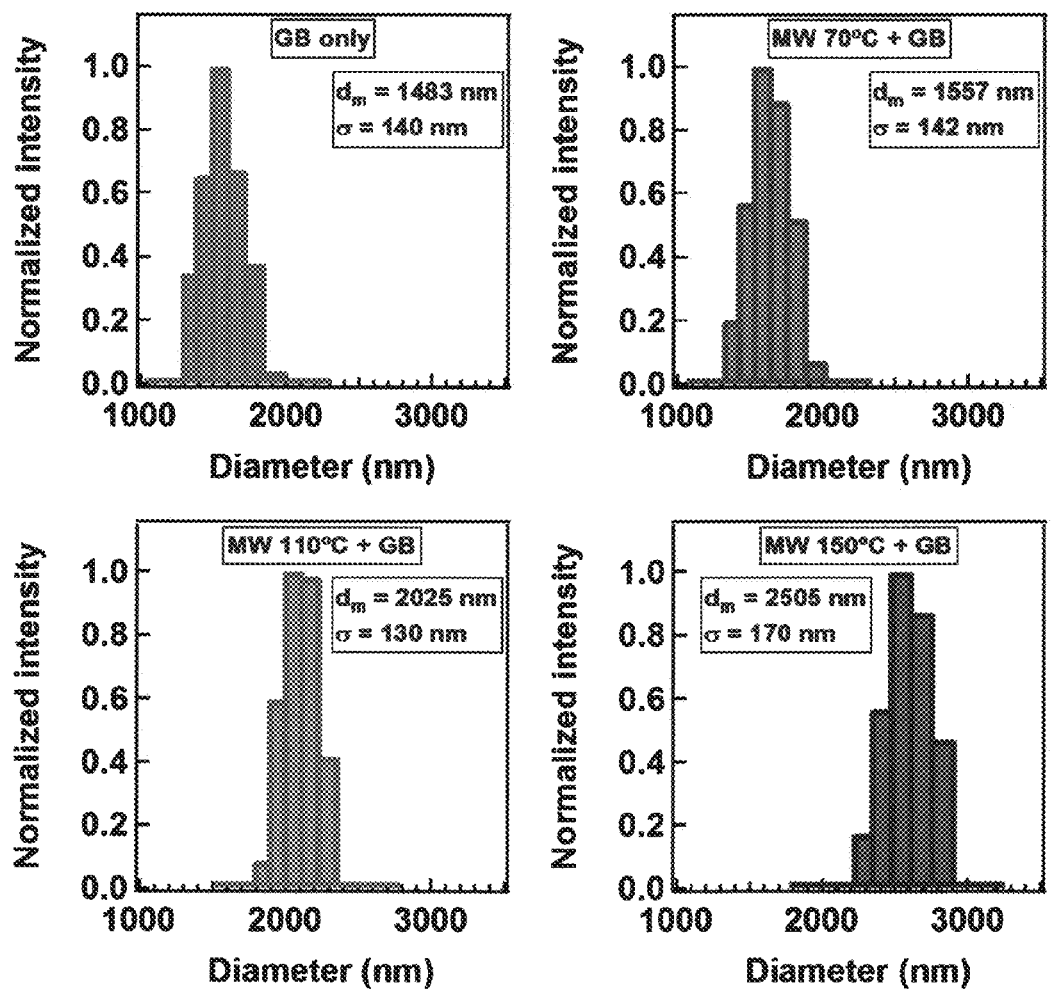
FIG. 26 graphically illustrates particle size measurements based on dynamic light scattering taken for samples synthesized with and without microwaves. Microwave temperatures were also varied. All samples presented very few particles in the 8-10 μm range which were omitted for clarity.

(See FIGS. 25 and 26) Larger grains in a polycrystalline material were observed on samples that were synthesized without any application of microwaves whereas high nucleation rates induced by rapid microwave heating, showed formation of smaller and agglomerated grains. The agglomeration and formation of a more polycrystalline material observed for higher applied powers explains the broadness of XRD and Raman spectroscopy peaks. No major differences were observed between the sample synthesized at $T_{MW}$=70° C. and the sample synthesized without microwaves. Distances between crystallographic planes were measured ($d_{hkl}$=1.3 nm and 0.78 nm) and values are very close to correspondent planes (−120) and (030) which are present in CPO-27-Ni structure and are related to peaks in X-rays diffraction at 2θ=6.8° ($d_{hkl}$=1.299 nm) and 11.8° ($d_{hkl}$=0.751 nm), respectively.

Figure 24:
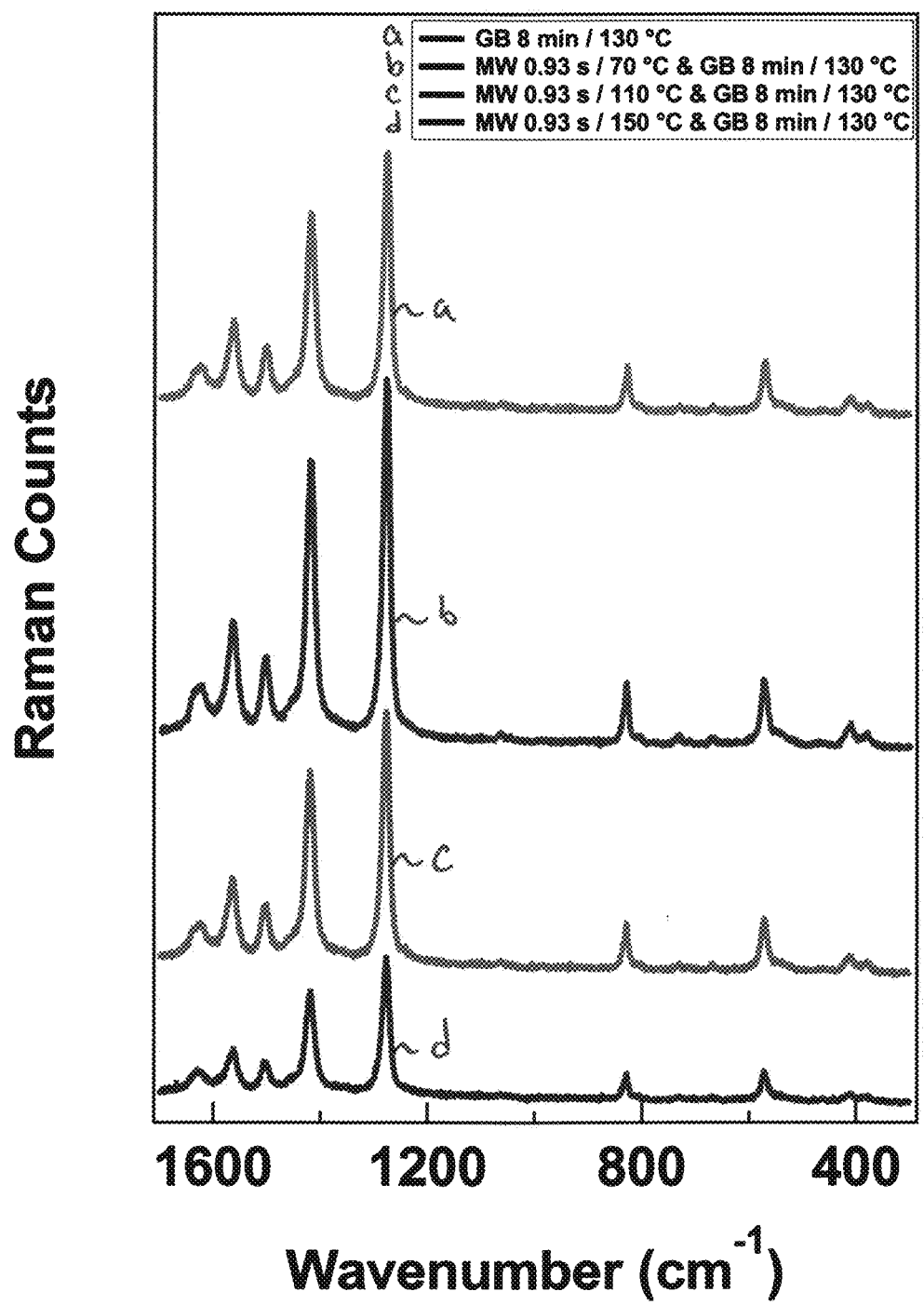
FIG. 24 graphically illustrates Raman spectra of CPO-27-Ni samples which were synthesized at different heating rates in the microwave zone while the growth bath was maintained at constant temperature and residence time: (a) growth bath at 8 mins at 130° C.; (b) microwave zone at 0.93 seconds at 70° C. and growth bath at 8 mins at 130° C.; (c) microwave zone at 0.93 seconds at 110° C. and growth bath 8 mins at 130° C.; and (d) microwave zone at 0.93 seconds at 150° C. and growth bath 8 mins at 130° C.

The increase of relative crystallinity shown by PXRD and Raman spectroscopy at $T_{MW}$=70° C. was a curious result since it seemed to be the only result that consistently showed an increase of relative crystallinity when compared to samples synthesized without microwaves applied (See Table 4 and FIG. 24). Without being limited to any one theory, this may be attributed to a balance between increased nucleation and reduction of both agglomeration and growth induced by fast reaction rates in microwave zone. Observed grains from synthesis at $T_{MW}$=70° C. are larger in comparison to when higher power was applied and comparable to grains in sample synthesized without application of microwaves.

Particle size measurements were also compared as higher microwave power was applied. As temperature in microwave zone increases particle size increases and a broader particle size distribution could be noticed for the sample synthesized at the highest temperature in microwave zone. Higher nucleation rates for the reaction maintaining similar conditions in growth bath should show a reduction of particle size since formation of more nuclei in the microwave zone would lead to smaller particles after the growth bath. However, without being limited to any one theory, high temperatures in microwave zone may lead to growth at high rates of diffusion, which associated with creation of hot spots at the surface of the product due to high microwave absorption, may lead to formation of non-uniform and agglomerated particles.

Figure 27:
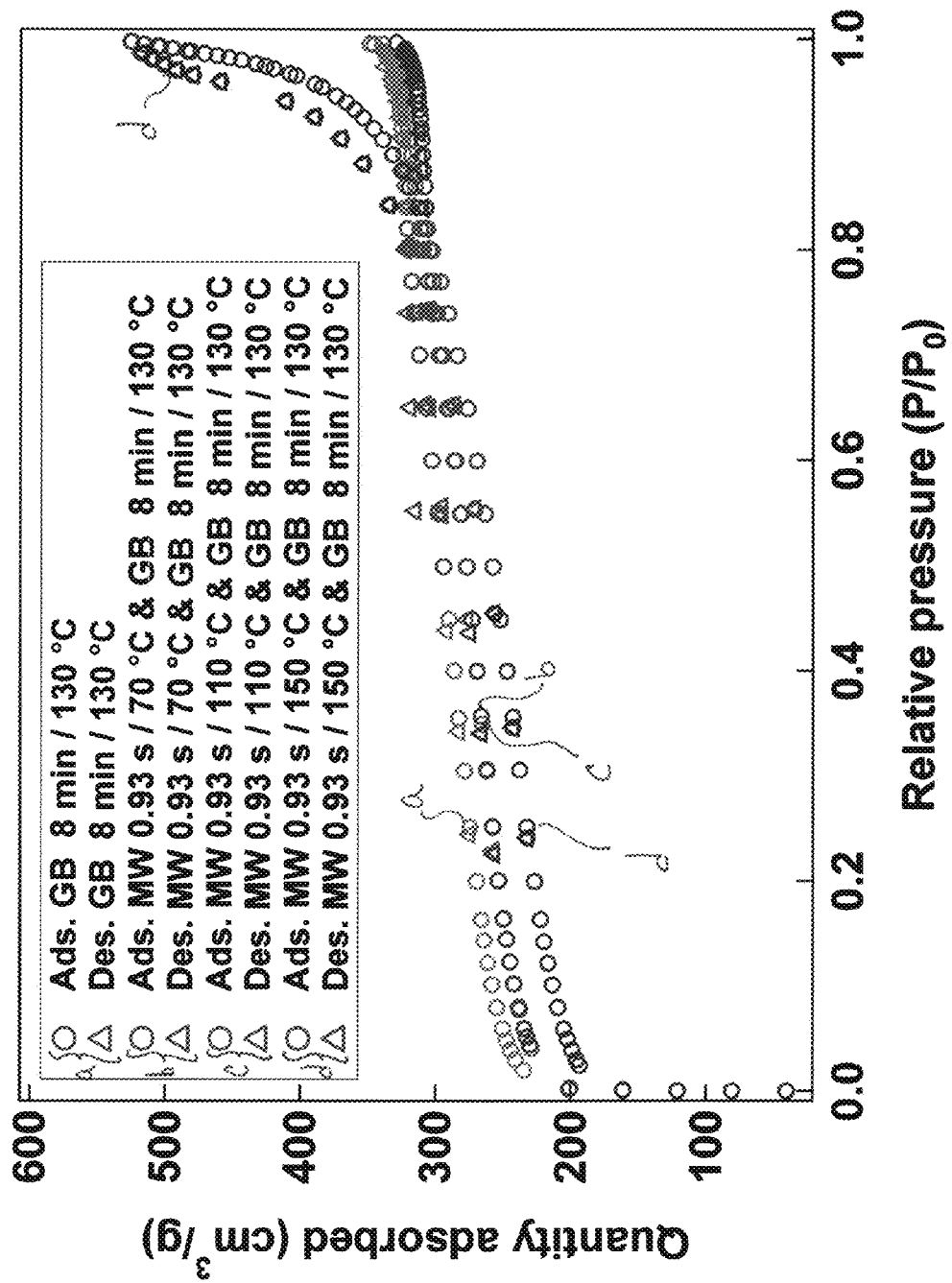
FIG. 27 graphically illustrates $N_2$ physisorption isotherms obtained for segmented continuous flow synthesis of CPO-27-Ni with and without MW power. Microwave power was also varied while heating bath conditions and volumetric flow rate were maintained fixed. Adsorption (Ads) and Desorption (Des) was measured at different relative pressures for the various tested conditions which are as follows: (a) growth bath at 8 mins at 130° C.; (b) microwave zone at 0.93 s at 70° C. and growth bath at 8 mins at 130° C.; (c) microwave zone at 0.93 seconds at 110° C. and growth bath at 8 mins at 130° C.; and (d) microwave zone at 0.93 seconds at 150° C. and growth bath at 8 mins at 130° C.
Figure 28:
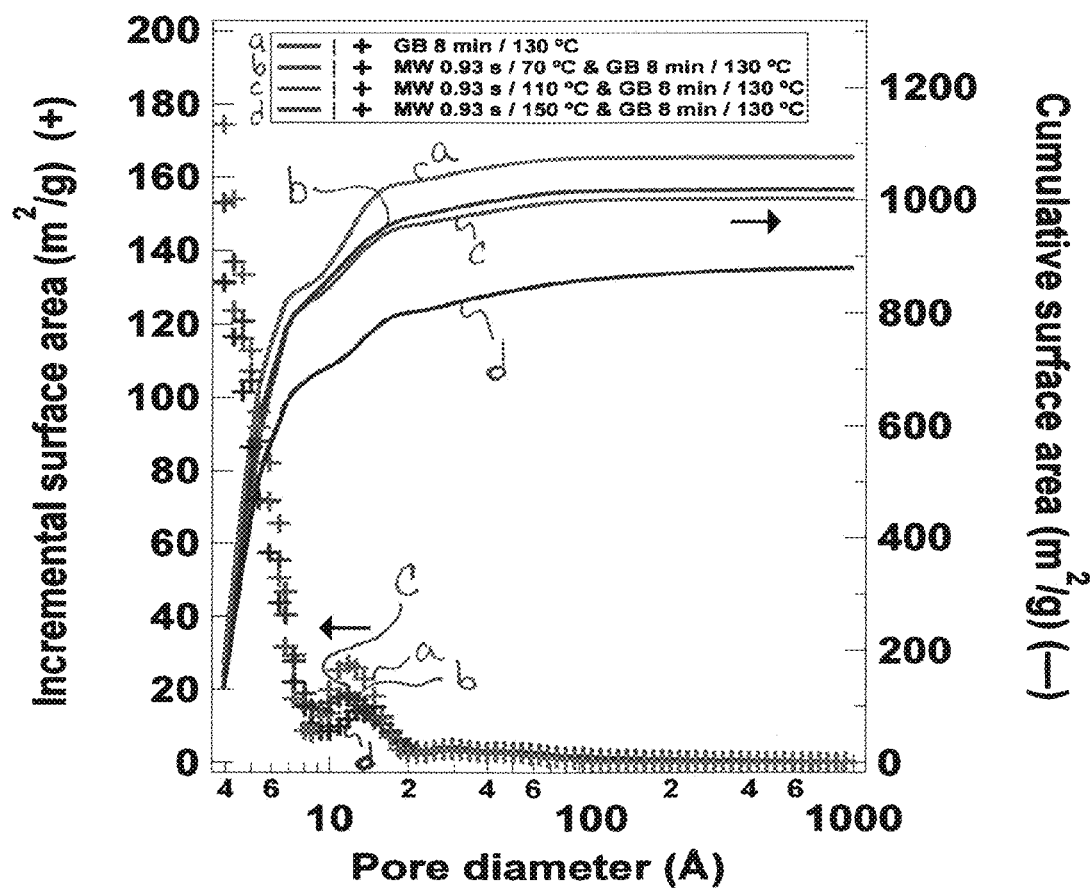
FIG. 28 graphically illustrates cumulative surface area (solid lines) and incremental surface area (crosses) for CPO-27-Ni synthesized using segmented flow with different microwave power levels while conditions in heating bath were held constant. The conditions tested are as follows: (a) growth bath at 8 mins at 130° C.; (b) microwave zone at 0.93 s at 70° C. and growth bath at 8 mins at 130° C.; (c) microwave zone at 0.93 seconds at 110° C. and growth bath at 8 mins at 130° C.; and (d) microwave zone at 0.93 seconds at 150° C. and growth bath at 8 mins at 130° C.

Physisorption was employed to evaluate the impact of different microwave power levels and differences on adsorption capacities of CPO-27-Ni. Isotherms were obtained for $N_2$ physisorption showing type I behavior for samples that were synthesized at lower temperatures in microwave zone or without any microwave applied (See FIG. 27). High power in MW zone changed the behavior of the isotherm to type 2 behavior, which is identified by accentuated increase of $N_2$ uptake at high relative pressures. That change can be attributed to the agglomeration of the small crystals shown in FIG. 26. High surface areas were calculated for all samples and an approximate diameter of 11Å was calculated for all samples which is in agreement with literature estimates for CPO-27-Ni. However, a lower surface area and slightly shifted peak can be seen for the sample prepared at 150° C. in MW zone. In addition different intensities of cumulative surface area varying with MW power can also be noticed which may be related to the agglomerated grains shown for this sample. This also explains the difference in total surface area available for each sample as a function of power(See Table 4). Pores and intracrystalline diffusion seem to be responsible for almost the total area taken into account in these measurements ($d_p$<20 Å) although some contribution seems to occur in the region of 20-100 Å which could be attributed to regions in between agglomerated particles (intercrystalline diffusion) (FIG. 28).

CPO-27-Ni has been synthesized in Lower power microwaves positively influenced relative crystallinity ($T_{MW}$=70° C.) but increase in relative crystallinity showed to form isotherms of similar behavior to samples synthesized in microwaves with similar values for BET isotherm surface area determination.

Segmented flow reduces the yield per volume of reactor per time. However, long reactions were run without any issues in both zones of the reactor while relatively high conversions and MOF mass production rates were achieved using a total volume of 50 mL (See Table 4). High conversions were obtained with 8 min of reaction which achieved mass production rates of 4-4.5 g/h representing a space-time yield of 80-90 g·h$^{-1}$·L$^{-1}$. Very stable temperatures were obtained in segmented flow regime for all reactions reported in this work which shows the simple control over heating of the liquid phase while gas bubbles are being inserted into the reactor.

Conclusions:

In summary, a continuous and segmented flow microwave-assisted synthesis of the CPO-27-Ni was performed under mild conditions of pressure (~2.5 bar) with high conversion of reagents (~96.5%) and space-time yield (~80-90 g·h$^{-1}$·L$^{-1}$). Segmented flow was employed to improve mixing and reduce particle fouling which allowed long reactions to be run with reproducibility of results.

Microwaves helped reducing reaction times down to 8 min and increased probability of nucleation which was indicated by TEM images. Faster nucleation induced a formation of smaller grains which after growth bath presented different adsorption behavior due to intercrystalline diffusion. High microwave absorption of CPO-27-Ni hot spots could cause accelerated diffusion toward particles and significant growth in microwave zone that could lead to heterogeneous particles. Tuning microwave power we were able to obtain better relative crystallinity and similar adsorption behavior to material synthesized without microwaves since significant nucleation occurred without heating particles formed.

Example 5

Synthesis and Processing of $Cu_2ZnSnS_4$ Nanoparticle Inks for Thin Film Solar Cells CZTS Nanocrystals.

$Cu_2ZnSnS_4$ (CZTS) is a material that may be used in the preparation of solar cells and has a direct bandgap of about 1.5 eV which allows it to efficiently absorb sunlight with a film thickness less than 1.5 microns. All of the constituent elements of a representative solar cell may be relatively non-toxic, earth-abundant, and may be sourced domestically. Moreover, record efficiency for CZTSSe is 12.6%, almost doubled within the last 5 years.

Synthesis of CZTS Nanocrystals.

Figure 29:
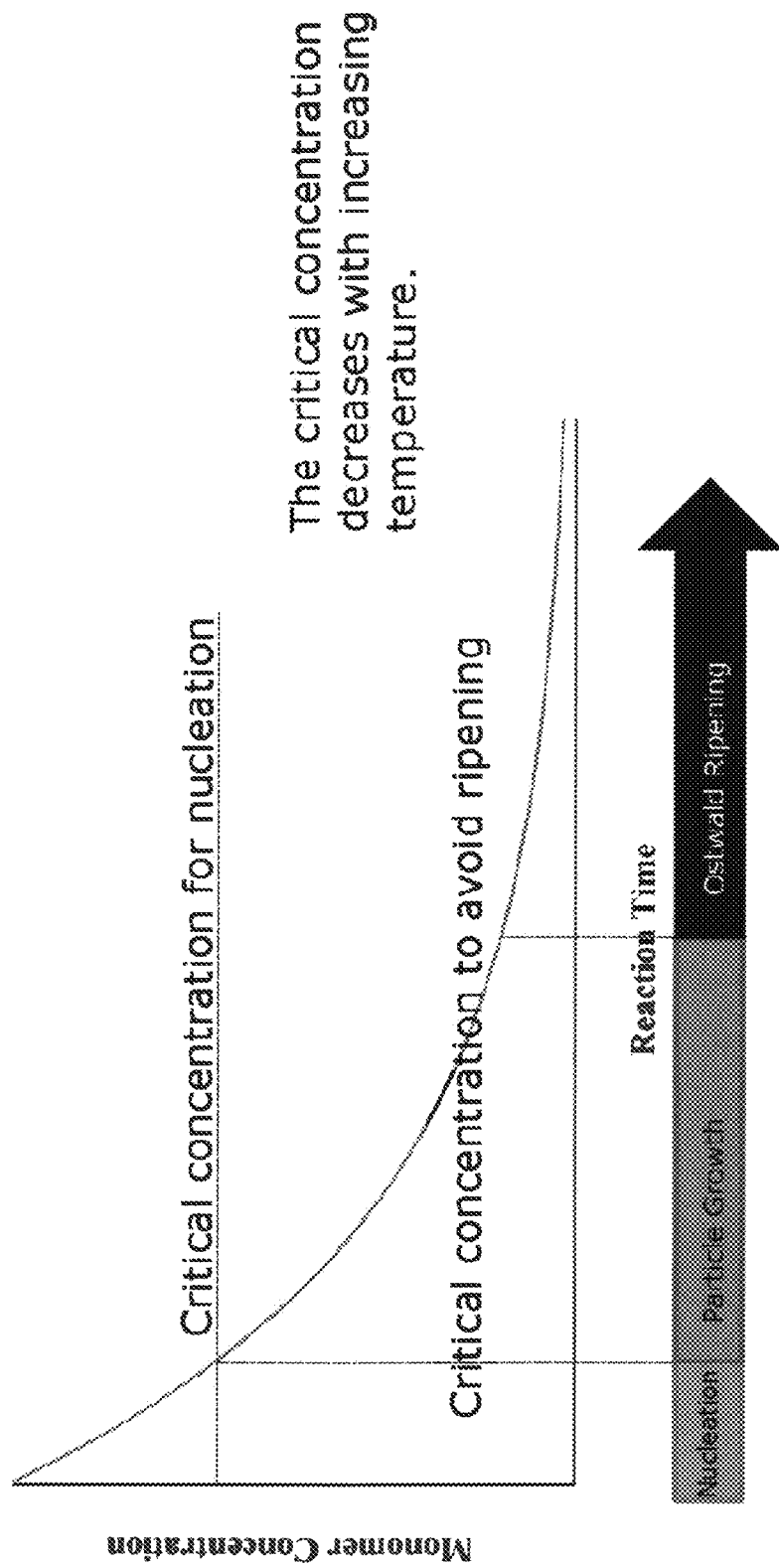
FIG. 29 graphically illustrates the effect of monomer concentration on reaction time in the control of nucleation and growth of NPs. Nucleation may occur by increasing monomer concentration above the critical point (hot injection) or by heating above the critical temperature (heat up).

Controlling particle size is important for producing uniform films that include nanocrystals. Separating the nucleation of new particles from growth of existing particles is important to achieving narrow nanoparticle size. Nucleation can occur by increasing monomer concentration above the critical point (hot injection) or by heating above the critical temperature (heat up). (See FIG. 29).

Figure 30:
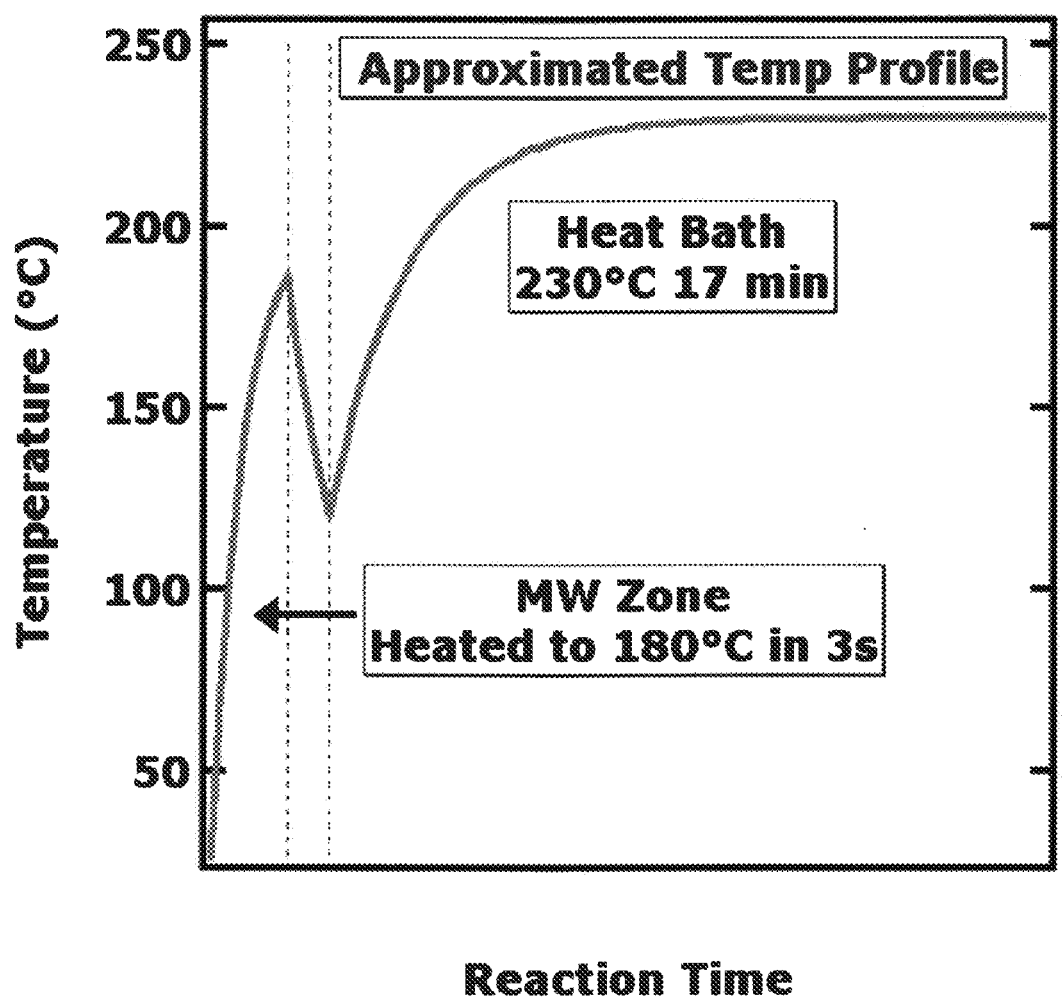
FIG. 30 graphically demonstrates the approximated temperature profile for a reaction taking place in a system of the invention during the synthesis of CZTS NPs.

Using a continuous flow microwave reactor system of the invention, which includes segmentation, olelyamine may be used as a solvent/capping ligand to facilitate cleaning and improve film quality. Metal chloride salts and elemental sulphur were separately dissolved in oleylamine and mixed at room temperature prior to reaction. Oleylamine is a low absorbing solvent and higher microwave intensity was required compared with a TEG system (see FIG. 30).

TEM and Raman Spectroscopy Scan of CFMW CZTS NPs.

Figure 31:
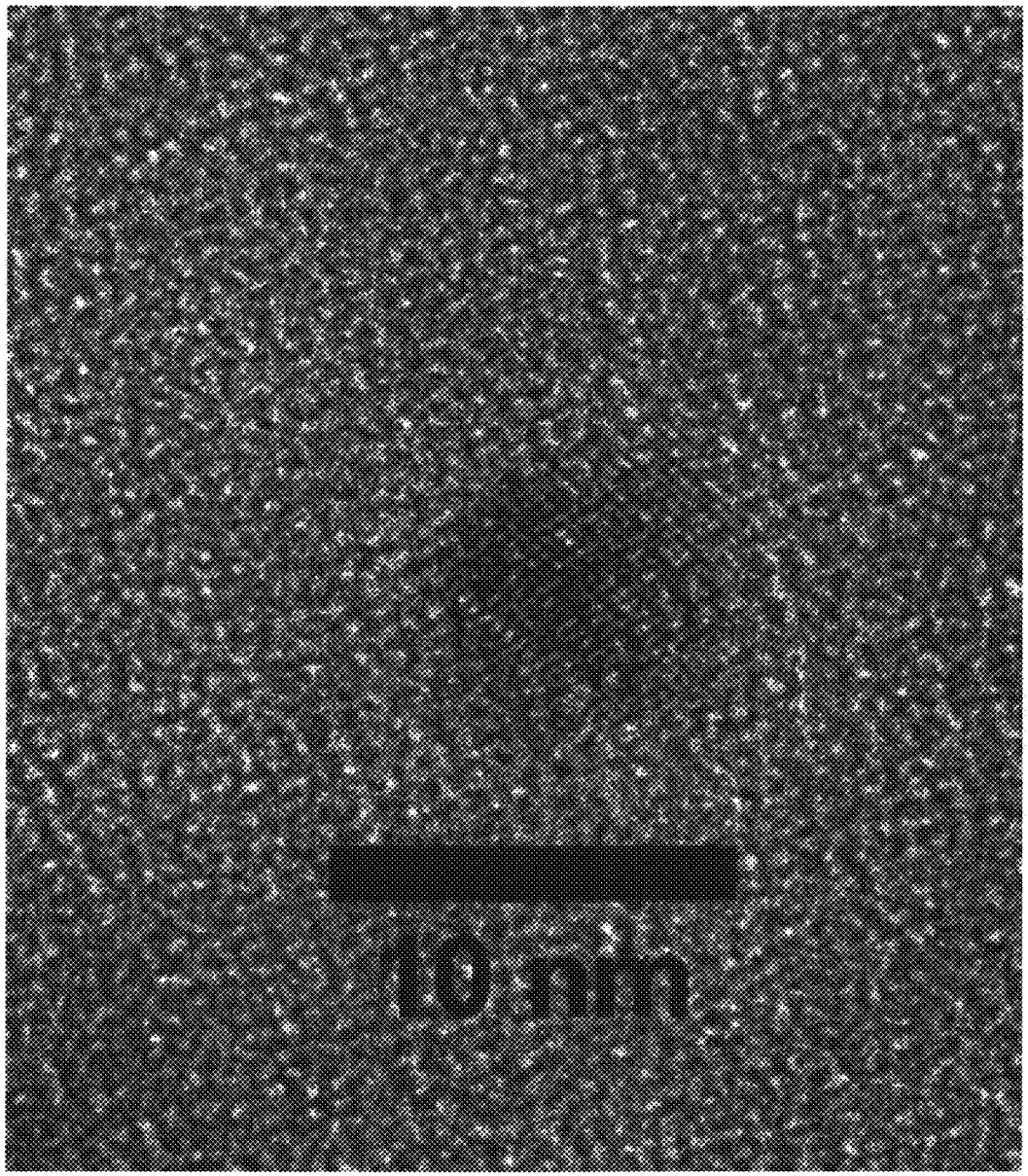
FIG. 31 pictorially illustrates a TEM image of CZTS NPs synthesized by a system of the invention.
Figure 32:
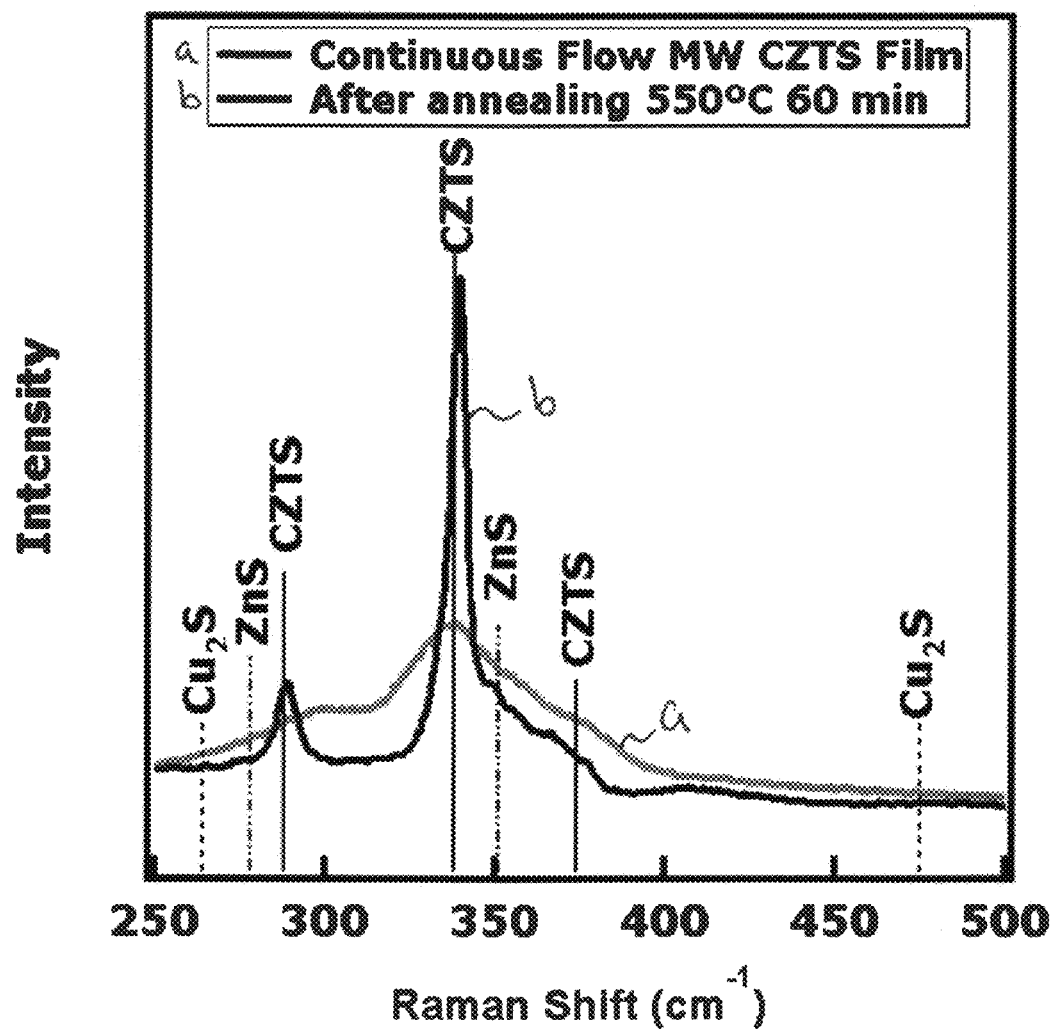
FIG. 32 graphically illustrates the Raman spectra of (a) a CZTS film synthesized by a system of the invention; and (b) a CZTS film synthesized by a system of the invention after annealing at 550° C. for 60 minutes.

Raman spectroscopy demonstrates the characteristic peaks for CZTS without any significant impurity peaks. The CZTS nanocrystals prepared by the system of the invention demonstrate an average particle diameter of 10±2 nm. (See FIGS. 31 and 32).

Summary.

Previous experience in microwave and continuous flow synthesis of CZTS NPs was leveraged to produce CZTS NP materials. Synthesis in oleylamine facilitated cleaning and resulted in particles of the desired crystal structure without significant impurities.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All systems and methods that embody the present invention can, in alternate embodiments, be more specifically defined by any of the transitional terms "comprising", "consisting essentially of" and "consisting of".

REFERENCES

1. B. J. Stanbery, *Crit. Rev. Solid State Mater. Sci.*, 2002, 27, 73.
2. M. Kemell, M. Ritala and M. Leskela, *Crit. Rev. Solid State Mater. Sci.*, 2005, 30, 1.
3. S. Siebentritt, *Sol. Energy Mater. Sol. Cells*, 2011, 95, 1471.
4. D. Aldakov, A. Lefrancois and P. Reiss, *J. Mater. Chem. C*, 2013, 1, 3756.
5. O. Chen, H. Wei, A. Maurice, M. Bawendi and P. Reiss, *MRS Bulletin*, 2013, 38, 696.
6. E. Cassette, T. Pons, C. Bouet, M. Helle, L. Bezdetnaya, F. Marchal and B. Dubertret, *Chem. Mater.*, 2010, 22, 6117.
7. V. A. Akhavan, B. W. Goodfellow, M. G. Panthani, D. K. Reid, D. J. Hellebusch, T. Adachi and B. A. Korgel, *Energy Environ. Sci.*, 2010, 3, 1600.
8. W.-J. Wang, Y. Jiang, X.-Z. Lan, C. Wang, X.-M. Liu, B.-B. Wang, J.-W. Li, B. Yang and X.-N. Ding, *Mater. Sci. Semicond. Process.*, 2012, 15, 467.
9. Q. Guo, S. J. Kim, M. Kar, W. N. Shafarman, R. W. Birkmire, E. A. Stach, R. Agrawal and H. W. Hillhouse, *Nano Lett.*, 2008, 8, 2982.
10. D. B. Mitzi, *Adv. Mater.*, 2009, 21, 3141.
11. M. E. Norako and R. L. Brutchey, *Chem. Mater.*, 2010, 22, 1613.
12. M. G. Panthani, V. Akhavan, B. Goodfellow, J. P. Schmidtke, L. Dunn, A. Dodabalapur, P. F. Barbara and B. A. Korgel, *J. Am. Chem. Soc.*, 2008, 130, 16770.
13. H. Zhong, Y. Li, M. Ye, Z. Zhu, Y. Zhou, C. Yang and Y. Li, *Nanotechnology*, 2007, 18, 025602.
14. J. Tang, S. Hinds, S. O. Kelly and E. H. Sargent, *Chem. Mater.*, 2008, 20, 6906.
15. W. Wang, Y.-W. Su and C.-H. Chang, *Sol. Energy Mater. Sol. Cells*, 2011, 95 2616.
16. W. Wang, S.-Y. Han, S.-J. Sung, D.-H. Kim and C.-H. Chang, *Phys. Chem. Chem. Phys.*, 2012, 14, 11154.
17. S. E. Habas, H. A. S. Platt, M. F. A. M. van Hest and D. S. Ginley, *Chem. Rev.*, 2010, 110, 6571.
18. H. W. Hillhouse and M. C. Beard, *Curr. Opin. Colloid Interface Sci.*, 2009, 14, 245.
19. J. Jean, S. Chang, P. R. Brown, J. J. Cheng, P. H. Rekemeyer, M. G. Bawendi, S. Gradečk and V. Bulović, *Adv. Mat.*, 2013, 25, 2790.
20. I. Gur, N. A. Fromer, M. L. Geier and A. P. Alivisatos, *Science*, 2005, 310, 462.
21. A. Shavel, D. Cadavid, M. Ibanez, A. Carrete and A. Cabot, *J. Am. Chem. Soc.*, 2011, 134, 1438.
22. G. J. Supran, Y. Shirasaki, K. W. Song, J. M. Caruge, P. T. Kazlas, S. Coe-Sullivan, T. L. Andre, M. G. Bawendi and V. Bulović, *MRS Bulletin*, 2013, 38, 703.
23. Y. Yin and A. P. Alivisatos, *Nature*, 2005, 437, 664.
24. J. Park, K. An, Y. Hwang, J.-G. Park, H.-J. Noh, J.-Y. Kim, J.-H. Park, N.-M. Hwang and T. Hyeon, *Nat. Mater.*, 2004, 3, 891.
25. J. Park, J. Joo, S. G. Kwon, Y. Jang and T. Hyeon, *Angew. Chem. Int. Ed.*, 2007, 46, 4630.
26. B. Li, Y. Xie, J. Huang and Y. Qian, *Adv. Mater.*, 1999, 11, 1456.
27. C. J. Carmalt, D. E. Morrison and I. P. Parkin, *J. Mater. Chem.*, 1998, 8, 2209.
28. M. A. Malik, P. O'Brien and N. Revaprasadu, *Adv. Mater.*, 1999, 11, 1441.
29. M. Kar, R. Agrawal and H. W. Hillhouse, *J. Am. Chem. Soc.*, 2011, 133, 17239.
30. H. D. Jin and C.-H. Chang, *J. Nanopart. Res.*, 2012, 14, 1180.
31. J. Xu, C.-S. Lee, Y.-B. Tang, X. Chen, Z.-H. Chen, W.-J. Zhang, S.-T. Lee, W. Zhang and Z. Yang, *ACS Nano*, 2010, 4, 1845.
32. S. Deka, A. Genovese, Y. Zhang, K. Miszta, G. Bertoni, R. Krahne, C. Giannini and L. Manna, *J. Am. Chem. Soc.*, 2010, 132, 8912.
33. C. M. Hessel, V. P. Pattani, M. Rasch, M. G. Panthani, B. Koo, J. W. Tunnell and B. A. Korgel, *Nano Lett.*, 2011, 11, 2560.
34. S. L. Castro, S. G. Bailey, R. P. Raffaelle, K. K. Banger and A. F. Hepp, *Chem. Mater.*, 2003, 15, 3142.
35. B. Koo, R. N. Patel and B. A. Korgel, *J. Am. Chem. Soc.*, 2009, 131, 3134.

36. C. Steinhagen, V. A. Akhavan, B. W. Goodfellow, M. G. Panthani, J. T. Harris, V. C. Holmberg and B. A. Korgel, *ACS Appl. Mater. Interfaces,* 2011, 3, 1781.
37. V. A. Akhavan, M. G. Panthani, B. W. Goodfellow, D. K. Reid and B. A. Korgel, *Opt. Express,* 2010, 18, A411.
38. S. Jeong, B.-S. Lee, S. J. Ahn, K. H. Yoon, Y.-H. Seo, Y. Choi and B.-H. Ryu, *Energy Environ. Sci.,* 2012, 5, 7539.
39. Kim, K. J., et al., *Crystal Growth and Des.,* 2014, 14, 5349.
40. Hostetler, E. B., et al., *Materials Letters,* 2014, 128, 54.
41. Wang, W., et al., *Adv. Ener. Mater.,* 2014, 10, 1002.
42. Flynn, B., et al., *Physica Status Solidi A,* 2012, 209, 2186.
43. Yen, *Angewandte Chemie,* 2005, 117, 5583.
44. Flynn, B., et al., *Materials Letters,* 2013, 107, 214.

What is claimed is:

1. A continuous, microwave-assisted, segmented flow reactor system for nanocrystal synthesis, comprising:
   a. a nanocrystal precursor source configured to comprise a nanocrystal precursor solution;
   b. a microwave reactor in fluid communication with the nanocrystal precursor source and having a fluid passageway passing through the microwave reactor configured to allow the nanocrystal precursor solution to pass therethrough; and
   c. a segmentation fluid source disposed in fluid communication with the fluid passageway at a location between the nanocrystal precursor source and the microwave reactor, the segmentation fluid source configured to provide a segmentation fluid that is immiscible with the nanocrystal precursor solution.

2. The system of claim 1, wherein the segmentation fluid source comprises a valve.

3. The system of claim 1, wherein the segmentation fluid source comprises a pump.

4. The system of claim 1, wherein the segmentation fluid comprises a gas, a liquid, or a combination thereof.

5. The system of claim 1, wherein the segmentation fluid comprises a gas, a liquid, or a combination thereof where bubble or droplet flow occurs.

6. The system of claim 1, wherein the nanocrystal precursor solution comprises Cu, In, S, Ga, Se, Pb, Sn, Zn, P, Cd, Te, Ge, Si, Hg, O, Ag, Sb, Bi, Na, or a combination thereof.

7. The system of claim 1, wherein the nanocrystal precursor source comprises a first nanocrystal precursor source and second nanocrystal precursor source; and the nanocrystal precursor solution comprises a first nanocrystal precursor solution and a second nanocrystal precursor solution.

8. The system of claim 7, comprising a nanocrystal precursor mixer in fluid communication with the first nanocrystal precursor source and the second nanocrystal precursor source and configured to mix the first nanocrystal precursor solution and the second nanocrystal precursor solution.

9. The system of claim 7, wherein the first nanocrystal precursor source comprises a first precursor pump and the second nanocrystal precursor source comprises a second precursor pump.

10. The system of claim 1, comprising a growth chamber for growing nanocrystals in fluid communication with the microwave reactor.

11. The system of claim 1, wherein the segmentation fluid comprises an inert gas.

12. A method for synthesizing nanocrystals using a continuous, microwave-assisted, segmented flow reactor, the method comprising the steps of:
   a. providing a nanocrystal precursor solution;
   b. segmenting the nanocrystal precursor solution with a segmentation fluid that is immiscible with the nanocrystal precursor solution to yield a segmented nanocrystal precursor solution;
   c. continuously flowing the segmented nanocrystal precursor solution through a microwave reactor having a microwave zone; and
   d. irradiating the segmented nanocrystal precursor solution flowing through the microwave zone to provide nanocrystals.

13. The method of claim 12, wherein the step of providing a nanocrystal precursor solution comprises mixing.

14. The method of claim 12, wherein the segmentation fluid comprises a gas, liquid, or a combination thereof.

15. The method of claim 12, wherein the step of irradiating comprises a microwave zone residence time of about 0.1 to 100 seconds.

16. The method of claim 12, wherein the step of irradiating comprises a microwave zone residence time of about 0.1 to 10 seconds.

17. The method of claim 12, wherein the microwave zone residence time is about 5 seconds.

18. The method of claim 12, wherein the microwave zone comprises a temperature of about 25 to 250° C.

19. The method of claim 12, wherein the microwave zone comprises a temperature of about 50 to 200° C.

20. The method of claim 12, wherein the microwave zone comprises a temperature of about 180° C.

21. The method of claim 12, further comprising the step of growing nanocrystals in a growth zone.

22. The method of claim 21, wherein in the step of growing nanocrystals comprises a growth zone residence time of about 5 minutes to 30 minutes.

23. The method of claim 22, wherein the growth zone residence time is about 20 minutes.

24. The method of claim 21, wherein the growth zone comprises a temperature of about 50 to 250° C.

25. The method of claim 21, wherein the growth zone comprises a temperature of about 210° C.

26. The method of claim 12, wherein the nanocrystal precursor solution comprises Cu, In, S, Ga, Se, Pb, Sn, Zn, P, Cd, Te, Ge, Si, Hg, O, Ag, Sb, Bi, Na, or a combination thereof.

27. The method of claim 12, wherein the nanocrystal precursor solution comprises Cu, In, Se, Pb, S, Sn, Zn, or a combination thereof.

28. The method of claim 12, wherein the nanocrystal precursor solution comprises Cu, In, Se, or a combination thereof.

29. The method of claim 12, wherein the nanocrystal comprises $CuInSe_2$, PbSe, $CuInS_2$, $Cu_2ZnSnS_4$, or a combination thereof.

30. The method of claim 12, wherein the nanocrystal comprises $CuInSe_2$.

31. The method of claim 12, wherein the nanocrystal precursor solution comprises a first and second nanocrystal precursor.

32. The method of claim 12, wherein the nanocrystal precursor solution comprises oleylamine, trioctylphosphine, trioctylphosphine oxide, hexadecylamine, water, triethylene glycol, ethylene glycol, oleic acid, dodecanethiol, dioctyl ether, 1-octadecene, glycerol, 1,3-propanediol-1,4-butanediol, or a combination thereof.

33. The method of claim 12, wherein the segmentation fluid comprises an inert gas.

34. A continuous flow reactor comprising:
a mixer for mixing a first and a second precursor together into a mixture and providing the mixture to a fluid passageway;
a segmentation fluid source for inserting a gas into the fluid passageway to provide segmented flow of the mixture along the fluid passageway;
an energy source for nucleating the segmented flow of the mixture in the fluid passageway, thereby producing nucleates; and
a heating source for growing the nucleates in the fluid passageway thereby growing the nucleates into nanoparticles.

35. The continuous flow reactor of claim 34, wherein the energy source is a microwave.

36. The continuous flow reactor of claim 34, wherein the gas comprises an inert gas.

\* \* \* \* \*